(12) United States Patent
Yokoyama et al.

(10) Patent No.: US 10,352,678 B2
(45) Date of Patent: Jul. 16, 2019

(54) COEFFICIENT-OF-THERMAL-EXPANSION MEASUREMENT METHOD OF DIMENSION REFERENCE GAUGE, MEASURING DEVICE FOR COEFFICIENT OF THERMAL EXPANSION AND REFERENCE GAUGE

(71) Applicant: MITUTOYO CORPORATION, Kawasaki-shi, Kanagawa (JP)

(72) Inventors: Yuichiro Yokoyama, Abiko (JP); Takeshi Hagino, Tsukuba (JP); Yutaka Kuriyama, Tsukuba (JP)

(73) Assignee: MITUTOYO CORPORATION, Kawasaki (JP)

( * ) Notice: Subject to any disclaimer, the term of this patent is extended or adjusted under 35 U.S.C. 154(b) by 229 days.

(21) Appl. No.: 15/271,593

(22) Filed: Sep. 21, 2016

(65) Prior Publication Data

US 2017/0089683 A1 Mar. 30, 2017

(30) Foreign Application Priority Data

Sep. 25, 2015 (JP) ................................. 2015-188093
Oct. 30, 2015 (JP) ................................. 2015-215240
Oct. 30, 2015 (JP) ................................. 2015-215241

(51) Int. Cl.
*G01B 5/008* (2006.01)
*G01N 25/16* (2006.01)

(52) U.S. Cl.
CPC ............. *G01B 5/008* (2013.01); *G01N 25/16* (2013.01)

(58) Field of Classification Search
CPC ...... G01B 5/008; G01B 5/045; G01B 21/045; G01N 25/16
See application file for complete search history.

(56) References Cited

U.S. PATENT DOCUMENTS 5,031,331 A * 7/1991 Herzog ................ G01B 5/0014
33/1 M
5,446,971 A * 9/1995 Neumann ............ G01B 5/0014
33/503
(Continued)

FOREIGN PATENT DOCUMENTS

CN 102788810 A 11/2012
DE 8910636 U1 10/1989
(Continued)

OTHER PUBLICATIONS

Computer translation of JP 2004-226369 Aug. 22, 2018.*
Mar. 9, 2017 Extended Search Report issued in European Patent Application No. 16190535.1.

Primary Examiner — Randy W Gibson
(74) Attorney, Agent, or Firm — Oliff PLC

(57) ABSTRACT

A measurement target and a reference gauge are placed in parallel in an inside of a temperature-controlled chamber. After an interior temperature of the temperature-controlled chamber is set at a first temperature, a relative measurement of a length from a first surface to a second surface of the measurement target is performed with reference to a length from a first reference surface to a second reference surface of the reference gauge. Then, the interior temperature of the temperature-controlled chamber is set at a second temperature and a relative measurement of the length from the first surface to the second surface is similarly performed with reference to the length from the first reference surface to the second reference surface. A CTE of the measurement target is calculated based on the length of the measurement target at the first temperature and the length of the measurement target at the second temperature.

24 Claims, 48 Drawing Sheets

(56) References Cited

U.S. PATENT DOCUMENTS

| | | | | |
|---|---|---|---|---|
| 6,178,389 B1* | 1/2001 | Sola | ............ | G01B 5/008 33/503 |
| 6,532,680 B2* | 3/2003 | Braasch | ............ | G01B 7/16 33/503 |
| 6,866,451 B2* | 3/2005 | Braasch | ............ | G01B 7/20 33/702 |
| 7,089,146 B1* | 8/2006 | D'Aquino | ............ | G01K 7/01 257/467 |
| 7,188,432 B2* | 3/2007 | Schepperle | ............ | G01B 5/0014 33/503 |
| 9,664,629 B2* | 5/2017 | Sakai | ............ | G01B 21/045 |
| 2010/0299094 A1* | 11/2010 | Hsu | ............ | G01B 5/0014 702/95 |
| 2012/0185210 A1* | 7/2012 | Takanashi | ............ | G01B 5/201 702/168 |
| 2015/0131697 A1* | 5/2015 | Sakai | ............ | G01B 21/045 374/56 |
| 2015/0211835 A1* | 7/2015 | Merlo | ............ | G01B 5/0014 702/95 |
| 2018/0180396 A1* | 6/2018 | Hagino | ............ | G01B 5/0009 |

FOREIGN PATENT DOCUMENTS

| | | | | |
|---|---|---|---|---|
| DE | 4436782 | * | 4/1995 | ............ G01N 25/16 |
| DE | 102012219417 A1 | | 4/2014 | |
| JP | 2004-226369 A | | 8/2004 | |
| JP | 2005-083920 A | | 3/2005 | |
| JP | 3897655 B2 | | 3/2007 | |
| KR | 101365972 B1 | | 2/2014 | |

\* cited by examiner

COEFFICIENT-OF-THERMAL-EXPANSION MEASUREMENT METHOD OF DIMENSION REFERENCE GAUGE, MEASURING DEVICE FOR COEFFICIENT OF THERMAL EXPANSION AND REFERENCE GAUGE

The entire disclosure of Japanese Patent Applications No. 2015-188093 filed Sep. 25, 2015, No. 2015-215240 filed Oct. 30, 2015, and No. 2015-215241 filed Oct. 30, 2015 is expressly incorporated by reference herein.

TECHNICAL FIELD

The present invention relates to a coefficient-of-thermal-expansion measurement method of a dimension reference gauge, a measuring device for coefficient of thermal expansion (CTE measuring device) and a reference gauge.

BACKGROUND ART

Dimension reference gauges are used in testing measuring devices such as coordinate measuring machines.

Step gauges corresponding to a plurality of lengths as well as various gauge blocks whose end-to-end dimension is highly accurately calibrated are used for the dimension reference gauge.

The step gauges are comb-shaped components having alternately arranged protrusions and recesses, where a plurality of reference dimensions are defined between end faces of the protrusions. The step gauges are produced by alternately arranging measurement blocks defining the protrusions and spacer blocks defining the recesses and fixing the arranged blocks on a holder. Alternatively, the step gauges are produced by cutting a single component into a form of the comb-shaped component.

A calibration value of the end-to-end dimension of the step gauges is defined as a length at a specific temperature and is often defined as a length at 20 degrees C. (industrial standard temperature).

In testing a coordinate measuring machine, the measured length has to be converted to a length at a temperature during the calibration, which is usually referred to as a length temperature correction. At this time, it is necessary that a coefficient of thermal expansion (CTE) of the step gauge is accurately known.

The CTE used for the temperature correction is written in a calibration certificate or a test certificate for most of the dimension reference gauges including step gauges. Such a CTE is indicated with tolerance.

When a step gauge is used for testing a coordinate measuring machine, the tolerance is considered as a factor of uncertainty in determining uncertainty of the test. Accordingly, it is required that the CTE of the step gauge is highly accurately evaluated in order to reduce the uncertainty in the test.

CTE of an object including a dimension reference gauge is obtained by changing the temperature of the object and measuring a length variation of the object due to the temperature change.

Specifically, a CTE $\alpha$ is given by a formula $\alpha=(\Delta L/L)\cdot(1/\Delta T)$, where $\Delta T=T-T_o$ (T: a current temperature, $T_o$: a reference temperature) represents the temperature variation, and $\Delta L=L-L_o$ (L: a length of the object at the current temperature T, $L_o$: a length of the object at the reference temperature $T_o$) represents the length variation (thermal expansion).

In a dimension reference gauge such as a step gauge, the length L of the object is more than $10^5$ times larger than the length variation $\Delta L$. Accordingly, the accuracy of the value of the length L has relatively a small impact on the value of the CTE $\alpha$.

Accordingly, in order to highly accurately calculate the CTE $\alpha$, it is necessary to highly accurately measure the temperature variation $\Delta T$ and the length variation $\Delta L$.

In order to measure the CTE $\alpha$, a measuring method using an optical interferometer has been proposed (Patent Literature 1: JP-B-3897655).

In Patent Literature 1, two pairs of optical interferometers opposed on a common measurement axis are used to highly accurately measure an end-to-end dimension of a measurement target (e.g. gauge block). Then, the temperature of the measurement target is changed using a temperature controller to measure the lengths at different temperature, thereby obtaining the thermal expansion due to the changed temperature to calculate the CTE.

However, such a length measurement using the optical interferometer requires a high cost for the optical interferometer. Specifically, not only the optical interferometer per se is expensive, but also reflectivity of air has to be calculated in order to calibrate the wavelength of the measurement light, which entails measurement apparatuses for environment (e.g. temperature, humidity, atmospheric pressure and carbon dioxide concentration). Thus, the cost of the entire system becomes expensive.

Further, since reflection lights from both end faces of the measurement target are used in the length measurement using the optical interferometers, the measurable length is limited to the length of the measurement target. In other words, it is difficult to apply the above method in measurement of dimensions between protrusions at a middle portion of a reference gauge having comb-shaped measurement faces (e.g. a step gauge).

In view of the above problem, a method using a coordinate measuring machine (Patent Literature 2: JP-A-2004-226369) and a method using a pinching unit and a strain gauge (Patent Literature 3: JP-A-2005-83920) have been proposed.

In the method disclosed in Patent Literature 2, a step gauge (measurement target) is disposed in a temperature-controlled chamber. Further, a probe of an external coordinate measuring machine is introduced through an opening of the temperature-controlled chamber and the length of the step gauge is measured using the probe. Then, the temperature setting inside the temperature-controlled chamber is changed to measure the length at different temperature, and the thermal expansion is calculated based on the difference in the measurement lengths before and after changing the temperature.

The length measurement using the coordinate measuring machine does not require an optical interferometer and can be performed as long as a general-purpose coordinate measuring machine is usable in the measurement environment.

Further, the dimensions between protrusions at the middle portion of the step gauge can be measured with the use of the coordinate measuring machine, so that uniformity of thermal expansivity at the middle portion can also be measured.

In the method disclosed in Patent Literature 3, a pinching unit configured to pinch desired one of protrusions of a step gauge and a strain gauge disposed on one of chips of the pinching unit in contact with the step gauge are used, where the temperature is changed while pinching a pair of end faces whose length is to be measured with the pinching unit to directly detect the thermal expansion due to the temperature change using the strain gauge.

It is not necessary to use an optical interferometer in the thermal expansion measurement using the pinching unit and the strain gauge but only simple and inexpensive components (i.e. the pinching unit and the strain gauge) are necessary. Further, the length measurement between protrusions at the middle portion of the step gauge can be performed.

It should be noted that dimension reference gauges (e.g. step gauges) of various dimensions are used in accordance with the size of the coordinate measuring machine to be tested. For instance, a nominal dimension of some of long step gauges exceeds 1.5 meters.

The above-described measurement for the CTE $\alpha$ of the dimension reference gauge is required to be usable for the high-accuracy measurement of the dimension reference gauge with a large length L.

However, the measurable length is fixed by the pinching unit in the above-described method disclosed in Patent Literature 3 and it is not possible to measure a wide variety of lengths (e.g. length of the middle portion). Further, since a pinching unit of a correspondingly large size has to be prepared for a long step gauge, applicability of the method is limited.

Further, since the output of the strain gauge contains noise components, it is difficult to extract only the CTE of the step gauge from the converted length.

In contrast, with the use of the coordinate measuring machine for the length measurement as disclosed in Patent Literature 2, lengths of various parts (e.g. the length between end faces and the length between end faces of protrusions at a middle portion) of the dimension reference gauge of various lengths can be measured, whereby the CTE can be measured based on the results of the measurements at different temperatures.

However, even when a coordinate measuring machine is used for the length measurement as in the method disclosed in Patent Literature 2, measurement accuracy may be deteriorated when the above-described large step gauge with the length of 1.5 m or more is measured.

Specifically, a coordinate measuring machine involves a maximum permissible length measurement error (an index of measurement performance of the coordinate measuring machine). The maximum permissible length measurement error is usually given in a form of a linear expression and becomes larger in proportion to the length to be measured, which means that the larger the length to be measured becomes, the lower the accuracy becomes. A CTE of a long step gauge is difficult to be measured with a high accuracy for the above reason.

Further, some of the dimension reference gauges (e.g. a step gauge) use a section length at a middle portion thereof as a reference length, in addition to the entire length (i.e. an end-to-end distance) thereof. For instance, the section length of the step gauge is defined between end faces of two of the linearly arranged plurality of protrusions at a middle portion.

In order to define a highly accurate reference length as the section length at the middle portion, it is necessary to know a local CTE for the section length.

The CTE in the dimension reference gauge such as a step gauge usually refers to a value obtained by: dividing a thermal deformation over the entire length of the dimension reference gauge by the entire length; and further dividing the obtained deformation per length by a temperature variation before and after the thermal deformation, which is a sort of representative value. However, the CTE sometimes is not even over the entire length in an actual step gauge. For instance, a part of the step gauge in a drawing direction may have high or low CTE. Accordingly, when the section length of the middle portion as described above is defined, it is possible that the CTE of the section is not equal to the CTE (i.e. a representative value) and thus the accuracy of the section length at the middle portion as a dimension reference cannot be ensured.

Accordingly, in order to perform a highly accurate temperature correction in section(s) other than the middle portion in the dimension reference gauge such as a step gauge, it is necessary to measure the CTE for each of the section length(s) at the middle portion to be used as a dimension reference. For the above purpose, the above-described length measurement between the protrusions at the middle portion of the step gauge is of great importance.

Accordingly, it is necessary to house a reference gauge corresponding to a length to be measured in a temperature-controlled chamber together with a measurement target and to set an inside of the temperature-controlled chamber at a predetermined temperature condition. However, when a multiple of intermediate section lengths are defined for the measurement target, corresponding number of reference gauges are required. In addition, complicated processes of exchanging the reference gauge in the temperature-controlled chamber and then setting the temperature-controlled chamber at a plurality of temperatures in order to measure each of the section lengths at the plurality of temperatures are required.

It takes approximately one day in order to stabilize the temperature inside the temperature-controlled chamber at a desired temperature when the temperature-controlled chamber is once opened to exchange the reference gauge. The measurement of CTE accompanying the exchanging of the reference gauge becomes extremely complicated.

Further, in order to save the cost for the equipment and facilitate the preparation process, it is desirable to use existing gauge blocks as the reference gauge. The standard of the gauge block includes "JISB7506" and "ISO3650." In the specification of the standard, a gauge block having 0.5 mm or more and 1000 mm or less of the entire length is defined. Accordingly, the maximum length of the existing gauge block is 1000 mm. In order to measure a length exceeding the maximum length, it is necessary to prepare a dedicated gauge block with desired accuracy, or to use a plurality of the gauge blocks in combination.

Among the above, preparation of a dedicated gauge block having a length exceeding 1000 mm and a sufficient accuracy entails considerable increase in the measurement cost and thus is not applicable.

On the other hand, the combined use (tightly adhering=wringing) of a plurality of gauge blocks to provide an entire length exceeding 1000 mm is one of originally intended applications of the gauge blocks. However, when a temperature variation occurs as in the measurement of CTE, the tight adhesion of the combined gauge blocks becomes unstable. Specifically, the entire length of the combined gauge blocks may fluctuate depending on the temperature and distortion due to the temperature variation occurs on the mutually adhered faces to release the adhesion. Thus, it has been difficult to use the combined plurality of gauge blocks as a reference gauge for measuring the CTE.

As described above, there are various difficulties in the measurement of the CTE over the entire length of a long dimension reference gauge having a length exceeding a length of a reference gauge, whose solution has been desired.

SUMMARY OF THE INVENTION

An object of the invention is to provide a coefficient-of-thermal-expansion (CTE) measurement method and a measuring device for coefficient of thermal expansion (CTE measuring device) capable of highly accurately and inexpensively measuring a CTE of dimension reference gauges of various lengths.

A CTE measurement method according to an aspect of the invention is for a measurement target in a form of a dimension reference gauge, the CTE being measured for a section from a first surface to a second surface of the measurement target that are distanced in a drawing direction of the measurement target, the method including: providing: a reference gauge including a first reference surface and a second reference surface each corresponding to the first surface and the second surface, a length from the first reference surface to the second reference surface being known; a temperature-controlled chamber configured to adjust an interior temperature thereof and to house the measurement target and the reference gauge, the temperature-controlled chamber including a measurement surface provided with a measurement aperture; a measurement target support base placed in an inside of the temperature-controlled chamber and configured to support the measurement target; a reference gauge support base placed in the inside of the temperature-controlled chamber and configured to support the reference gauge; and a coordinate measuring machine including a measurement probe that is introducible into the inside of the temperature-controlled chamber through the measurement aperture; the method further including: supporting the measurement target and the reference gauge in parallel in the inside of the temperature-controlled chamber; with the interior temperature of the temperature-controlled chamber being set at a first temperature, performing a first relative measurement of a length from the first surface to the second surface with reference to the length from the first reference surface to the second reference surface; with the interior temperature of the temperature-controlled chamber being set at a second temperature, performing a second relative measurement of the length from the first surface to the second surface with reference to the length from the first reference surface to the second reference surface; and calculating the CTE of the measurement target based on the length from the first surface to the second surface at the first temperature and the length from the first surface to the second surface at the second temperature.

According to the above aspect of the invention, since the length of the measurement target is measured using the coordinate measuring machine, the CTE of the dimension reference gauges of various lengths can be highly accurately measured without using an expensive optical interferometer.

At this time, the length from the first surface to the second surface is defined as the length of the measurement target to be measured. Thus, the length of the measurement target and the CTE between the first surface and the second surface of the measurement target can be measured by defining both end faces of the measurement target as the first surface and the second surface. Alternatively, when the first surface and the second surface are defined at end faces of a protrusion at a middle portion of the measurement target, the length and the CTE of the middle portion can be measured.

Further, the reference gauge is used in the above aspect of the invention as a length master and the relative measurement of the length with respect to the reference gauge is performed in measuring the length of the measurement target using the coordinate measuring machine. Accordingly, the results of the length measurement are not dependent on the accuracy of the scale of the coordinate measuring machine but are solely dependent on the accuracy of the reference gauge. Thus, high accuracy of the measurement results can be ensured even when the length of the measurement target is increased.

Specifically, when a short measurement target is subjected to the relative measurement of length in the above aspect of the invention, a correspondingly short reference gauge is used. On the other hand, when a long measurement target is subjected to the relative measurement of length, a correspondingly long reference gauge is used.

Then, the length of the reference gauge (the distance between the first reference surface and the second reference surface) and the length of the measurement target (the distance between the first surface and the second surface) are measured using the coordinate measuring machine, and the difference between the measured length of the reference gauge and the measured length of the measurement target is added to the known reference length of the reference gauge to calculate the length of the measurement target.

In other words, it is only necessary for the coordinate measuring machine to be capable of measuring the difference between the length of the reference gauge and the length of the measurement target (specifically, the distance between the first reference surface and the second reference surface and the distance between the first surface and the second surface).

Accordingly, even when a length of a long measurement target is measured by the relative measurement, the accuracy of the measurement is not influenced by the maximum permissible length measurement error (one of performance indexes of the coordinate measuring machine).

As described above, the CTE measurement method of a dimension reference gauge according to the above aspect of the invention is capable of highly accurately and inexpensively measuring a CTE of dimension reference gauges of various lengths.

The CTE measurement method of a dimension reference gauge according to the above aspect of the invention preferably includes: in performing the first and second relative measurements, determining a coordinate system of the measurement target and the reference gauge, the determining of the coordinate system including a calculation of center coordinates of the first reference surface, the second reference surface, the first surface and the second surface, and a calculation of an inclination of the reference gauge and the measurement target with respect to the drawing direction.

According to the above arrangement, the coordinate system as a standard of the length measurement of the reference gauge and the measurement target can be determined when the relative measurement of the measurement target is performed.

Specifically, even when the first reference surface and the second reference surface of the reference gauge, and the first surface and the second surface of the measurement target are inclined with respect to the drawing direction, the detected position by the coordinate measuring machine can be corrected based on the distance between the contact point of the coordinate measuring machine and the center coordinates on the surfaces and the inclinations of the surfaces.

Further, since the coordinate system of each of the reference gauge and the measurement target is determined based on the current condition of the reference gauge and the measurement target and the length measurement is performed under the coordinate system, the accuracy of the length measurement can be enhanced and, consequently, the accuracy of the relative measurement can be kept at a high level.

In the CTE measurement method of a dimension reference gauge according to the above aspect of the invention, it is preferable that the reference gauge support base is configured to support the reference gauge between the measurement target and the measurement aperture.

The measurement target may face the measurement aperture of the measurement target at an upper face or a lateral face of the measurement target.

According to the above arrangement, the first surface and the second surface (i.e. the measurement target portion of the measurement target) are defined near the measurement aperture and the reference gauge is also disposed near the measurement aperture, so that the first reference surface and the second reference surface (i.e. comparison target) can be disposed close to the first surface and the second surface, thereby improving the measurement accuracy and the efficiency and speed of the measurement operations.

In the CTE measurement method of a dimension reference gauge according to the above aspect of the invention, it is preferable that a length of the reference gauge in the drawing direction is shorter than a length of the measurement target in the drawing direction by a predetermined dimension.

The predetermined length should be long enough to ensure a space for the probe of the coordinate measuring machine to touch the surface of the measurement target facing the measurement aperture and near the first surface or the second surface. For instance, when the measurement target in a form of a step gauge having a plurality of protrusions is used, the reference gauge may be shorter than the length of the step gauge by the length of one of the protrusions.

According to the above arrangement, since the reference gauge is provided between the measurement target and the measurement aperture, the surface of the measurement target oriented to the measurement aperture is shielded with the reference gauge. However, the surface of the measurement target is exposed near an end of the measurement target for the shorter length of the reference gauge.

Accordingly, the probe of the coordinate measuring machine is brought into contact with the exposed surface at the end of the measurement target in determining the coordinate system as described above, so that the surface of measurement target can be detected without causing any interference with the reference gauge.

In the CTE measurement method of a dimension reference gauge according to the above aspect of the invention, it is preferable that, when the first and second relative measurements are performed, the first reference surface and the first surface are coplanarly arranged or the second reference surface and the second surface are coplanarly arranged.

According to the above arrangement, when the length of the reference gauge is shorter than the length of the measurement target by the predetermined length as described above, the difference in the lengths of the reference gauge and the measurement target is maximized at the end opposite the coplanarly arranged end, thereby maximizing the margin for the surface detection using the probe of the coordinate measuring machine.

In the CTE measurement method of a dimension reference gauge according to the above aspect of the invention, it is preferable that: the measurement target support base includes a first measurement target support base and a second measurement target support base, the first measurement target support base and the second measurement target support base are configured to restrict a displacement of the measurement target in two directions intersecting the drawing direction and to permit a rotation of the measurement target around axes in the two directions intersecting the drawing direction, one of the first measurement target support base and the second measurement target support base is configured to restrict a displacement of the measurement target in the drawing direction and the other of the first measurement target support base and the second measurement target support base is configured to permit the displacement of the measurement target in the drawing direction, one of the first measurement target support base and the second measurement target support base is configured to restrict a rotation of the measurement target around an axis in the drawing direction and the other one of the first measurement target support base and the second measurement target support base is configured to permit the rotation of the measurement target around the axis in the drawing direction, the reference gauge support base includes a first reference gauge support base and a second reference gauge support base, the first reference gauge support base and the second reference gauge support base are configured to restrict a displacement of the reference gauge in the two directions intersecting the drawing direction and to permit a rotation of the reference gauge around axes in the two directions intersecting the drawing direction, one of the first reference gauge support base and the second reference gauge support base is configured to restrict a displacement of the reference gauge in the drawing direction and the other of the first reference gauge support base and the second reference gauge support base is configured to permit the displacement of the reference gauge in the drawing direction, and one of the first reference gauge support base and the second reference gauge support base is configured to restrict a rotation of the reference gauge around an axis in the drawing direction and the other of the first reference gauge support base and the second reference gauge support base is configured to permit a rotation of the reference gauge around an axis in the drawing direction.

According to the above aspect of the invention, since the displacements of the measurement target and the reference gauge in the drawing directions are restricted (i.e. positioned) at one of the first and second supports and are permitted at the other one of the first and second supports, the relative measurement of the lengths of the measurement target and the reference gauge in the drawing direction can be accurately performed. Further, since the rotation around the axis in the drawing direction is restricted and the rotations around the axes in the other directions are permitted by one of the first and second supports, possible flexure deformation of the measurement target and the reference gauge can be absorbed.

The measurement target support base and the reference gauge support base in the above aspect of the invention can respond to free expansion and attitude change of the measurement target and the reference gauge and can keep the measurement target and the reference gauge at a desired condition where the drawing directions of the measurement target and the reference gauge are mutually parallel.

In the CTE measurement method of a dimension reference gauge according to the above aspect of the invention, it is preferable that the first measurement target support base includes one or two of a conical-hole-sphere contact portion, a plane-sphere contact portion and a V-shaped-groove-sphere contact portion in contact with a bottom face of the measurement target, and the second measurement target support base includes at least one of the conical-hole-sphere contact portion, the plane-sphere contact portion and the V-shaped-groove-sphere contact portion in contact with the bottom face of the measurement target that is not provided to the first measurement target support base.

According to the above arrangement, the measurement target support base including the first measurement target support base and the second measurement target support base defines a three-point kinematic mount including the conical-hole-sphere contact portion, the plane-sphere contact portion and the V-shaped-groove-sphere contact portion in contact with the bottom face of the measurement target block, so that the displacement and rotation in the drawing direction and directions intersecting the drawing direction can be appropriately restricted.

In the CTE measurement method of a dimension reference gauge according to the above aspect of the invention, it is preferable that the first measurement target support base includes one of a conical-hole-sphere contact portion and a plane-sphere contact portion in contact with a bottom face of the measurement target, and the second measurement target support base includes the other one of the conical-hole-sphere contact portion and the plane-sphere contact portion in contact with the bottom face of the measurement target, and one of the first measurement target support base and the second measurement target support base includes a sphere contact portion in contact with one of lateral faces of the measurement target and a pressing unit that is configured to press the one of lateral faces of the measurement target against the sphere contact portion.

In the above arrangement, since the combination of the contact portion with the lateral face of the measurement target and the pressing unit in the first measurement target support base or the second measurement target support base restricts the displacement of the measurement target in the two directions intersecting the drawing direction while permitting the displacement in the drawing direction, the combination of the contact portion and the pressing unit provides a function corresponding to that of a combination of a V-shaped groove and a sphere formed at the bottom face of the measurement target. As a result, the function corresponding to the kinematic mount can be obtained in the first measurement target support base and the second measurement target support base, so that the displacement and rotation in the drawing direction and directions intersecting the drawing direction can be appropriately restricted.

In the CTE measurement method of a dimension reference gauge according to the above aspect of the invention, it is preferable that the first reference gauge support base includes one or two of a conical-hole-sphere contact portion, a plane-sphere contact portion and a V-shaped-groove-sphere contact portion in contact with a bottom face of the reference gauge, and the second reference gauge support base includes at least one of the conical-hole-sphere contact portion, the plane-sphere contact portion and the V-shaped-groove-sphere contact portion in contact with the bottom face of the reference gauge that is not provided to the first reference gauge support base.

According to the above arrangement, the reference gauge support base including the first reference gauge support base and the second reference gauge support base defines a three-point kinematic mount including the conical-hole-sphere contact portion, the plane-sphere contact portion and the V-shaped-groove-sphere contact portion in contact with the bottom face of the reference gauge, so that the displacement and rotation in the drawing direction and directions intersecting the drawing direction can be appropriately restricted.

In the CTE measurement method of a dimension reference gauge according to the above aspect of the invention, it is preferable that the first reference gauge support base includes one of a conical-hole-sphere contact portion and a plane-sphere contact portion in contact with a bottom face of the measurement target, the second reference gauge support base includes the other one of the conical-hole-sphere contact portion and the plane-sphere contact portion in contact with the bottom face of the measurement target, and one of the first reference gauge support base and the second reference gauge support base includes a sphere contact portion in contact with one of lateral faces of the reference gauge and a pressing unit that is configured to press the one of lateral faces of the reference gauge against the sphere contact portion.

In the above arrangement, since the combination of the pressing unit with the lateral face of the reference gauge in the first reference gauge support base or the second reference gauge support base restricts the displacement of the reference gauge in two directions intersecting the drawing direction while permitting the displacement in the drawing direction, the combination of the pressing unit with the lateral face of the reference gauge provides a function corresponding to that of a combination of a V-shaped groove and a sphere formed at the bottom face of the reference gauge. As a result, the function corresponding to the above-described kinematic mount can be obtained in the first reference gauge support base and the second reference gauge support base, so that the displacement and rotation in the drawing direction and directions intersecting the drawing direction can be appropriately restricted.

In the CTE measurement method of a dimension reference gauge according to the above aspect of the invention, it is preferable that a support adapter attached to the reference gauge and configured to be supported by the reference gauge support base, or a support adapter attached to the measurement target and configured to be supported by the measurement target support base is used.

According to the above arrangement, it is only necessary to form the conical hole, the V-shaped groove and the like on the support adapter in order to achieve the support using the above-described kinematic mount (i.e. it is not necessary to directly provide the conical hole and the like on the reference gauge or the measurement target), so that the support by the kinematic mount can be easily achieved.

In the CTE measurement method of a dimension reference gauge according to the above aspect of the invention, it is preferable that a preloading unit configured to downwardly preload the reference gauge is provided.

According to the above arrangement, even when the reference gauge is of a light weight, the downward preloading stabilizes the support by the reference gauge support base.

It should be noted that the measurement target is typically heavier than the reference gauge and thus the preloading is usually not necessary. However, when the measurement target is of a light weight, similar preloading may be applied.

A CTE measurement method according to another aspect of the invention is for a measurement target in a form of a dimension reference gauge, the CTE being measured for a plurality of measurement sections defined by a plurality of pairs of a measurement start point and a measurement end point of the measurement target that are distanced in a drawing direction of the measurement target, the method including: providing: a reference gauge including a plurality of pairs of reference start points and reference end points that define a plurality of reference sections corresponding to the plurality of measurement sections, a length of each of the reference sections being known; a temperature-controlled chamber configured to adjust an interior temperature thereof and to house the measurement target and the reference gauge, the temperature-controlled chamber including a measurement surface provided with a measurement aperture; and a coordinate measuring machine including a measurement probe that is introducible into an inside of the temperature-controlled chamber through the measurement aperture; supporting the measurement target and the reference gauge in parallel in the inside of the temperature-controlled chamber; with the interior temperature of the temperature-controlled chamber being set at a first temperature, detecting positions of the measurement start points, the measurement end points, the reference start points and the reference end points using the measurement probe; performing a first relative measurement for a length of each of the plurality of the measurement sections based on a length of corresponding one of the reference sections; with the interior temperature of the temperature-controlled chamber being set at a second temperature, detecting positions of the measurement start points, the measurement end points, the reference start points and the reference end points using the measurement probe; performing a second relative measurement for the length of each of the plurality of the measurement sections based on the length of corresponding one of the reference sections; and calculating the CTE of each of the plurality of the measurement sections based on the measured length at the first temperature and the measured length at the second temperature.

According to the above aspect of the invention, the CTE of each of the sections at the middle portion of the dimension reference gauge can be efficiently measured by calculating the CTE for each of the plurality of measurement sections based on the measured length at the first temperature and the measured length at the second temperature.

According to the above aspect of the invention, since the length of the measurement target is measured using the coordinate measuring machine, the CTE of the dimension reference gauges of various lengths can be highly accurately measured without using an expensive optical interferometer.

Further, according to the above aspect of the invention, the reference gauge is used as a length master and the relative measurement of the length with respect to the reference gauge is performed in measuring the length of the measurement target using the coordinate measuring machine. Accordingly, the results of the length measurement are not dependent on the accuracy of the scale of the coordinate measuring machine but are solely dependent on the accuracy of the repetition. Thus, high accuracy of the measurement results can be ensured even when the length of the measurement target is increased. It should be noted that the reference gauge is made of a material of extremely low expansivity or zero expansivity, or a material whose accurate expansivity is known.

In the above aspect of the invention, since both of the reference gauge and the measurement target are housed in the temperature-controlled chamber, it is only necessary to open/close the measurement aperture of the temperature-controlled chamber to introduce/take out the measurement probe in performing the relative measurement of the length of the measurement sections using the coordinate measuring machine. In other words, it is not necessary to open the temperature-controlled chamber in order to exchange or take in/out the reference gauge during the time period from the relative measurement of each of the measurement sections at the first temperature to the relative measurement of each of the measurement sections at the second temperature, so that the change in the temperature inside the temperature-controlled chamber as well as the measurement time can be minimized.

As described above, the CTE measurement method of a dimension reference gauge according to the above aspect of the invention is capable of highly accurately and inexpensively measuring a CTE of dimension reference gauges of various lengths and the CTE of each of the sections at the middle portion of the dimension reference gauge can be efficiently measured.

In an exemplary embodiment of the invention, a first measurement section, a second measurement section and a third measurement section may be defined on the measurement target. The first measurement section is defined by a pair of a first measurement start point and a first measurement end point and the second and third measurement sections are similarly defined respectively by a pair of a second measurement start point and a second measurement end point and a pair of a third measurement start point and a third measurement end point.

In order to measure the above measurement target, the reference gauge may be defined with first to third reference sections respectively corresponding to the first to third measurement sections, where the first reference section is defined by a pair of a first reference start point and a first reference end point and, similarly, the second and third reference sections are respectively defined by a pair of a second reference start point and a second reference end point and a pair of a third reference start point and a third reference end point.

According to the above arrangement, the lengths of the first to third measurement sections of the measurement target can be measured by sequentially performing relative measurements with respect to the first to third reference sections of the reference gauge at each of the first and second temperatures. When the length of each of the measurement sections at each of the first and second temperatures are obtained, the CTE of each of the measurement sections, i.e. first to third CTEs can be obtained based on the difference in the lengths of the first to third measurement sections at the first temperature and the lengths of the first to third measurement sections at the second temperature, and the temperature difference between the first temperature and the second temperature.

Though the first to third measurement sections and the corresponding first to third reference sections may be defined so that the positions of the corresponding start and end points in the drawing direction (and consequently the lengths of the sections) are completely identical, the start and end points in the drawing direction may be at different positions to define different lengths for the measurement sections. However, the difference in the length between each of the corresponding measurement sections and the reference sections is preferably 10 mm or less.

In the above arrangement, the numbers of the measurement sections and the reference sections are not limited to three (i.e. the first to third) but may be two (i.e. first and second) or more than three.

In an aspect of the invention, the dimension reference gauge as the measurement target is exemplarily a step gauge. The plurality of measurement sections may be defined between start points and end points defined on surfaces of a plurality of protrusions arranged on the step gauge.

However, the measurement target of the invention is not restricted to the step gauge but may alternatively be other dimension reference gauge that is configured to define a plurality of length references in a drawing direction.

In the CTE measurement method of a dimension reference gauge according to the above aspect of the invention, it is preferable that each of the reference start points and the reference end points of the reference gauge are defined by one of: a point on a surface of a protrusion provided on the reference gauge intersecting the drawing direction; a virtual point on a central axis of a cylindrical hole to be detected provided to the reference gauge, the virtual point being obtained by detecting an inner circumferential surface of the hole to be detected using the coordinate measuring machine; a virtual point on a central axis of a cylindrical cylinder to be measured provided to the reference gauge, the virtual point being obtained by detecting an outer circumferential surface of the cylinder to be measured using the coordinate measuring machine; and a virtual point indicating a center of a ball to be measured provided to the reference gauge, the virtual point being obtained by detecting an outer circumferential surface of the ball to be measured using the coordinate measuring machine.

According to the above arrangement, the substantive reference start point and reference end point can be defined on the surface of the protrusion formed on the reference gauge. The reference gauge having the protrusion is, for instance, a step gauge. Further, the substantive reference start point and reference end point may be formed on both end faces of the reference gauge.

In the above arrangement, the reference start point and the reference end point are not necessarily defined as substantive points but virtual reference start point and reference end point may be defined by forming a hole to be detected having a cylindrical inner circumferential surface on a reference gauge or arranging a cylinder to be measured or a ball to be measured on the reference gauge, and performing a contact measurement at three or more points on the surface of the hole to be detected, cylinder to be measured or ball to be measured using a coordinate measuring machine. With such an arrangement, the reference gauge can be easily produced by machining the hole to be detected on a single elongated reference gauge body or fixing the cylinder to be measured or the ball to be measured on the single elongated reference gauge body.

In the CTE measurement method of a dimension reference gauge according to the above aspect of the invention, it is preferable that the reference gauge is in a form of a combination of a plurality of gauge blocks corresponding to the reference sections, end faces of the gauge blocks defining the reference start points and the reference end points.

According to the above arrangement, the reference gauge can be constructed by combining the plurality of existing gauge blocks. Since the plurality of gauge blocks each define a reference section between a reference start point and a reference end point defined on each of the end faces of the gauge blocks, the reference sections of a plurality of lengths can be defined when the gauge blocks are combined. Thus, the reference gauge having the reference sections with the plurality of lengths can be easily and inexpensively produced.

It should be noted that the plurality of gauge blocks are layered in a descending order of the entire length thereof. A shorter one of the gauge blocks fixed on the other (longer) one of the gauge blocks defines the above-described "protrusion formed on the reference gauge."

In order to fix the combined plurality of gauge blocks, a member wrapping the combined gauge blocks, a member penetrating the gauge blocks or an adhesive for bonding the gauge blocks may be used.

The reference start points of two or more of the plurality of gauge blocks may be coplanarly arranged so that the difference in the length of the gauge blocks may appear solely on an opposite end or, alternatively, the ends may be shifted with each other so that the difference in the length of the block gauges appears on both ends of the block gauge(s).

In the CTE measurement method of a dimension reference gauge according to the above aspect of the invention, it is preferable that the reference gauge includes an insert hole at a position corresponding to at least one of the measurement start points and the measurement end points of the measurement target, the measurement probe of the coordinate measuring machine being insertable through the insert hole.

According to the above arrangement, even when the reference gauge is arranged along a side of the measurement target at which the measurement start point and the measurement end point are defined, the positions of the measurement start point and the measurement end point can be detected by introducing the measurement probe through the insert hole.

It should be noted that the cylindrical hole to be detected formed in the reference gauge may be used as the insert hole.

A CTE measurement method according to still another aspect of the invention is for a measurement target in a form of a dimension reference gauge, a CTE of a measurement target section of the measurement target being measured in the method, the method including: providing: a reference gauge having a known reference gauge length that is shorter than a length of the measurement target section; a temperature-controlled chamber configured to adjust an interior temperature thereof and to house the measurement target and the reference gauge, the temperature-controlled chamber including a measurement surface provided with a measurement aperture; and a coordinate measuring machine including a measurement probe that is introducible into an inside of the temperature-controlled chamber through the measurement aperture; allocating a plurality of relative measurement sections each having a length corresponding to the reference gauge length to the measurement target section, each of the plurality of relative measurement sections being shifted by a predetermined shift amount; holding the measurement target and the reference gauge in parallel in the inside of the temperature-controlled chamber; setting the interior temperature of the temperature-controlled chamber at a first temperature; sequentially performing a first relative measurement of the length of each of the plurality of relative measurement sections with reference to the reference gauge; setting the interior temperature of the temperature-controlled chamber at a second temperature; sequentially performing a second relative measurement of the length of each of the plurality of relative measurement sections with reference to the reference gauge; calculating section CTEs of the plurality of relative measurement sections based on the length obtained by the first relative measurement at the first temperature and the length obtained by the second relative measurement at the second temperature for each of the relative measurement sections; and calculating a CTE of an entirety of the measurement target section based on the calculated section CTEs of the plurality of relative measurement sections.

In the above aspect of the invention, the measurement target section may be defined by the entire length of the measurement target (i.e. between both ends of the measurement target) or, alternatively, by a section between a start point and an end point remote from the end of the measurement target (i.e. a middle portion of the measurement target). The measurement target in a form of the dimension reference gauge is exemplarily a step gauge.

In the above aspect of the invention, the reference gauge length may be defined by the entire length of the reference gauge (i.e. a distance between the ends of the reference gauge) or, alternatively, a length of a section between a start point and an end point remote from the ends of the reference gauge (i.e. a section between steps and the like formed in the middle of the reference gauge). The reference gauge is suitably provided by a gauge block whose reference gauge length is highly accurately calibrated.

The orientation of the reference gauge length is set parallel to the orientation of the measurement target section when the measurement target and the reference gauge are supported in parallel in the temperature-controlled chamber in the above aspect of the invention. When the measurement target and the reference gauge are supported, it is preferable that a support device that is configured to keep the orientations of the measurement target and the reference gauge to be constant and simultaneously permit thermal deformation of the measurement target and the reference gauge in the drawing direction thereof is used.

In the above aspect of the invention, the plurality of relative measurement sections are arranged to cover the entire measurement target section and the relative measurement of the lengths of the relative measurement sections is performed. Then, the section CTEs of the relative measurement sections are calculated based on the lengths of the relative measurement sections at the first temperature and the second temperature.

Accordingly, the relative measurement using the reference gauge for each of the relative measurement sections is achievable in the above aspect of the invention even when the length of the measurement target section is more than the length of the reference gauge.

During the relative measurement of the length of the measurement target in each of the relative measurement sections, the relative measurement with respect to the length of the reference gauge is performed using the coordinate measuring machine, so that a highly accurate measurement can be inexpensively performed without using an expensive optical interferometer.

Further, the relative measurement of the length of the measurement target is performed with respect to the reference gauge using the coordinate measuring machine. Accordingly, the results of the length measurement are not dependent on the accuracy of the scale of the coordinate measuring machine but solely dependent on the accuracy of the reference gauge. Even when the length of the measurement target section is increased, the length of each of the relative measurement sections can be set shorter than the length of the measurement target section, so that an existing gauge block can be used as the reference gauge and the production cost can be reduced.

Further, since both of the reference gauge and the measurement target are housed in the temperature-controlled chamber, it is only necessary to open/close the measurement aperture of the temperature-controlled chamber to introduce/take out the measurement probe in performing the relative measurement of the length of the measurement sections using the coordinate measuring machine.

In addition, since the reference gauge corresponding to the relative measurement sections is prepared in advance, it is not necessary to introduce/take out the reference gauge into/out of the temperature-controlled chamber during the measurement process, so that the temperature change in the temperature-controlled chamber and the measurement process time can be minimized during the measurement process.

As described above, the CTE of an entirety of a dimension reference gauge having a length exceeding the length of the reference gauge can be highly accurately and inexpensively measured in the above aspect of the invention.

In the CTE measurement method of a dimension reference gauge according to the above aspect of the invention, it is preferable that when the relative measurement sections are allocated to the measurement target section, the reference gauge is used, where the length of the measurement target section and the reference gauge length are in an integer ratio, the shift amount is defined by a difference between the length of the measurement target section and the reference gauge length divided by an integer, and an allocated number of the relative measurement sections are assigned to the measurement target section, the allocated number being defined by a number, which is larger by one than a division of the difference between the length of the measurement target section and the reference gauge length by the shift amount.

According to the above arrangement, the allocated number of the relative measurement sections mutually shifted by the shift amount cover the entirety of the measurement target section.

Then, after calculating the section CTE of each of the relative measurement sections, a calculation process of the CTE of each of the relative measurement sections can be performed on each of the portions of the measurement target section per sections for the shift amount, thereby enhancing the efficiency of the calculation process.

For instance, after calculating the section CTEs for respective relative measurement sections, an average of the section CTEs of the relative measurement sections partially overlapped for each of the sections can be obtained, thereby highly accurately and reliably obtaining the CTE of the entire measurement target section with the use of the section CTEs for respective relative measurement sections.

In the CTE measurement method of a dimension reference gauge according to the above aspect of the invention, it is preferable that, when the CTE of the entirety of the measurement target section is calculated: a plurality of count sections sectioned by the shift amount are allocated to the measurement target section; an average of the section CTEs of the relative measurement sections allocated to each of the count sections is calculated; a weight coefficient of each of the count sections is calculated based on a ratio of each of the count sections with respect to the length of the measurement target section; and a product of the average of the section CTEs of each of the count sections and the weight coefficient is totalized to obtain the CTE of the entirety of the measurement target section.

According to the above arrangement, the highly accurate CTE can be efficiently measured by: allocating the plurality of count sections to the measurement target section; averaging the section CTEs in each of the count sections; and totalizing the averages after applying weight coefficient of the count sections corresponding to each of the count sections.

In the CTE measurement method of a dimension reference gauge according to the above aspect of the invention, it is preferable that a reference gauge movement mechanism configured to hold the reference gauge and to move the reference gauge to each of the plurality of relative measurement sections is provided in the temperature-controlled chamber, and, when the relative measurement of the length of the plurality of relative measurement sections is performed, the reference gauge is sequentially moved to each of the relative measurement section at which the relative measurement is performed.

According to the above arrangement, the single reference gauge can be used in common to the plurality of relative measurement sections, so that fluctuation in the measurement accuracy can be prevented.

In the CTE measurement method of a dimension reference gauge according to the above aspect of the invention, it is preferable that the reference gauge includes a plurality of gauge units corresponding to the plurality of relative measurement sections, and the relative measurement of the plurality of relative measurement sections is performed based on the length of each of the relative measurement sections and corresponding one of the gauge units.

According to the above arrangement, a plurality of the relative measurement sections can be measured using the single reference gauge, so that a movement operation of the reference gauge and the like can be omitted.

The reference gauge including the plurality of gauge units may be provided by, for instance, combining gauge blocks having the reference gauge length corresponding to the length of the relative measurement section and fixing the gauge blocks while being shifted with each other by a shift amount.

In the CTE measurement method of a dimension reference gauge according to the above aspect of the invention, it is preferable that the reference gauge includes a plurality of gauge blocks each having the reference gauge length corresponding to the length of the relative measurement section, the plurality of gauge blocks being combined and fixed while the plurality of gauge blocks are shifted with each other by a shift amount, and a through hole penetrating through a top face and a bottom face is provided to a middle portion of each of the gauge blocks, an end of another one of the gauge blocks being visible through the through hole.

According to the above arrangement, even when the relative measurement section of the measurement target is located at the position shielded by the reference gauge, the measurement probe of the coordinate measuring machine can be introduced through the through hole.

In the CTE measurement method of a dimension reference gauge according to the above aspect of the invention, it is preferable that the reference gauge is made of a material of extremely low expansion coefficient or a material of zero expansion coefficient whose expansion due to a temperature change between the first temperature and the second temperature is below a detectable limit, or made of a material whose expansion coefficient is known.

According to the above arrangement, when the reference gauge is made of a material of extremely low expansion coefficient or a material of zero expansion coefficient, it is not necessary to perform temperature correction of the length of the reference gauge between the first temperature and the second temperature. On the other hand, when the reference gauge is made of a material having a known expansion coefficient, a highly accurate length of the reference gauge at the first temperature and the second temperature can be calculated through a temperature correction. Since the accurate reference gauge length at each of the temperatures can be known in any of the instances, the relative measurement at the first temperature and the relative measurement at the second temperature can be highly accurately performed.

It should be noted that the reference gauge may be provided by an existing gauge block whose high accuracy is ensured.

A CTE measuring device according to further aspect of the invention is for a measurement target in a form of a dimension reference gauge, the CTE being measured for a section from a first surface to a second surface of the measurement target that are distanced in a drawing direction of the measurement target, the CTE measuring device including: a reference gauge including a first reference surface and a second reference surface each corresponding to the first surface and the second surface, a length from the first reference surface to the second reference surface being known; a temperature-controlled chamber configured to adjust an interior temperature thereof and to house the measurement target and the reference gauge, the temperature-controlled chamber including a measurement surface provided with a measurement aperture; a measurement target support base placed in an inside of the temperature-controlled chamber and configured to support the measurement target; a reference gauge support base placed in the inside of the temperature-controlled chamber and configured to support the reference gauge; and a coordinate measuring machine including a measurement probe that is introducible into the inside of the temperature-controlled chamber through the measurement aperture.

According to the above aspect of the invention, the same effects and advantages can be obtained as those in the above-described CTE measurement method of the dimension reference gauge through the process mentioned in the CTE measurement method.

A CTE measuring device according to still further aspect of the invention is for a measurement target in a form of a dimension reference gauge, the CTE of the measurement target being measured for a plurality of measurement sections defined by a plurality of pairs of a measurement start point and a measurement end point of the measurement target that are distanced in a drawing direction of the measurement target, the CTE measuring device including: a reference gauge including a plurality of pairs of reference start points and reference end points that define a plurality of reference sections corresponding to the plurality of measurement sections, a length of each of the reference sections being known; a temperature-controlled chamber configured to adjust an interior temperature thereof and to house the measurement target and the reference gauge, the temperature-controlled chamber including a measurement surface provided with a measurement aperture; and a coordinate measuring machine including a measurement probe that is introducible into an inside of the temperature-controlled chamber through the measurement aperture.

The CTE measuring device of a dimension reference gauge according to the above aspect of the invention provides the above-described effects and advantages when being used in the above-described CTE measurement method of the dimension reference gauge.

A reference gauge according to still further aspect of the invention is for measuring a CTE of a measurement target in a form of a dimension reference gauge, the CTE of the measurement target being measured for a plurality of measurement sections defined by a plurality of pairs of a measurement start point and a measurement end point of the measurement target that are distanced in a drawing direction of the measurement target, the reference gauge including: a plurality of pairs of reference start points and reference end points that define a plurality of reference sections corresponding to the plurality of measurement sections, a length of each of the reference sections being known.

The reference gauge according to the above aspect of the invention provides the above-described effects and advantages when being used in the above-described CTE measurement method of the dimension reference gauge.

According to the above aspects of the invention, a CTE measurement method and a CTE measuring device capable of highly accurately and inexpensively measuring CTEs of dimension reference gauges of various lengths can be provided.

BRIEF DESCRIPTION OF DRAWING(S)

DESCRIPTION OF EMBODIMENT(S)

Exemplary embodiment(s) of the invention will be described below with reference to the attached drawings.

First Exemplary Embodiment

Figure 1:
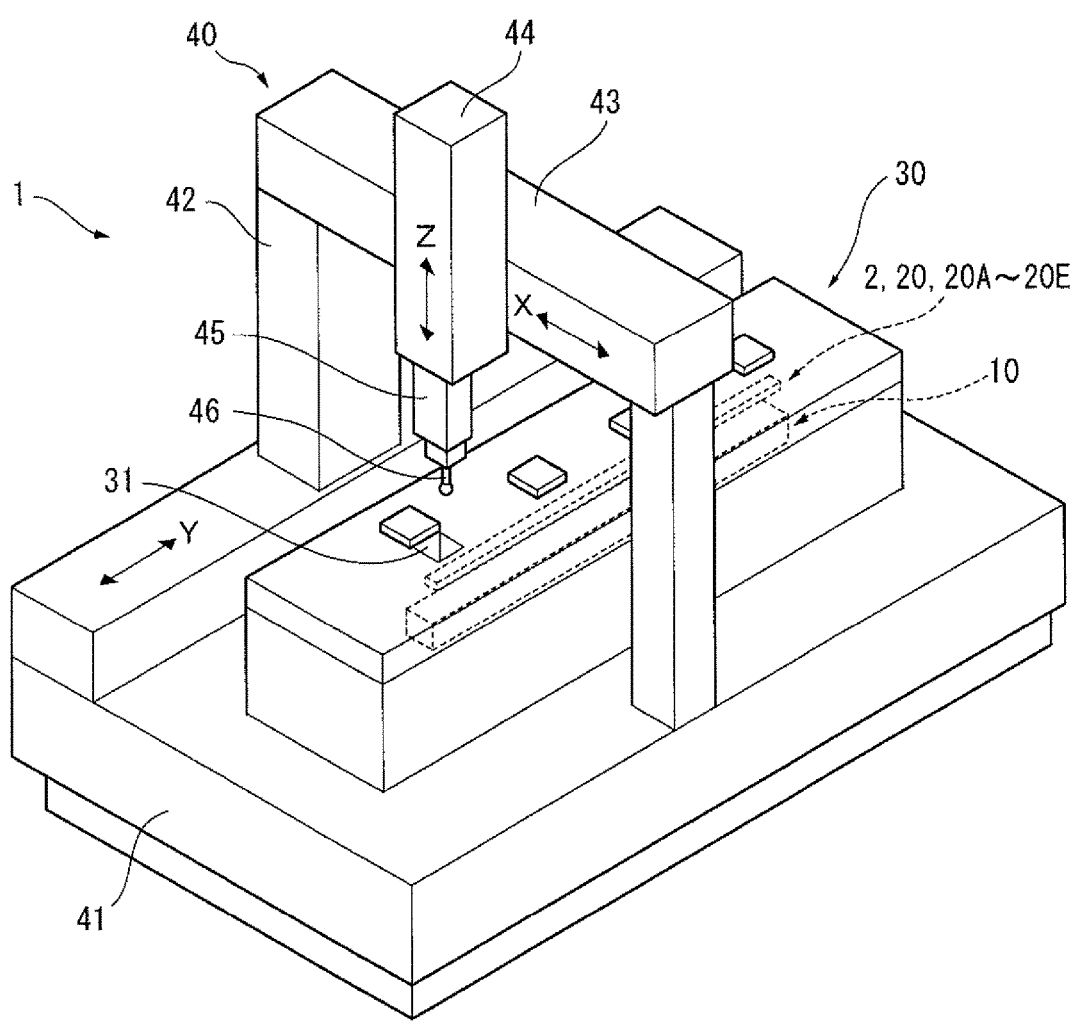
FIG. 1 is a perspective view showing a measuring device according to an aspect of the invention.

As shown in FIG. 1, a CTE (Coefficient of Thermal Expansion) measuring device 1 according to a first exemplary embodiment measures a dimension reference gauge in a form of a step gauge 10 to highly accurately measure CTE of the step gauge 10.

For the above measurement, the CTE measuring device 1 includes a temperature-controlled chamber 30 configured to house the step gauge 10 therein and keep the step gauge 10 at a predetermined temperature, a reference gauge block 2 (reference gauge) configured to be housed in the temperature-controlled chamber 30, and a coordinate measuring machine 40 configured to compare and measure a length of the step gauge 10 with reference to the reference gauge block 2.

The coordinate measuring machine 40 includes a measurement table 41. A head 44 is supported above the measurement table 41 via a column 42 and a crossbar 43. A ram 45 extending downward is provided to the head 44. A probe 46 is supported at a distal end of the ram 45.

The column 42 of the coordinate measuring machine 40 is movable in a Y-axis direction with respect to the measurement table 41. The head 44 is movable in an X-axis direction with respect to the crossbar 43. The ram 45 is movable in a Z-axis direction with respect to the head 44. The probe 46 is three-dimensionally movable with respect to the measurement table 41 using the three-axis movement.

The temperature-controlled chamber 30 is a device having a box-shaped casing and configured to keep the temperature inside the casing at a desired temperature. The temperature-controlled chamber 30 is mounted on an upper face of the measurement table 41 and fixed thereon in a manner that a longitudinal direction of the temperature-controlled chamber 30 is in the Y-axis direction.

An upper face of the temperature-controlled chamber 30 is openable and closable so as to house the step gauge 10 and the reference gauge block 2 inside the temperature-controlled chamber 30.

A plurality of measurement apertures 31 each having an openable and closable lid are provided on the upper face of the temperature-controlled chamber 30 in alignment in the Y-axis direction.

The step gauge 10 is supported inside the temperature-controlled chamber 30 so that a drawing direction Lt of the step gauge 10 extends along the Y-axis direction. The reference gauge block 2 is disposed in a manner facing an upper side of the step gauge 10 (i.e. a side of the step gauge 10 oriented to face the measurement aperture 31) and is supported so that a drawing direction Lr of the reference gauge block 2 extends along the Y-axis direction (i.e. in parallel with the step gauge 10).

Figure 2:
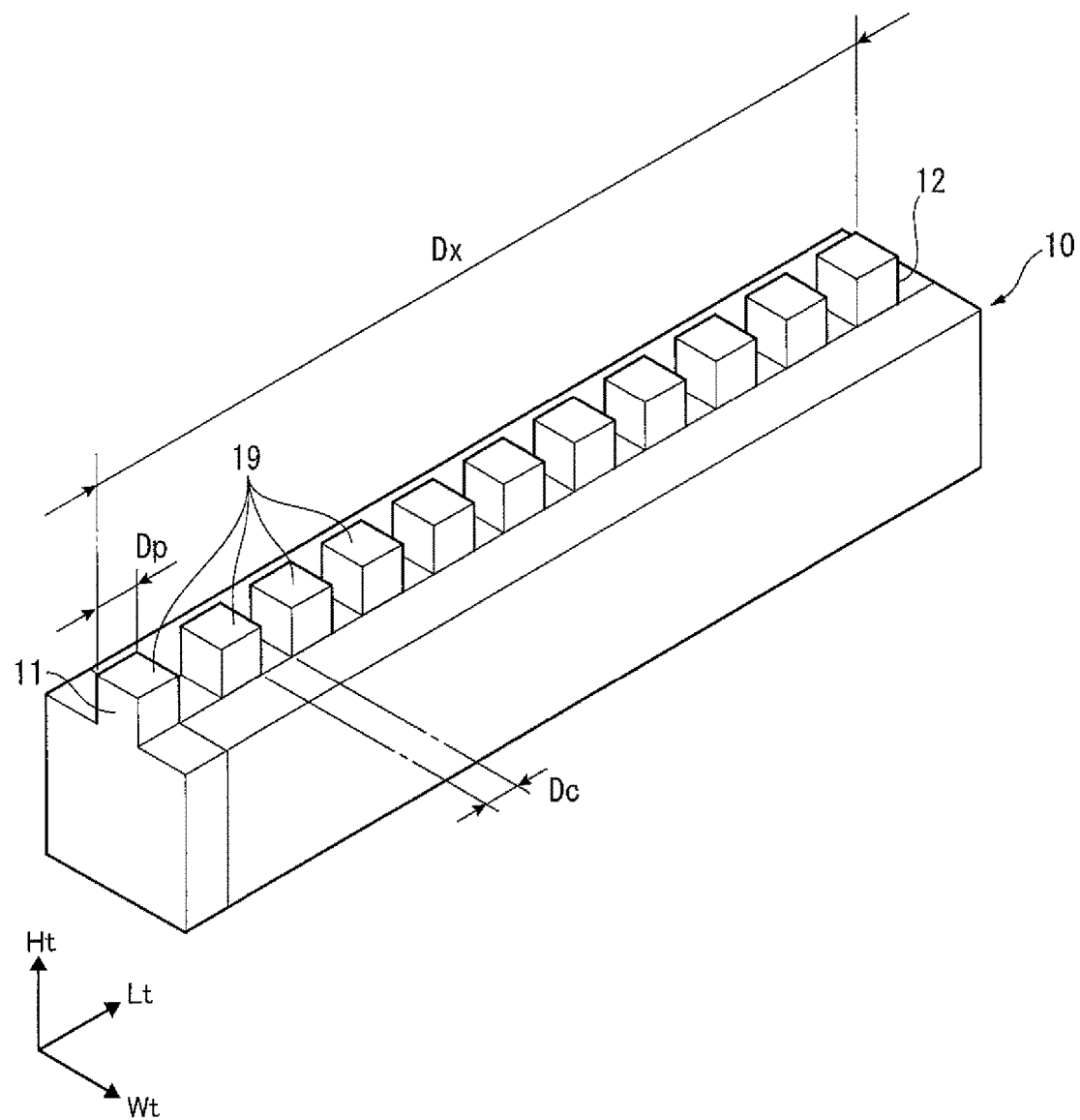
FIG. 2 is a perspective view showing a step gauge (a measurement target in a first exemplary embodiment of the invention).

As shown in FIG. 2, the step gauge 10 (the measurement target) includes a square-column body extending in the drawing direction Lt. A top face, bottom face and lateral faces of the body are parallel to one of a vertical direction Ht and width direction Wt that intersect the drawing direction Lt.

A plurality of protrusions 19 each in a form of a gauge block are provided on the upper face of the step gauge 10 in alignment in the drawing direction Lt. A length of each of the protrusions 19 in the drawing direction Lt is denoted by Dp. A dimension of a recess defined between opposing ones of the protrusions 19 in the drawing direction Lt is denoted by Dc.

In the first exemplary embodiment, a surface of one of the protrusions 19 at a first end of the step gauge 10 is denoted by a first surface 11, a surface of another one of the protrusions 19 at a second end of the step gauge 10 is denoted by a second surface 12 and a distance between the first surface 11 and the second surface 12 is measured as a length Dx of the step gauge 10.

Figure 3:
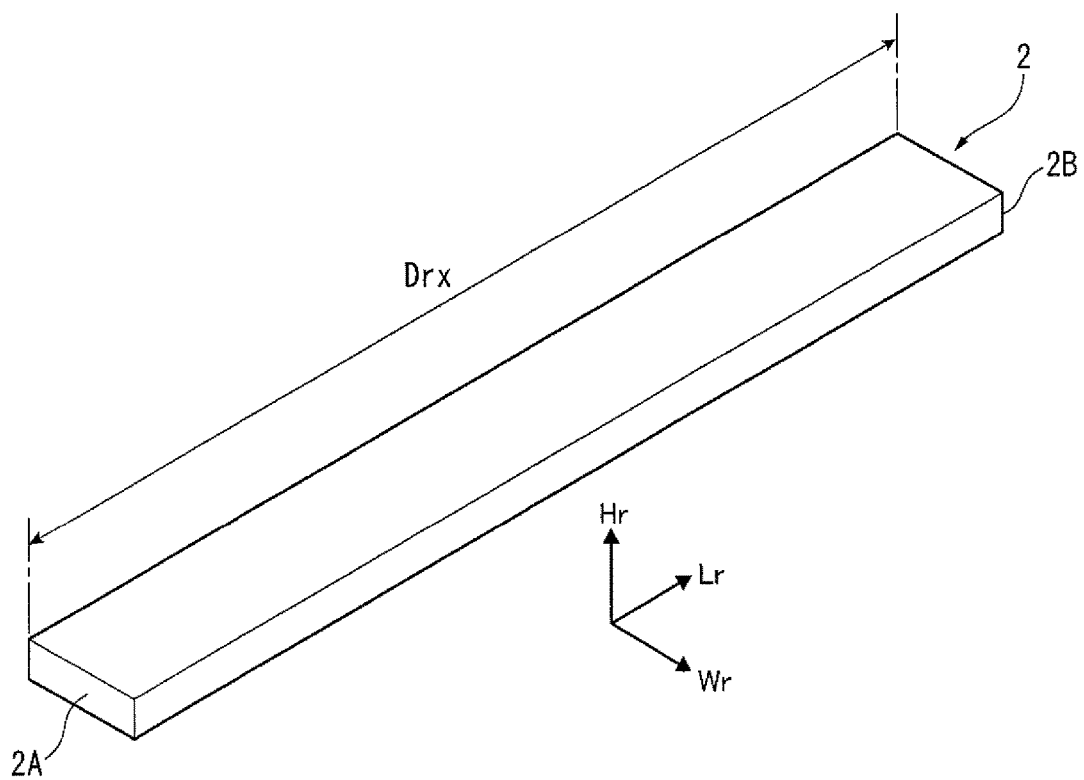
FIG. 3 is a perspective view showing a reference gauge block (a reference gauge in the first exemplary embodiment).

As shown in FIG. 3, the reference gauge block 2 (the reference gauge) is a gauge block extending in the drawing direction Lr. A top face, bottom face and lateral faces of the reference gauge block 2 are each parallel to one of a vertical direction Hr and width direction Wr that intersect the drawing direction Lr.

A first reference surface 2A and a second reference surface 2B of the reference gauge block 2 are defined by a pair of end faces at both ends in the drawing direction Lr.

A distance between the first reference surface 2A and the second reference surface 2B (i.e. a length) of the reference gauge block 2 is defined as Drx. The length Drx of the reference gauge block 2 is shorter than the to-be-measured length Dx (nominal dimension) of the step gauge 10 (i.e. the measurement target) by a predetermined dimension (e.g. a length Dp of one of the protrusions 19).

Not only the length Drx of the reference gauge block 2 is known but also the CTE of the reference gauge block 2 is highly accurately known. Accordingly, when the lengths are measured and compared at a later-described first temperature t1 and at a second temperature t2, the length Drx each of the temperatures t1, t2 can be highly accurately calculated based on the CTE.

Figure 4:
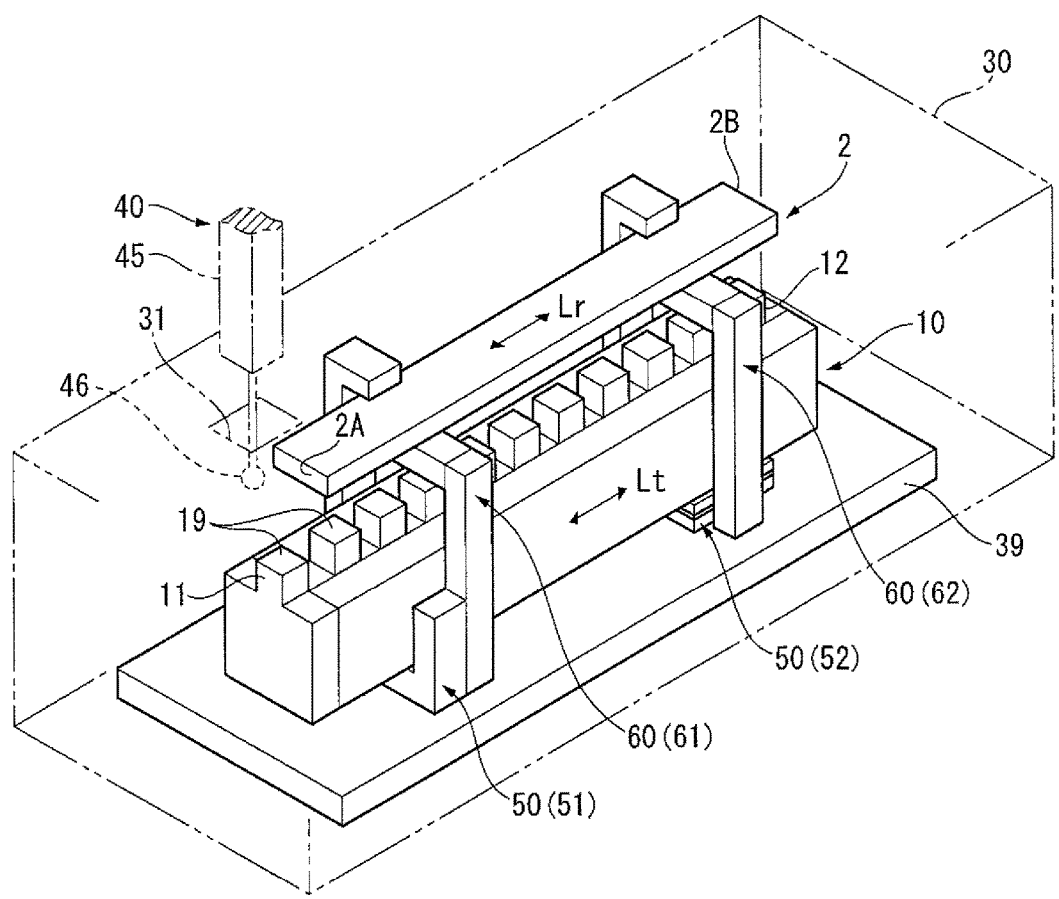
FIG. 4 is a perspective view showing an arrangement of a temperature-controlled chamber, a step gauge and a reference gauge block in the first exemplary embodiment.

As shown in FIG. 4, the step gauge 10 and the reference gauge block 2 are placed in the temperature-controlled chamber 30 in parallel with each other.

In order to support the step gauge 10 and the reference gauge block 2, a highly rigid bottom plate 39 is placed in the temperature-controlled chamber 30. A measurement target support base 50 and a reference gauge support base 60 are placed on an upper face of the bottom plate 32.

The measurement target support base 50 includes a first measurement target support base 51 near the first surface 11 and a second measurement target support base 52 near the second surface 12.

The reference gauge support base 60 includes a first reference gauge support base 61 near the first reference surface 2A and a second reference gauge support base 62 near the second reference surface 2B.

First Measurement Target Support Base 51

Figure 5:
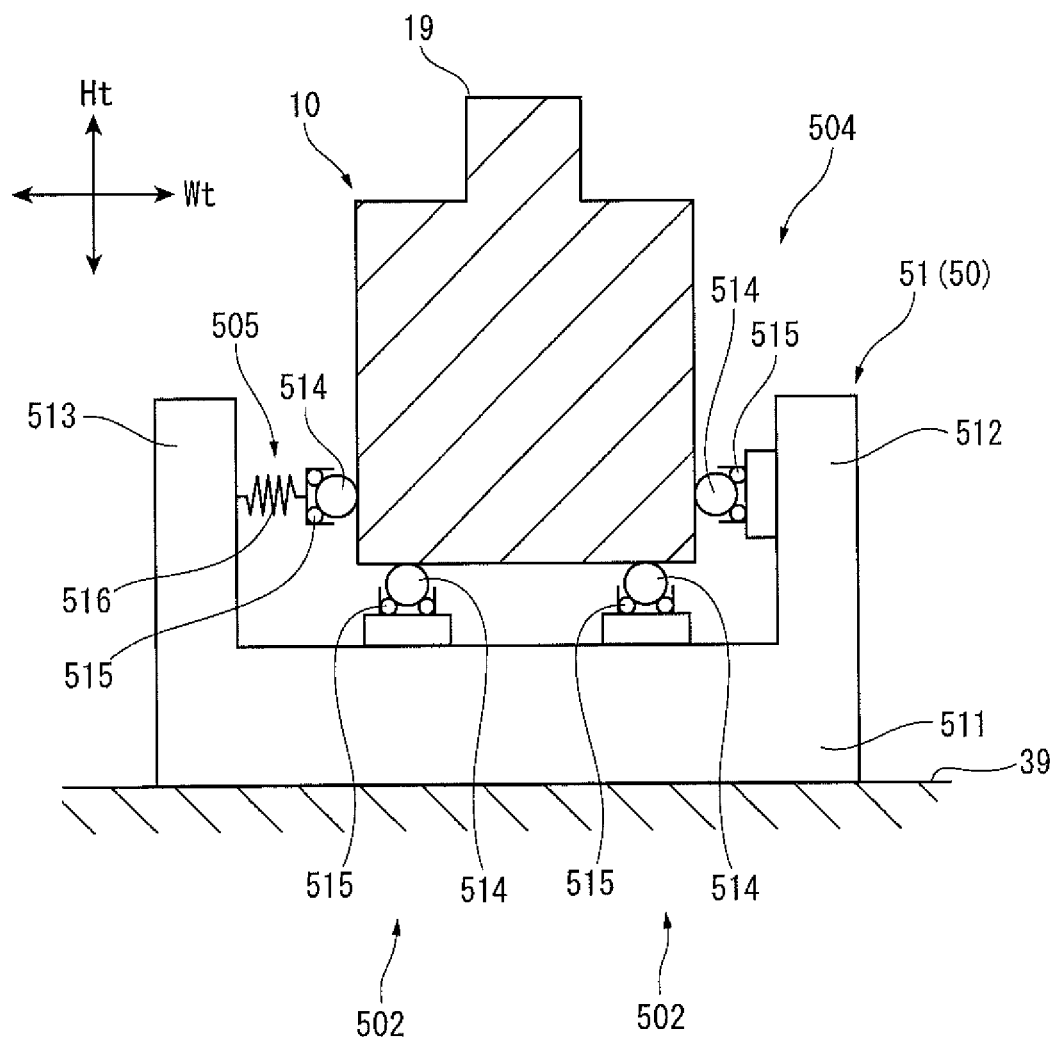
FIG. 5 is a side elevational view showing a first measurement target support base in the first exemplary embodiment.

As shown in FIG. 5, the first measurement target support base 51 includes a base 511 placed on the bottom plate 39 and upright portions 512, 513 provided alongside edges of the base 511. The step gauge 10 is received in a space between the upright portions 512, 513 and supported above the base 511.

Two pairs of balls 514 and ball holders 515 are arranged on the base 511 in alignment in the width direction Wt. Each of the ball holders 515 includes a plurality of support balls that are configured to roll on each of the balls 514, thereby defining a so-called free ball bearing or ball caster.

A bottom face of the step gauge 10 is in contact with the two balls 514. The balls 514 and the ball holders 515 define plane-sphere contact portions 502 between the first measurement target support base 51 and the bottom face of the step gauge 10.

The load of the step gauge 10 are supported by the temperature-controlled chamber 30 through the two pairs of contact portions 502, the base 511 and the bottom plate 39.

Through the rolling of the balls 514 on the bottom face of the step gauge 10 at each of the contact portions 502, the step gauge 10 is displaceable in the drawing direction Lt and the width direction Wt and is capable of rotation around an axis in the vertical direction H and an axis in the width direction Wt (i.e. yawing and pitching).

However, since the bottom face of the step gauge 10 is in contact with the balls 514, a displacement of the step gauge 10 in the vertical direction Ht is restricted. Further, since the two pairs of balls 514 are provided, rotation around an axis in the drawing direction Lt (i.e. rolling) is also restricted.

A ball 514 and a ball holder 515 similar to those of the contact portions 502 between the bottom face of the step gauge 10 and the base 511 are provided between the upright portion 512 and one of the lateral faces of the step gauge 10, thereby defining a plane-sphere contact portion 504.

A ball 514 and a ball holder 515 similar to those of the contact portions 502 between the bottom face of the step gauge 10 and the base 511 are provided between the upright portion 513 and the other one of the lateral faces of the step gauge 10. Further, a compression coil spring 516 is provided between the ball holder 515 and the upright portion 513. The ball 514, the ball holder 515 and the compression coil spring 516 define a pressing unit 505.

The step gauge 10 is biased by the pressing unit 505 along the width direction Wt and is pressed against the upright portion 512 through the contact portion 504, so that the displacement of the step gauge 10 in the width direction Wt is restricted. However, since the pressing unit 505 and the contact portion 504 are in contact with the lateral face of the step gauge 10 via the balls 514, the displacement of the step gauge 10 in the other directions are not restricted and rotation around an axis in each of the above-mentioned directions is also not restricted.

Accordingly, the first measurement target support base 51 supports the load of the step gauge 10 and restricts the displacement of the step gauge 10 along the vertical direction Ht using the two contact portions 502. The displacement of the step gauge 10 in the width direction Wt is also restricted by the contact portion 504 and the pressing unit 505, so that the orientation of the step gauge 10 in the drawing direction Lt is determined.

On the other hand, the first measurement target support base 51 permits the displacement in the drawing direction Lt as well as pitching and yawing. Thus, when the step gauge 10 is thermally deformed, extension and contraction in the drawing direction Lt are permitted.

Second Measurement Target Support Base 52

Figure 6:
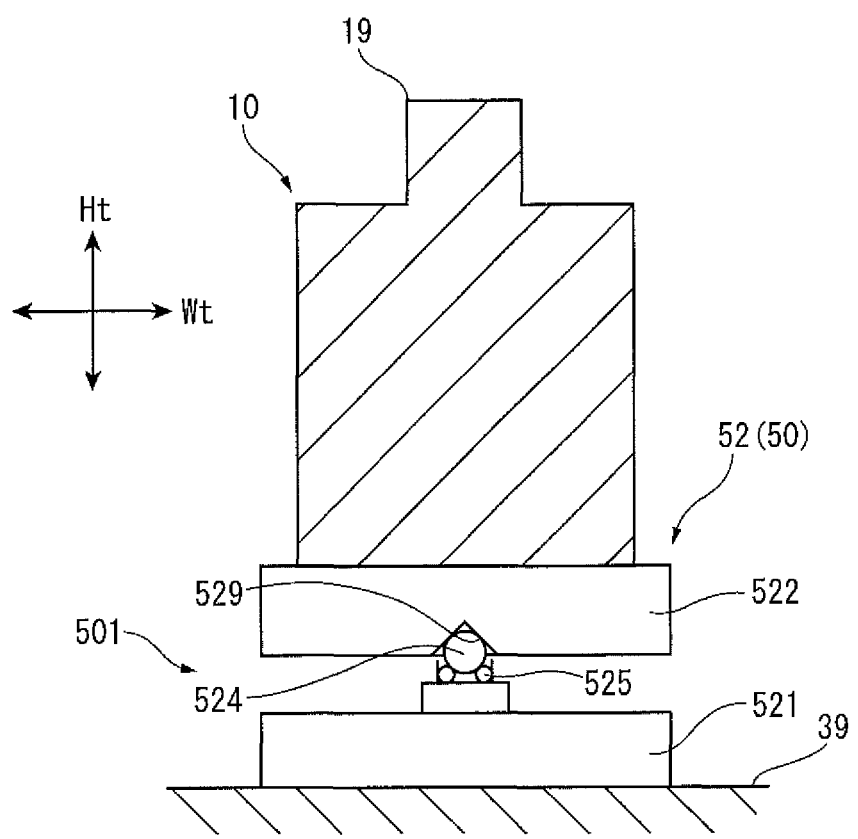
FIG. 6 is a side elevational view showing a second measurement target support base in the first exemplary embodiment.

As shown in FIG. 6, the second measurement target support base 52 includes a base 521 placed on the bottom plate 39 and support portion 522 on which the lower face of the step gauge 10 is placed.

A ball 524 and a ball holder 525 are provided on the base 521. The ball holder 525 includes a plurality of support balls that are configured to roll on the ball 524, thereby defining a so-called free ball bearing or ball caster.

A conical hole 529 is formed on a lower face of the support portion 522. The ball 524 is fitted in the conical hole 529.

The conical hole 529 and the ball 524 define a conical-hole-sphere contact portion 501.

Accordingly, the second measurement target support base 52 restricts the displacement of the step gauge 10 in all of the vertical direction Ht, the width direction Wt and the drawing direction Lt using the contact portion 501 while supporting the load of the step gauge 10 at the contact portion 501. However, the contact portion 501 permits all of a rotation (yawing) around an axis passing through the ball 524 and extending in the vertical direction Ht, a rotation (pitching) around an axis passing through the ball 524 and extending in the width direction Wt and a rotation (rolling) around an axis passing through the ball 524 and extending in the drawing direction Lt.

As described above, the step gauge 10 is supported by the first measurement target support base 51 and the second measurement target support base 52.

With the above arrangement, the step gauge 10 is supported so that the position of the step gauge 10 in the width direction Wt is restricted by each of the first measurement target support base 51 and the second measurement target support base 52 and the drawing direction Lt of the step gauge 10 is aligned with the Y-axis direction of the temperature-controlled chamber 30 and the coordinate measuring machine 40.

Further, though the position of the step gauge 10 in the drawing direction Lt is restricted by the contact portion 501 of the second measurement target support base 52, the displacement of the step gauge 10 in the drawing direction Lt is permitted by the first measurement target support base 51, so that the extension/contraction due to thermal deformation mainly appears on the side of the first surface 11.

First Reference Gauge Support Base 61

Figure 7:
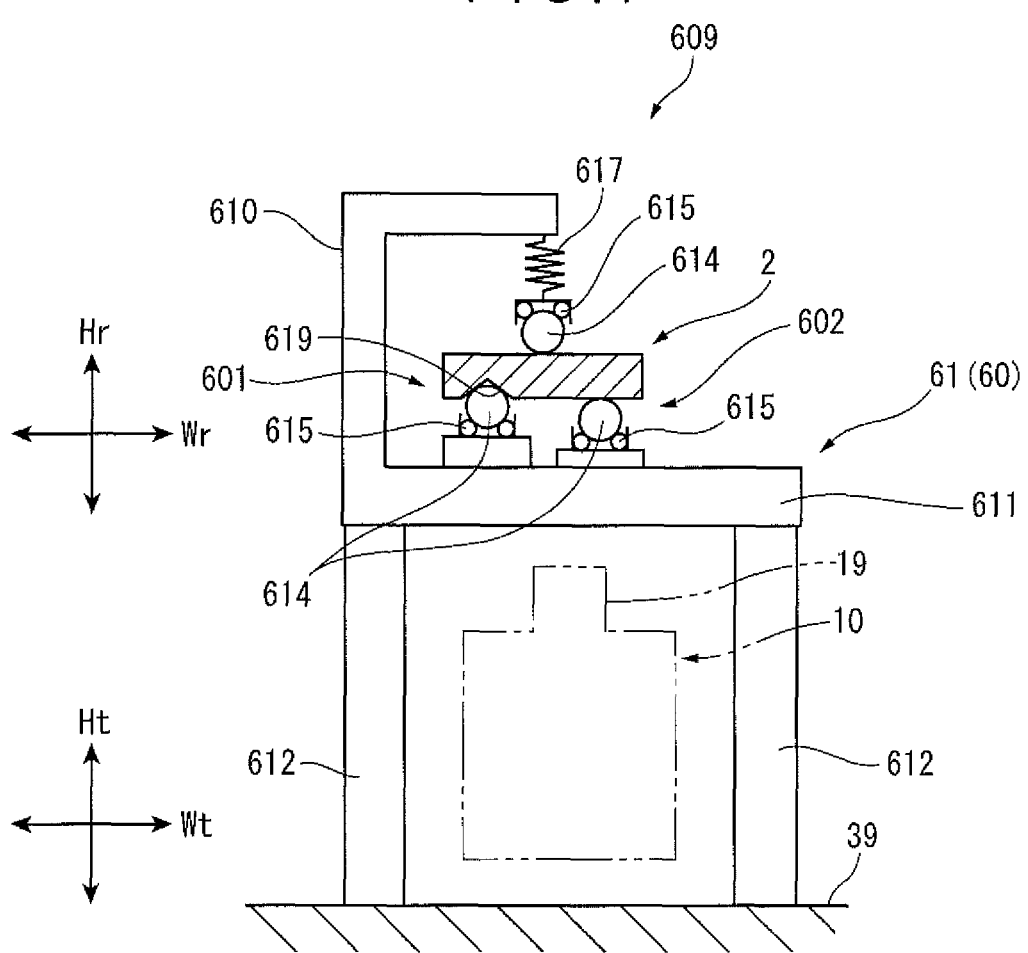
FIG. 7 is a side elevational view showing a first reference gauge support base in the first exemplary embodiment.

As shown in FIG. 7, the first reference gauge support base 61 includes a base 611 disposed above the bottom plate 39 and a post 612 fixed to a lower face of the base 611. The first reference gauge support base 61 is supported by the bottom plate 39 via the post 612.

Two pairs of balls 614 and ball holders 615 are arranged on the base 611 in alignment in the width direction Wr. The ball holder 615 includes a plurality of support balls that are configured to roll on each of the balls 614, thereby defining a so-called free ball bearing or ball caster.

The ball 614 of one of the two pairs of the balls 614 and ball holders 615 is in contact with a lower face of the reference gauge block 2 to define a plane-sphere contact portion 602.

The ball 614 of the other one of the two pairs of the balls 614 and ball holders 615 is fitted in a conical hole 619 (see FIG. 9) formed on the lower face of the reference gauge block 2 to define a conical-hole-sphere contact portion 601.

Accordingly, the first reference gauge support base 61 supports the load of the reference gauge block 2 through the plane-sphere contact portion 602 and the conical-hole-sphere contact portion 601 aligned in the width direction Wr, where the displacement in the vertical direction Hr, the displacement in the width direction Wr, the displacement in the drawing direction Lr and a rotation around an axis in the drawing direction Lr (rolling) are restricted and a rotation around an axis in the vertical direction Hr (yawing) and a rotation around an axis in the width direction Wr (pitching) are permitted.

Further, an upright portion 610 is formed on the base 611. A ball 614 and a ball holder 615 similar to those at the contact portion 602 and a compression coil spring 617 configured to bias the ball 614 and the ball holder 615 toward an upper face of the reference gauge block 2 are provided between the upright portion 610 and the upper face of the reference gauge block 2, which define a preloading unit 609 configured to preload the reference gauge block 2 downward.

The preloading unit 609 of the first reference gauge support base 61 reliably maintains the contact of the contact portions 601, 602 with the lower face of the reference gauge block 2 even when the reference gauge block 2 is of a light weight.

Second Reference Gauge Support Base 62

Figure 8:
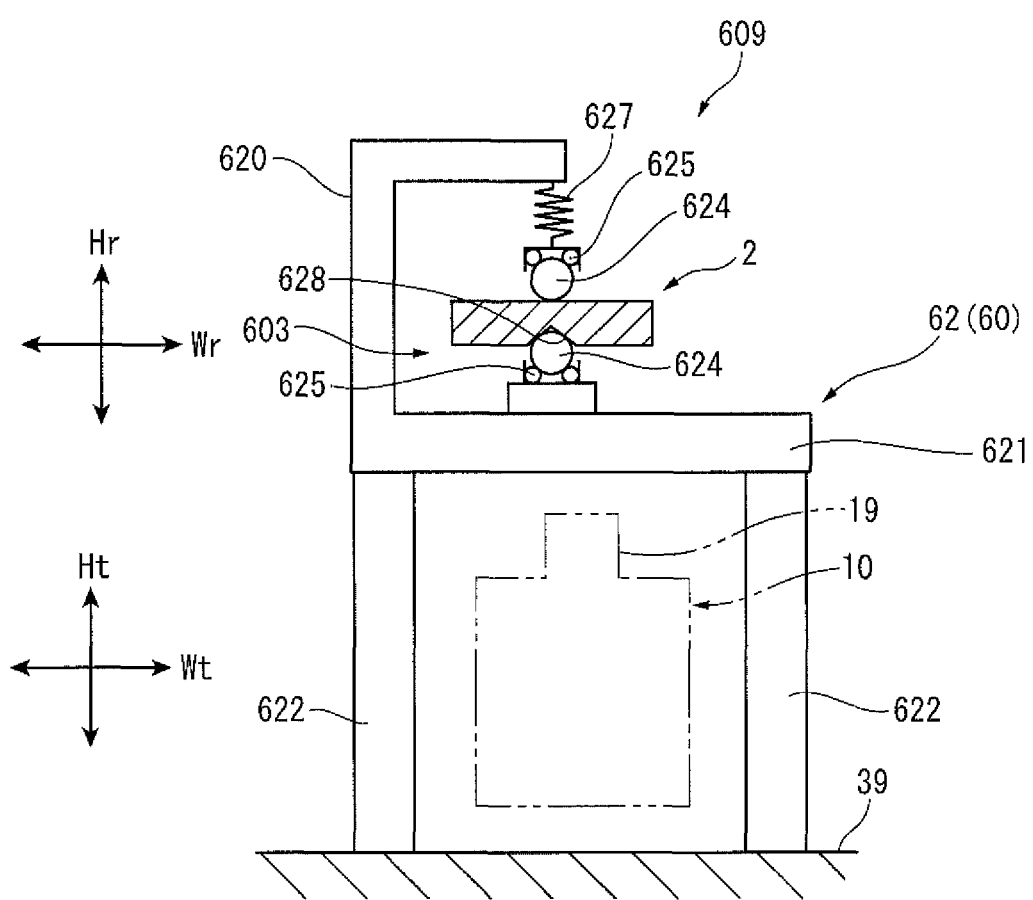
FIG. 8 is a side elevational view showing a second reference gauge support base in the first exemplary embodiment.

As shown in FIG. 8, the second reference gauge support base 62 includes a base 621, a post 622 and an upright portion 620 similar to those of the first reference gauge support base 61. A similar preloading unit 609 is defined by a ball 624, a ball holder 625 and a compression coil spring 627.

On the other hand, a V-groove-sphere contact portion 603 is defined in the second reference gauge support base 62 in place of the plane-sphere contact portion 602 and the conical-hole-sphere contact portion 601 in the first reference gauge support base 61.

The ball 624 and the ball holder 625 are provided on an upper face of the base 621. A V-shaped groove 628 is formed on an opposing lower face of the reference gauge block 2 along the drawing direction Lr (see FIG. 9). The ball 624 is fitted in the V-shaped groove 628 to define a V-shaped-groove-sphere contact portion 603.

Accordingly, the second reference gauge support base 62 supports the load of the reference gauge block 2 through the V-groove-sphere contact portion 603 and restricts the displacement in the vertical direction Hr and the displacement in the width direction Wr, whereas the displacement in the drawing direction Lr and the rotation around an axis in the drawing direction Lr (rolling), the rotation around an axis in the vertical direction Hr (yawing) and the rotation around an axis in the width direction Wr (pitching) are permitted.

As described above, the reference gauge block 2 is supported by the first reference gauge support base 61 and the second reference gauge support base 62.

With the above arrangement, the reference gauge block 2 is supported so that the position of the reference gauge block 10 in the width direction Wr is restricted by each of the first reference gauge support base 61 and the second reference gauge support base 62 and the drawing direction Lr of the reference gauge block 2 is aligned with the Y-axis direction of the temperature-controlled chamber 30 and the coordinate measuring machine 40 (i.e. the drawing direction Lt of the step gauge 10).

Further, though the position of the reference gauge block 2 in the drawing direction Lr is restricted by the contact portion 601 of the first reference gauge support base 61, the displacement of the reference gauge block 2 in the drawing direction Lr is permitted by the second reference gauge support base 62, so that the extension/contraction due to thermal deformation mainly appears on the side of the first reference surface 2A.

Measurement Process for CTE

Figure 10:
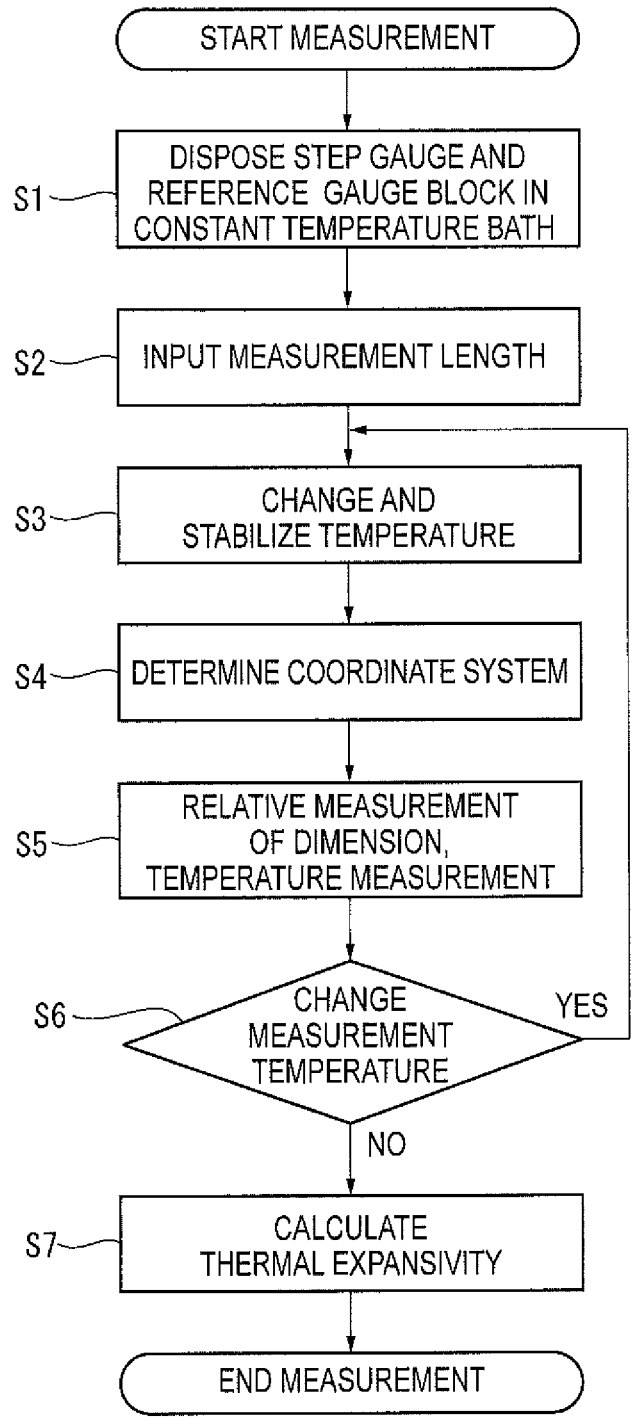
FIG. 10 is a flow chart showing a measurement process in the first exemplary embodiment.

FIG. 10 shows a process for measuring CTE of the step gauge 10 using the CTE measuring device 1.

At the start of the measurement, the CTE measuring device 1 is initially constructed by fixing the temperature-controlled chamber 30 on the coordinate measuring machine 40 and placing the step gauge 10 and the reference gauge block 2 inside the temperature-controlled chamber 30 (Step S1).

When the step gauge 10 and the reference gauge block 2 are placed inside the temperature-controlled chamber 30, the first measurement target support base 51 and the second measurement target support base 52 are initially placed to support the step gauge 10. Subsequently, the first reference gauge support base 61 and the second reference gauge support base 62 are placed to extend over the step gauge 10 to support the reference gauge block 2.

Figure 11:
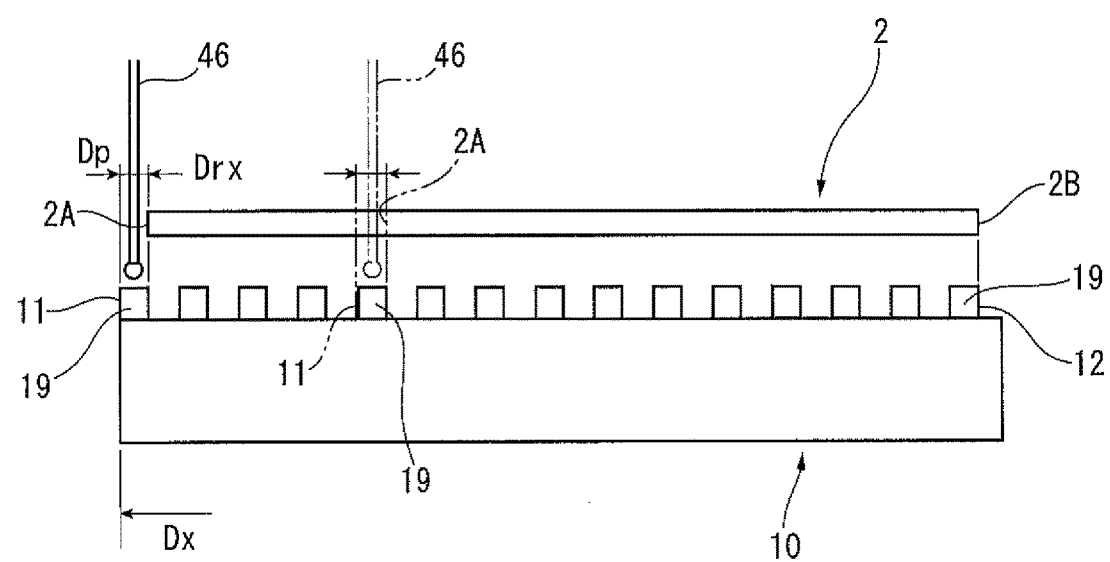
FIG. 11 is a side elevational view showing a layout of the device in the first exemplary embodiment.

As shown in FIG. 11, when the step gauge 10 and the reference gauge block 2 are placed, the positions of the ends of the step gauge 10 and the reference gauge block 2 in the drawing directions Lt, Lr are adjusted so that the second surface 12 and the second reference surface 2B are coplanar.

Since the length Drx of the reference gauge block 2 is set to be shorter than the length Dx of the step gauge 10 by the length Dp of one of the protrusions 19, the first reference surface 2A does not reach the first surface 11 by the length Dp of one of the protrusions 19 but an upper face of the one of the protrusions 19 nearest the first surface 11 is left uncovered by the reference gauge block 2 when the second reference surface 2B and the second surface 12 are coplanar.

When the step gauge 10 and the reference gauge block 2 are placed (Step S1), a measurement length (the length Dx of the step gauge 10) is inputted to the coordinate measuring machine 40 (Step S2) to perform relative measurement of the length of the step gauge 10 at different temperatures (Steps S3 to S5).

Initially, while all of the measurement apertures 31 are closed, the temperature inside the temperature-controlled chamber 30 is set at the first temperature t1 and is kept for a predetermined time so that the temperature is stabilized (Step S3).

When the temperature inside the temperature-controlled chamber 30 is stabilized at the first temperature t1, coordinate system of the step gauge 10 and the reference gauge block 2 are determined (Step S4).

Figure 12:
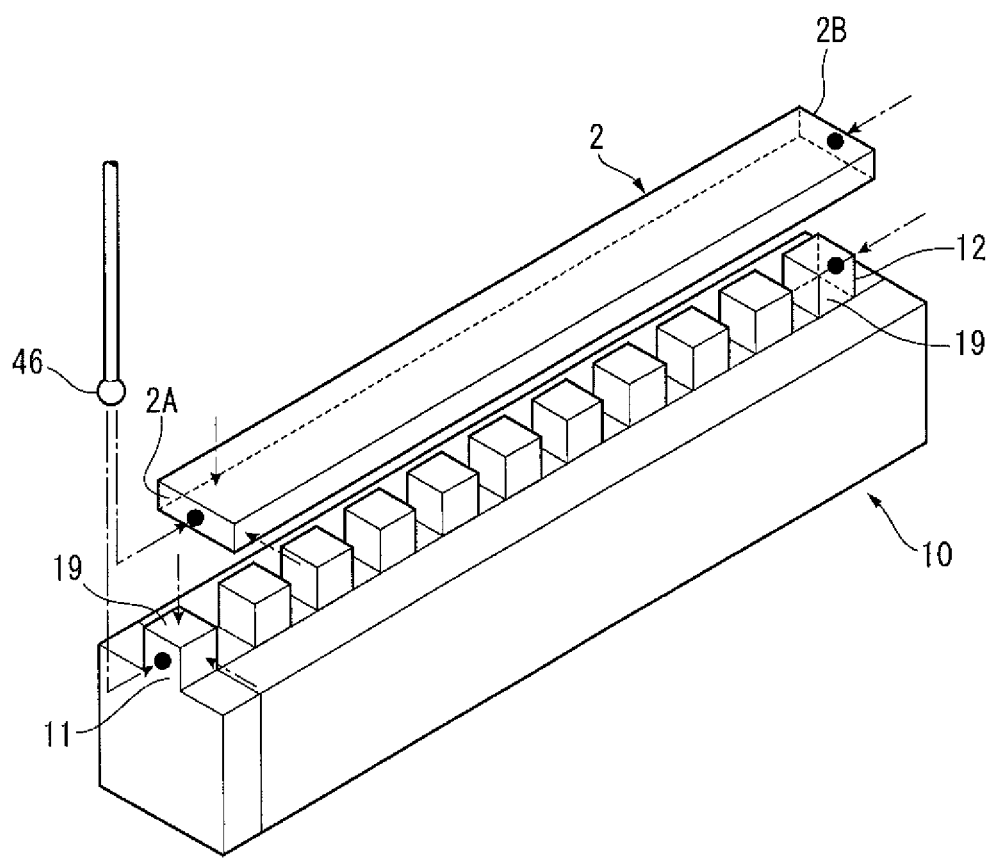
FIG. 12 is a side elevational view showing a measurement operation in the first exemplary embodiment.

Specifically, one of the measurement apertures 31 near the first surface 11 is opened and the probe 46 of the coordinate measuring machine 40 is introduced thereinto. Then, the probe 46 is brought into contact with three or more points on the first surface 11 of the step gauge 10 to detect the position and inclination of the first surface 11 as shown in FIG. 12. Further, the probe 46 is brought into contact with three or more points on an upper face and one of lateral faces of the one of the protrusions 19 on which the first surface 11 is defined to detect the position and inclination thereof. Thus, three-dimensional coordinates of the center point of the first surface 11 and the orientation of the drawing direction Lt of the step gauge 10 are obtained.

Similarly, the probe 46 is brought into contact with the first reference surface 2A and adjacent upper face and one of lateral faces of the reference gauge block 2 to obtain the three-dimensional coordinates of the center point of the first reference surface 2A and the orientation of the reference gauge block 2 in the drawing direction Lr.

Further, the probe 46 is introduced through one of the measurement apertures 31 near the second surface 12 to measure the second surface 12 of the step gauge 10 and the second reference surface 2B of the reference gauge block 2, thereby obtaining three-dimensional coordinates of the center points of the second surface 12 and the second reference surface 2B.

When the coordinate systems of the step gauge 10 and the reference gauge block 2 are determined (Step S4), a relative measurement of the dimensions of the step gauge 10 and the reference gauge block 2 is performed and the temperature at the time of the relative measurement is measured and recorded (Step S5).

Specifically, in the coordinate system determined in Step S4, the relative measurement of the distance between the first surface 11 and the second surface 12 (i.e. an accurate value of the length Dx) can be performed based on the distance between the first reference surface 2A and the second reference surface 2B (the length Drx of the reference gauge block 2) with reference to the distance between the center point of the first surface 11 and the center point of the first reference surface 2A, and the distance between the center point of the second surface 12 and the center point of the second reference surface 2B.

When the relative measurement of the distance between the first surface 11 and the second surface 12 at the first temperature t1 is completed, the temperature inside the temperature-controlled chamber 30 is changed to the second temperature t2 (Step S6), and the above-described relative measurement operations (Step S3 to S5) are repeated.

A length Dx1 at the first temperature t1 and a length Dx2 at the second temperature t2 thus obtained is used for the calculation of the CTE $\alpha=[(Dx1-Dx2)/D]/(t1-t2)$ (D denotes the length of the step gauge 10) of the step gauge 10 between the first surface 11 and the second surface 12 (Step S7). It should be noted that the length D may be one of or average of the measured length Dx1 and the length Dx2, or a nominal length of the step gauge 10. Since the length D in either case is sufficiently large with respect to the thermal deformation $\Delta D=(Dx1-Dx2)$, the calculation of the CTE $\alpha$ is not significantly influenced by the nature of the length D.

Advantages of First Exemplary Embodiment

The above-described first exemplary embodiment offers the following advantages.

Since the length of the step gauge 10 (measurement target) is measured using the coordinate measuring machine 40, the CTE of the step gauge 10 having various lengths can be highly accurately measured without using an expensive optical interferometer.

Further, in the first exemplary embodiment, the reference gauge block 2 is used as a length master and the relative measurement of the length with respect to the reference gauge block 2 is performed in measuring the length of the step gauge 10 using the coordinate measuring machine 40. Accordingly, the results of the length measurement are not dependent on the accuracy of the scale of the coordinate measuring machine 40 but are solely dependent on the accuracy of the reference gauge block 2. Thus, high accuracy of the measurement results can be ensured even when the length of the step gauge 10 is increased.

In the first exemplary embodiment, the coordinate system is determined (Step S4 in FIG. 10) including the calculation of the center coordinates of the first reference surface 2A, the second reference surface 2B, the first surface 11 and the second surface 12 and the calculation of the inclination of the reference gauge block 2 and the step gauge 10 with respect to the drawing directions Lr, Lt, when the relative measurement is performed.

Accordingly, even when the first reference surface 2A and the second reference surface 2B of the reference gauge block 2, and the first surface 11 and the second surface 12 of the step gauge 10 are inclined with respect to the drawing directions Lr, Lt, the detected position by the coordinate measuring machine 40 can be corrected based on the distance between the contact point of the probe 46 and the center coordinates on the surfaces and the inclinations of the surfaces.

Further, since the coordinate system of each of the reference gauge block 2 and the step gauge 10 is determined based on the current condition of the reference gauge block 2 and the step gauge 10 and the length measurement is performed under the coordinate system, the accuracy of the length measurement can be enhanced and, consequently, the accuracy of the relative measurement can be kept at a high level.

In the first exemplary embodiment, the first surface 11 and the second surface 12 (i.e. the measurement target portion of the step gauge 10) are defined near the measurement apertures 31 and the reference gauge block 2 is also disposed near the measurement apertures 31, so that the first reference surface 2A and the second reference surface 2B (i.e. comparison target) can be disposed close to the first surface 11 and the second surface 12, thereby improving the measurement accuracy and the efficiency and speed of the measurement operations.

In the first exemplary embodiment, the length Drx from the first reference surface 2A to the second reference surface 2B of the reference gauge block 2 is set to be shorter than the length Dx from the first surface 11 to the second surface 12 of the step gauge 10 by the length Dp of one of the protrusions 19.

Thus, even when the reference gauge block 2 is disposed near the measurement apertures 31 of the step gauge 10 and the surface of the step gauge 10 is shielded by the reference gauge block 2, a part of the surface of an end of the step gauge 10 near the first surface 11 is exposed towards the measurement apertures 31 for the short length of the reference gauge block 2. Accordingly, the probe 46 of the coordinate measuring machine 40 is brought into contact with the exposed surface in determining the coordinate system as described above, so that the surface of the step gauge 10 can be detected without causing any interference with the reference gauge block 2.

In the first exemplary embodiment, since the second reference surface 2B and the second surface 12 are coplanarly arranged, the difference in the lengths of the reference gauge block 2 and the step gauge 10 is maximized at the end (i.e. the side at which the first surface 11 and the first reference surface 2A are defined) opposite the coplanar side when the reference gauge block 2 is set to be shorter than the step gauge 10 by the predetermined length, so that the margin for the surface detection using the probe 46 of the coordinate measuring machine 40 can be maximized.

In the first exemplary embodiment, since the combination of the contact portion 504 with the lateral face of the step gauge 10 and the pressing unit 505 in the first measurement target support base 51 restricts the displacement of the step gauge 10 in two directions (the vertical direction Ht, the width direction Wt) intersecting the drawing direction Lt while permitting the displacement in the drawing direction Lt, the combination of the contact portion 504 and the pressing unit 505 provides a function corresponding to that of a combination of a V-shaped groove and a sphere of a kinematic mount. As a result, the function corresponding to the kinematic mount can be obtained in the first measurement target support base 51 and the second measurement target support base 52, so that the displacement and rotation in the drawing direction Lt and directions intersecting the drawing direction Lt can be appropriately restricted.

In the first exemplary embodiment, the reference gauge support base 60 includes the first reference gauge support base 61 and the second reference gauge support base 62, which define a three-point kinematic mount including the conical-hole-sphere contact portion 601, the plane-sphere contact portion 602 and the V-shaped-groove-sphere contact portion 603 in contact with the bottom face of the reference gauge block 2, so that the displacement and rotation in the drawing direction Lr and directions (vertical direction Hr, width direction Wr) intersecting the drawing direction Lt can be appropriately restricted.

Since the preloading unit 609 configured to downwardly preload the reference gauge block 2 is provided in the first exemplary embodiment, even when the reference gauge block 2 is of a light weight, the reference gauge block 2 can be stably supported by the first reference gauge support base 61 and the second reference gauge support base 62 by virtue of the downward preloading.

It should be noted that the first exemplary embodiment is applicable to a measurement of the step gauge 10 with shorter length or to a measurement of a length between the protrusions 19 at the middle portion of the step gauge 10.

When the length of a middle portion of the step gauge 10 is measured as shown in FIG. 11, the first surface 11 is defined at one of the protrusions 19 at the middle portion as shown in dot-and-dash line, the first reference surface 2A is defined using a reference gauge block 2 of a corresponding length and the first surface 11 and the first reference surface 2A may be measured using the probe 46. At this time, the nearest one of the plurality of measurement apertures 31 may be used when the probe 46 is introduced into the temperature-controlled chamber 30.

Second Exemplary Embodiment

Figure 13:
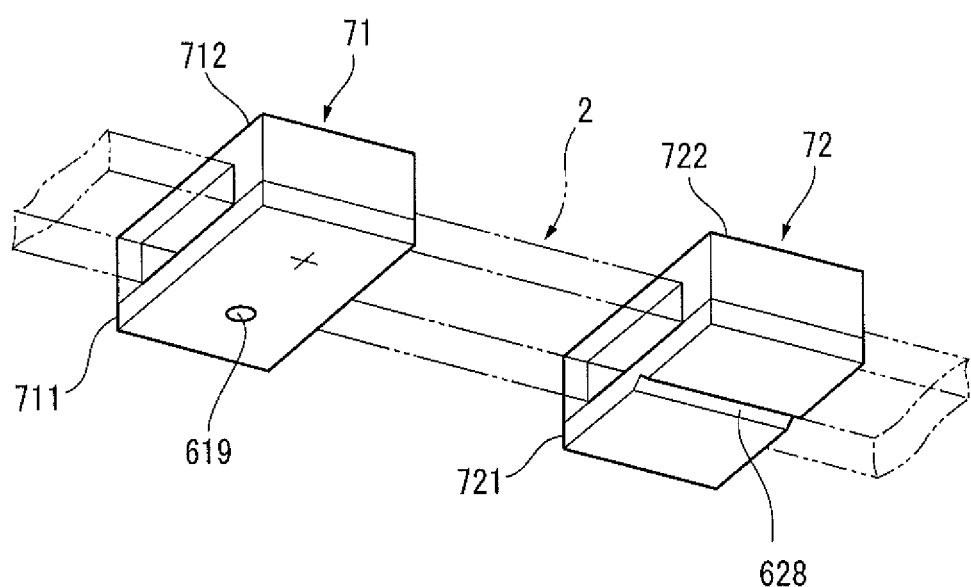
FIG. 13 is a perspective view showing a support adapter in a second exemplary embodiment of the invention.

FIG. 13 shows a second exemplary embodiment of the invention.

In the above-described first exemplary embodiment, the conical hole 619 and the V-shaped groove 628 are directly formed on the lower face of the reference gauge block 2 in order to support the reference gauge block 2 using the first reference gauge support base 61 and the second reference gauge support base 62.

In contrast, support adapters 71, 72 are attached to the reference gauge block 2 in the second exemplary embodiment as shown in FIG. 3 and the conical hole 619 and the V-shaped groove 628 are formed on the lower faces of the support adapters 71, 72.

It should be noted that the arrangement of the second exemplary embodiment is the same as the above-described first exemplary embodiment except for the support arrangement of the reference gauge block 2 and duplicated description will be omitted. Only the difference will be described below.

It should further be noted that, though the support adapters 71, 72 are attached to the reference gauge block 2 in the second exemplary embodiment, the support adapter may be applied to the step gauge 10.

The support adapter 71 is provided to the reference gauge block 2 at a position capable of being supported by the first reference gauge support base 61. The support adapter 71 includes a support plate 711 and a fixing member 712. The support plate 711 and the fixing member 712 hold therein the reference gauge block 2 so that the support adapter 71 is fixed to the reference gauge block 2.

The support adapter 72 is provided to the reference gauge block 2 at a position capable of being supported by the second reference gauge support base 62. The support adapter 72 includes a support plate 721 and a fixing member 722. The support plate 721 and the fixing member 722 hold therein the reference gauge block 2 so that the support adapter 72 is fixed to the reference gauge block 2.

A conical hole 619 is formed on a lower face of the support plate 711. A V-shaped groove 628 is formed on a lower face of the support plate 721.

Figure 9:
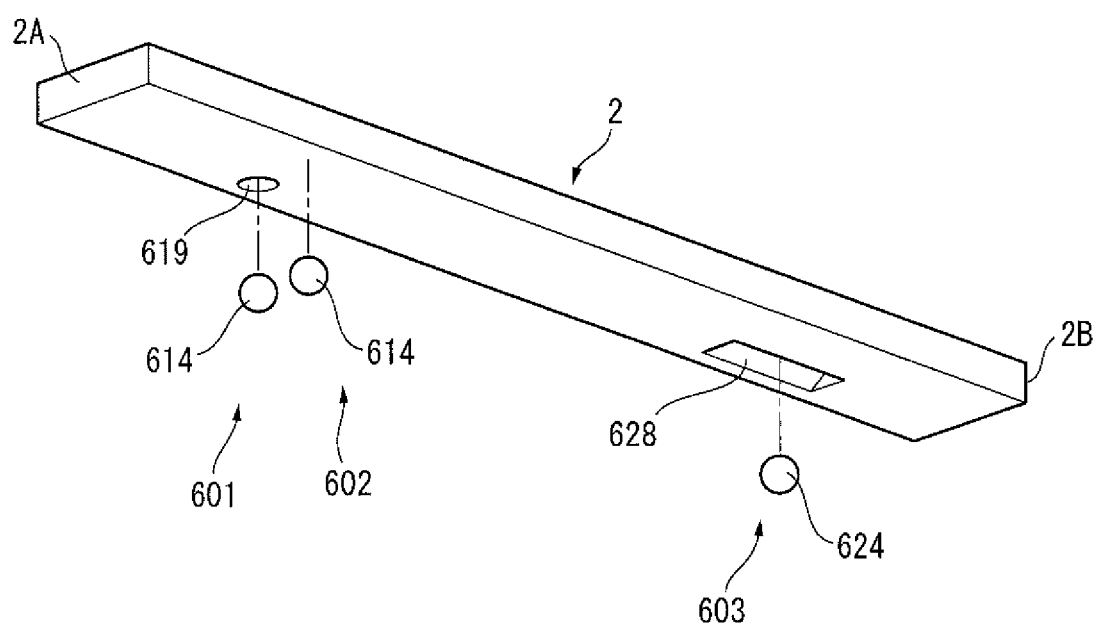
FIG. 9 is a perspective view showing a bottom side of the reference gauge block in the first exemplary embodiment.

With the use of the conical hole 619 and the V-shaped groove 628, the conical-hole-sphere contact portion 601, the plane-sphere contact portion 602 and the V-shaped-groove-sphere contact portion 603 are defined between the support adapters 71, 72 and the first and second reference gauge support bases 61, 62 in a manner similar to the lower face of the reference gauge block 2 in the first exemplary embodiment (see FIG. 9).

According to the second exemplary embodiment as described above, the advantages of the above-described first exemplary embodiment can be obtained without providing the conical hole 619 and the V-shaped groove 628 on the lower face of the reference gauge block 2.

Since it is not necessary to provide the conical hole 619 and the V-shaped groove 628 on the lower face of the reference gauge block 2, general-purpose reference gauge blocks 2 can be used by using the support adapters 71, 72 in common, whereby the reference gauge blocks 2 of various dimensions can be easily used.

Third Exemplary Embodiment

Figure 14:
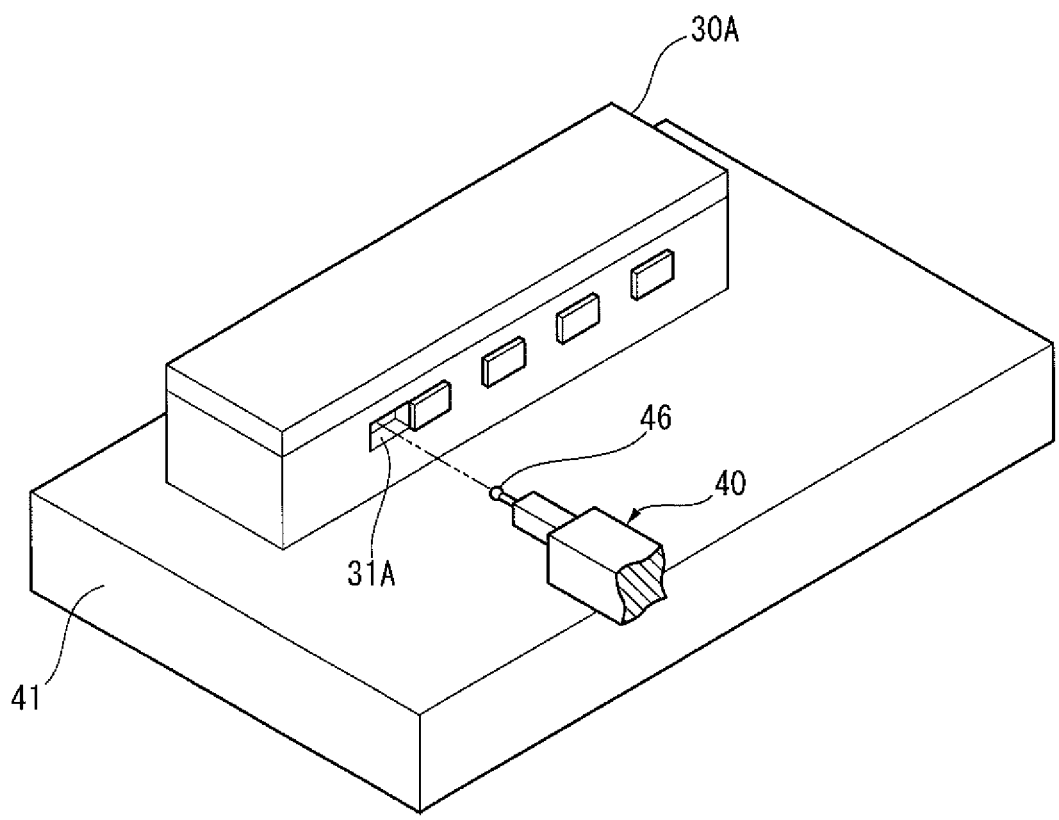
FIG. 14 is a perspective view showing a temperature-controlled chamber in a third exemplary embodiment of the invention.
Figure 15:
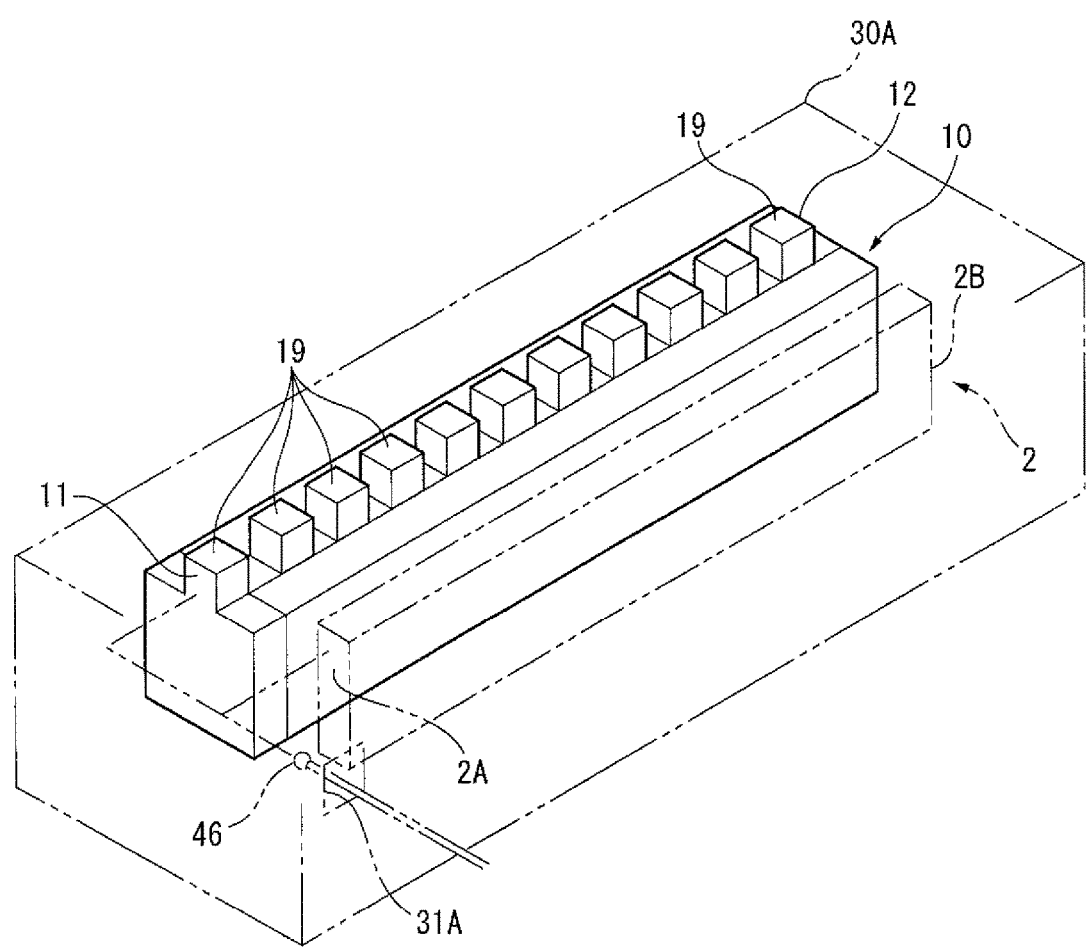
FIG. 15 is a perspective view showing an arrangement of a temperature-controlled chamber, a step gauge and a reference gauge block in the third exemplary embodiment.

FIGS. 14 and 15 show a third exemplary embodiment of the invention.

In the above-described first exemplary embodiment, the measurement aperture 31 for introducing the probe 46 is provided on the upper face of the temperature-controlled chamber 30 and the protrusions 19 are provided to the upper face of the step gauge 10 (i.e. at the side facing the measurement apertures 31) and the reference gauge block 2 is provided in parallel to and above the step gauge 10 inside the temperature-controlled chamber 30.

In contrast, as shown in FIGS. 14 and 15, measurement apertures 31A into which the probe 46 is configured to be introduced are provided on one of lateral faces of the temperature-controlled chamber 30A, the step gauge 10 is disposed along the one of the lateral faces and the reference gauge block 2 is disposed between the one of the lateral faces and the step gauge 10 in parallel to each other.

The third exemplary embodiment offers the same advantages as those mentioned in the above-described first exemplary embodiment.

Fourth Exemplary Embodiment

Figure 16:
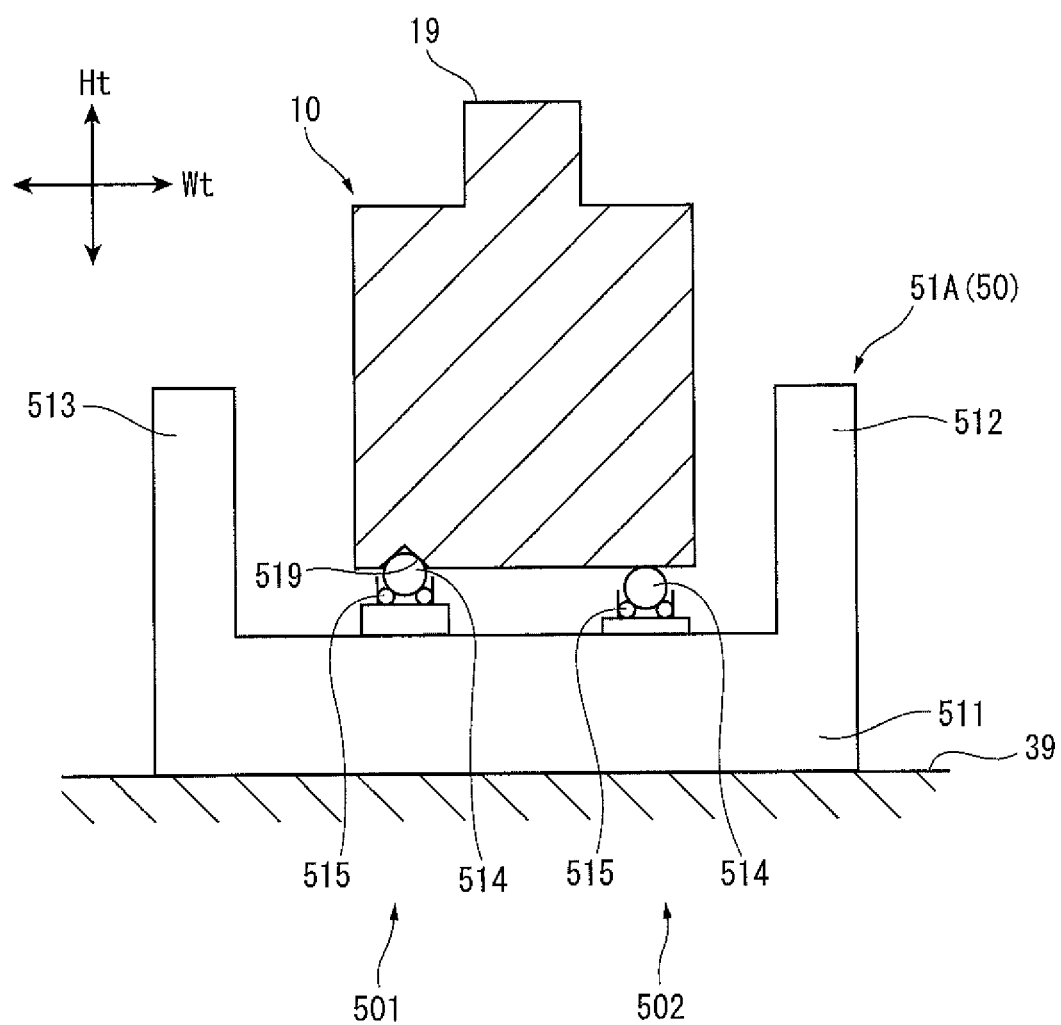
FIG. 16 is a side elevational view showing a first measurement target support base in a fourth exemplary embodiment of the invention.
Figure 17:
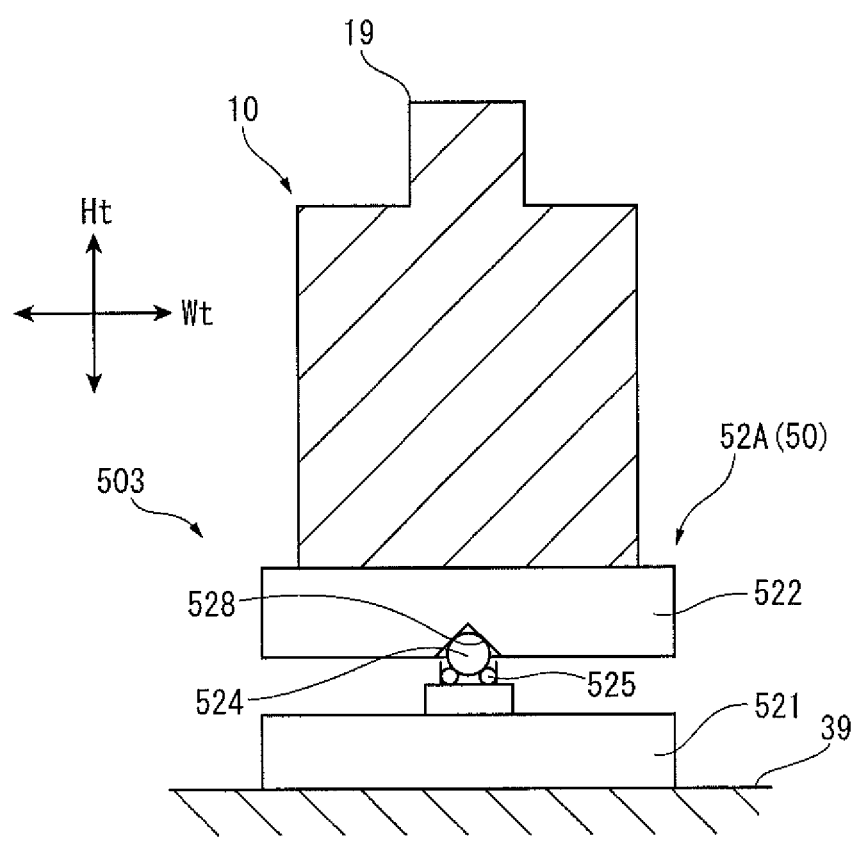
FIG. 17 is a side elevational view showing a second measurement target support base in the fourth exemplary embodiment.

FIGS. 16 and 17 show a fourth exemplary embodiment of the invention.

In the above-described first exemplary embodiment, two plane-sphere contact portions 502 are provided between the lower face of the step gauge 10 and the first measurement target support base 51 (see FIG. 5), and the pressing unit 505 and the contact portion 504 are provided on the lateral faces to hold the step gauge 10 therebetween. Further, the second measurement target support base 52 (see FIG. 6) includes the conical-hole-sphere contact portion 501 defined against the lower face of the step gauge 10.

In contrast, a first measurement target support base 51A (see FIG. 16) of the fourth exemplary embodiment includes a plane-sphere contact portion 502 and the conical-hole-sphere contact portion 501 (conical hole 519) abutting the lower face of the step gauge 10 and a second measurement target support base 52A (see FIG. 17) includes a V-shaped-groove-sphere contact portion 503 (V-shaped groove 528) abutting the lower face of the step gauge 10.

According to the fourth exemplary embodiment, an arrangement corresponding to the kinematic mount can be provided between the step gauge 10 and the first and second measurement target support bases 51A, 52A.

It should be noted that the conical-hole-sphere contact portion 501 may be provided between the first measurement target support base 51A and the step gauge 10 and the plane-sphere contact portion 502 and the V-shaped-groove-sphere contact portion 503 may be provided between the second measurement target support base 52A and the step gauge 10.

Fifth Exemplary Embodiment

Figure 18:
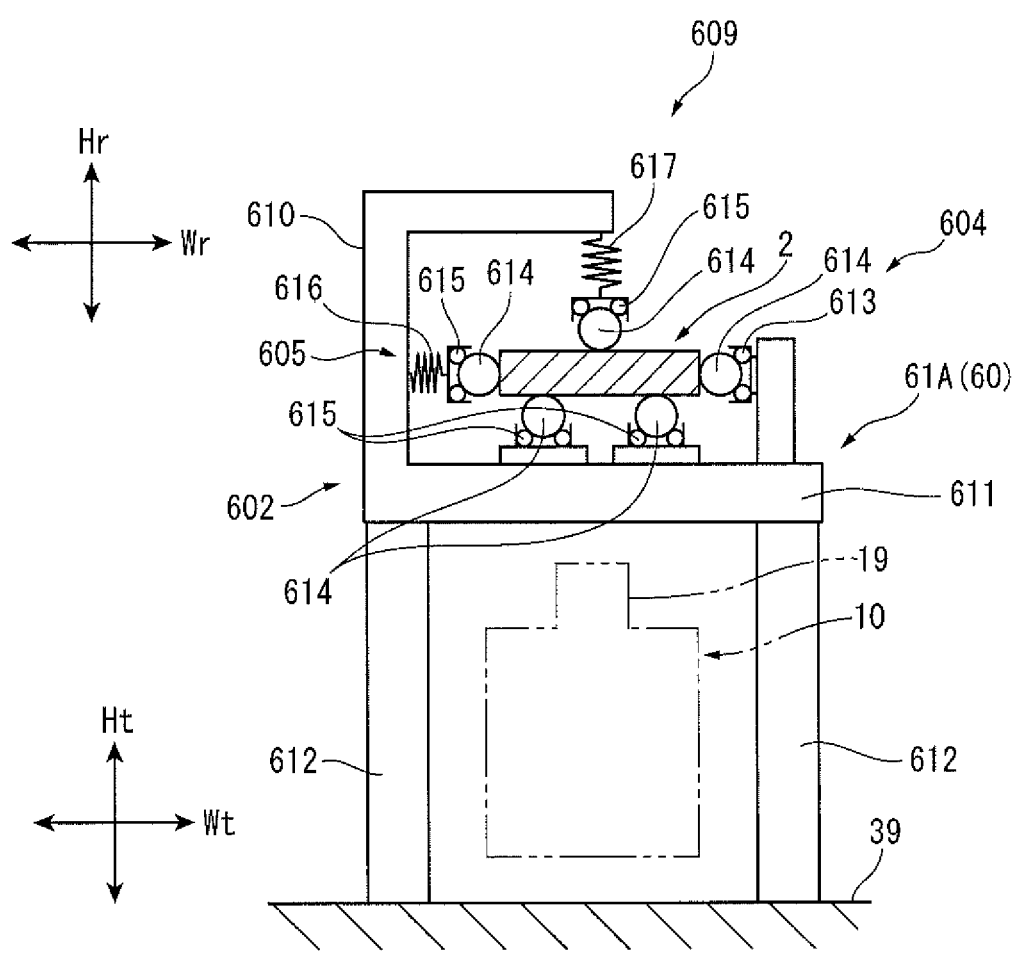
FIG. 18 is a side elevational view showing a first reference gauge support base in a fifth exemplary embodiment.
Figure 19:
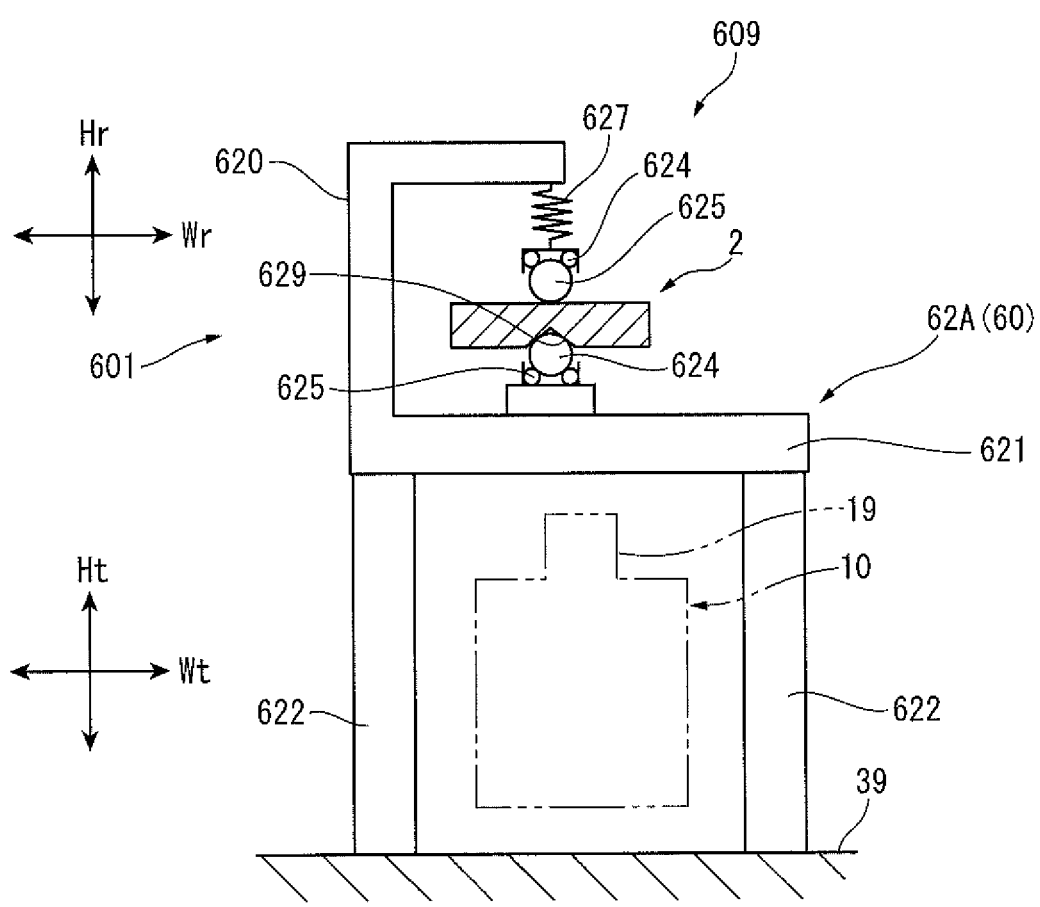
FIG. 19 is a side elevational view showing a second reference gauge support base in the fifth exemplary embodiment.

FIGS. 18 and 19 show a fifth exemplary embodiment of the invention.

In the above-described first exemplary embodiment, the first reference gauge support base 61 (see FIG. 7) includes the conical-hole-sphere contact portion 601 and the plane-sphere contact portion 602 abutting the lower face of the reference gauge block 2 and the second reference gauge support base 62 (see FIG. 8) includes the V-shaped-groove-sphere contact portion 603 abutting the lower face of the reference gauge block 2.

In contrast, a first reference gauge support base 61A (see FIG. 18) of the fifth exemplary embodiment includes two plane-sphere contact portions 602 abutting the lower face of the reference gauge block 2, a pressing unit 605 (the ball 614, the ball holder 615, the compression coil spring 616) and a contact portion 604 (the ball 614, the ball holder 615) that are configured to hold lateral faces of the reference gauge block 2. Further, a second reference gauge support base 62A (see FIG. 19) includes the conical-hole-sphere contact portion 601 (conical hole 629) defined against the lower face of the reference gauge block 2.

According to the fifth exemplary embodiment, an arrangement corresponding to the kinematic mount can also be provided between the reference gauge block 2 and the first and second reference gauge support bases 61A, 62A.

It should be noted that the V-shaped-groove-sphere contact portion 603 and the plane-sphere contact portion 602 may be provided between the first reference gauge support base 61A and the reference gauge block 2, and the conical-hole-sphere contact portion 601 may be provided between the second reference gauge support base 62A and the reference gauge block 2.

Sixth Exemplary Embodiment

Figure 20:
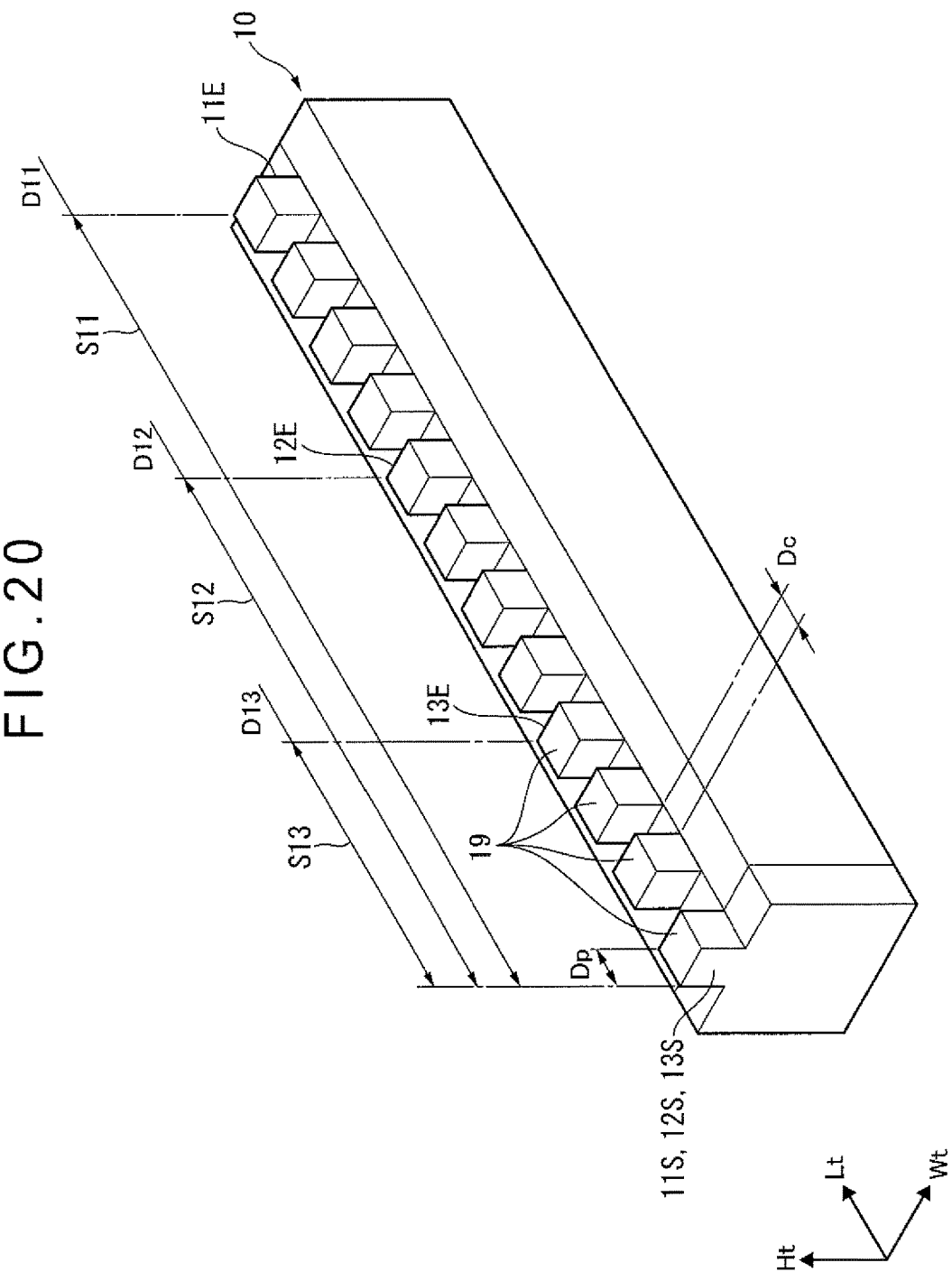
FIG. 20 is a perspective view showing a step gauge (a measurement target in a sixth exemplary embodiment of the invention).

FIG. 20 shows a step gauge 10 (measurement target) in a sixth exemplary embodiment.

In the sixth exemplary embodiment, the step gauge 10 includes three measurement sections S11, S12, S13.

The first measurement section S11 is defined between a first measurement start point 11S and a first measurement end point 11E, the first measurement start point 11S being defined on a surface (a surface intersecting the drawing direction Lt) of one of the protrusions 19 at a first end of the step gauge 10, the first measurement end point 11E being defined on a surface of another one of the protrusions 19 at a second end of the step gauge 10. The length of the first measurement section is D11.

The second measurement section S12 is defined between a second measurement start point 12S and a second measurement end point 12E, the second measurement start point 12S being defined on the same surface as that of the first measurement start point 11S, the second measurement end point 12E being defined on a surface of still another one of the protrusions 19 at a middle portion of the step gauge 10. The length of the second measurement section is D12, which is shorter than D11.

The third measurement section S13 is defined between a third measurement start point 13S and a third measurement end point 13E, the third measurement start point 13S being defined on the same surface as that of the first measurement start point 11S, the third measurement end point 13E being defined on a surface of a further one of the protrusions 19 at the middle portion of the step gauge 10. The length of the third measurement section is D13, which is shorter than D12.

Figure 21:
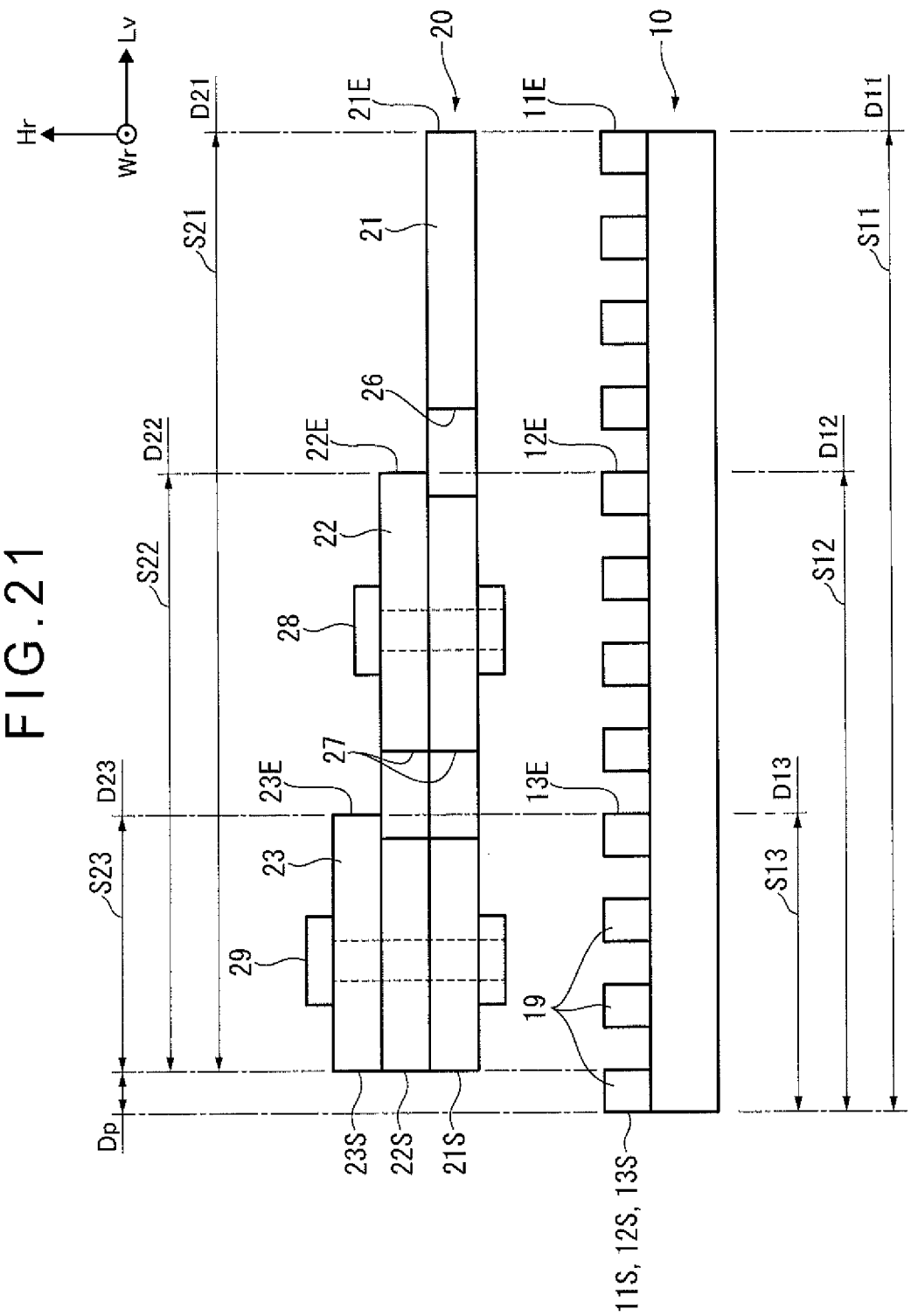
FIG. 21 is a side elevational view showing a reference gauge in the sixth exemplary embodiment.
Figure 22:
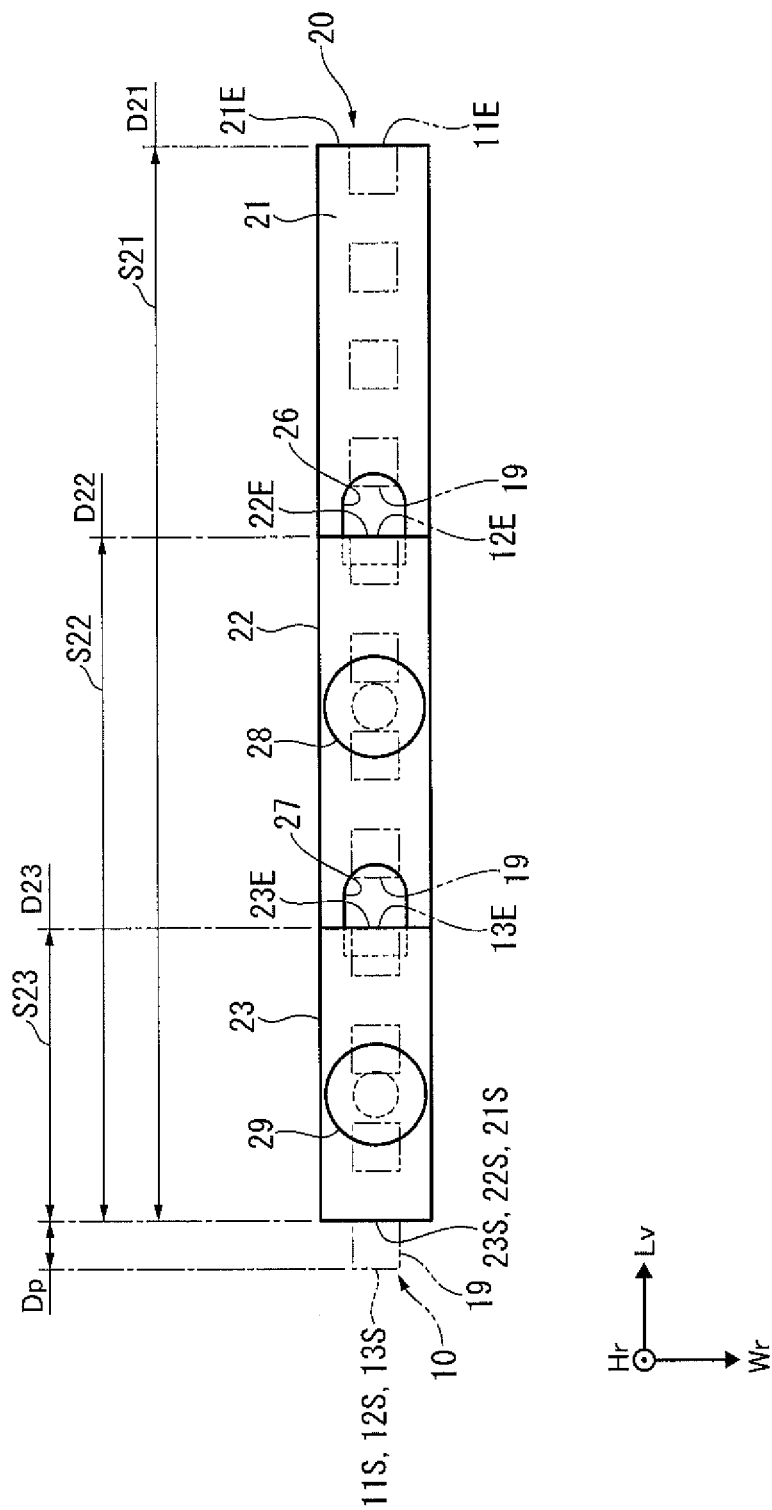
FIG. 22 is a plan view showing the reference gauge in the sixth exemplary embodiment.

FIGS. 21 and 22 show a reference gauge block 20 according to the sixth exemplary embodiment.

The reference gauge block 20 includes three gauge blocks 21, 22, 23.

The gauge blocks 21 to 23 each have the same thickness (a dimension in the vertical direction Hr) and the same width (a dimension in the width direction Wr), but are different in lengths (a dimension in the drawing direction Lr).

Specifically, the gauge blocks 21, 22, 23 respectively have a length D21, length D22 and length D23 corresponding to the above-described three measurement sections S11, S12, S13 (each having lengths D11, D12, D13) of the step gauge 10.

The above-described gauge blocks 21, 22, 23 define three reference sections S21, S22, S23 on the reference gauge block 20.

The first reference section S21 is defined between a first reference start point 21S and a first reference end point 21E respectively at first and second end faces of the gauge block 21. The first reference section length D21 is set to be shorter than the corresponding first measurement section length DI 1 by the length Dp of one of the protrusions 19.

The second reference section S22 is defined between a second reference start point 22S and a second reference end point 22E respectively at first and second end faces of the gauge block 22. The second reference section length D22 is set to be shorter than the corresponding second measurement section length D12 by the length Dp of one of the protrusions 19.

The third reference section S23 is defined between a third reference start point 23S and a third reference end point 23E respectively at first and second end faces of the gauge block 23. The third reference section length D23 is set to be shorter than the corresponding third measurement section length D13 by the length Dp of one of the protrusions 19.

The three gauge blocks 21, 22, 23 of the reference gauge block 20 are layered in a descending order of the length thereof and are attached by fixtures 28, 29 penetrating through the gauge blocks 21, 22, 23. Specifically, the two gauge blocks 21, 22 are fastened by the fixture 28 and the three gauge blocks 21, 22, 23 are fastened by the fixture 29.

The gauge blocks 21 to 23 are not necessarily fastened by the fixture 29 but may be rigidly attached while being layered by other mechanism(s) such as mutual bonding and bundling with a use of a belt-shaped member.

Insert holes 26, 27 are formed on each of the two gauge blocks 21, 22 (i.e. two of the three gauge blocks 21 to 23 except for the uppermost gauge block 23).

The insert hole 26 is formed at a position of the middle portion of the gauge block 21 to be overlapped with the second end at which the second reference end point 22E of the gauge block 22 is defined. When the gauge blocks 21, 22 are fastened, the edge of the gauge block 22 protrudes into the opening of the insert hole 26.

The insert hole 27 is formed at a position of the middle portions of the gauge blocks 21, 22 to be overlapped with the second end at which the third reference end point 23E of the gauge block 23 is defined. When the gauge blocks 21 to 23 are fastened, the insert holes 27 of the gauge blocks 21, 22 are mutually intercommunicated and the edge of the gauge block 23 protrudes into the opening of the insert holes 27.

Figure 23:
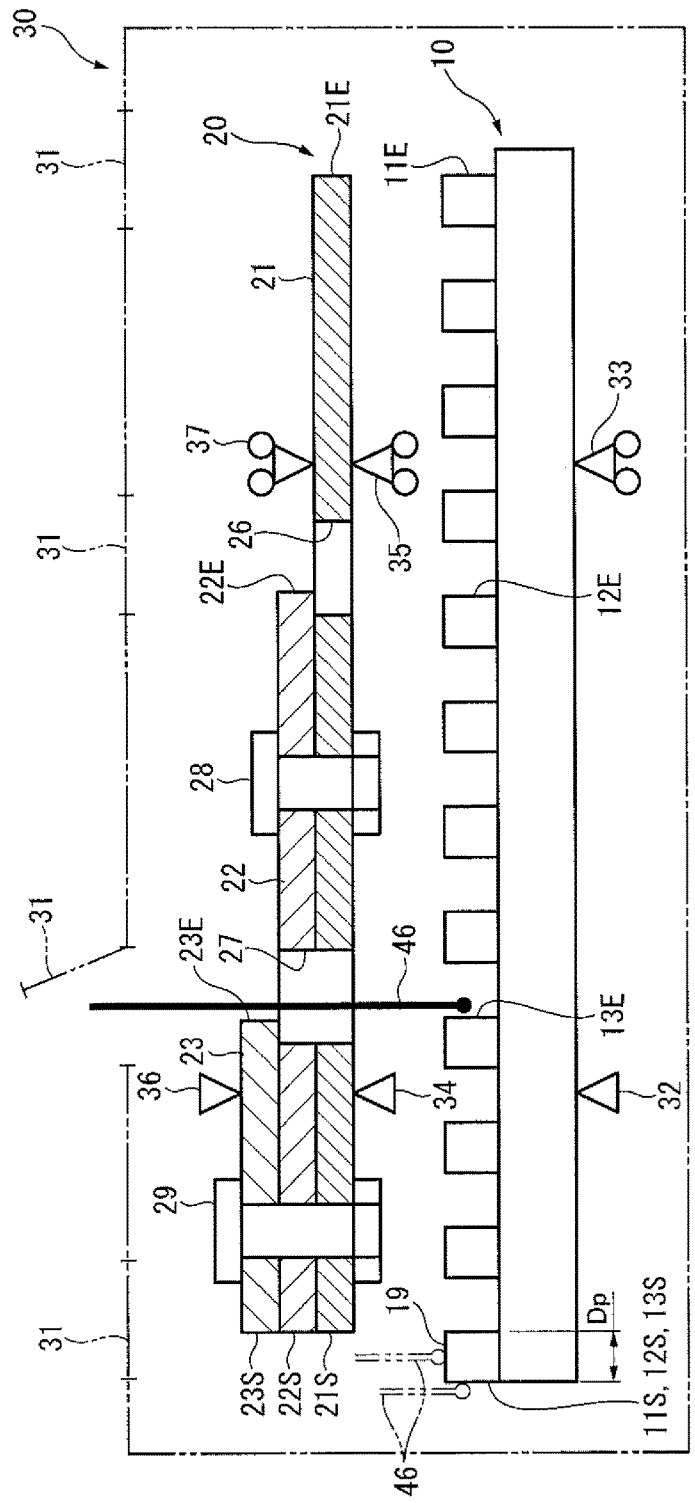
FIG. 23 is a schematic illustration of a measurement condition in the sixth exemplary embodiment.

FIG. 23 shows the step gauge 10 and the reference gauge block 20 housed in the temperature-controlled chamber 30.

The step gauge 10 and the reference gauge block 20 are placed in the temperature-controlled chamber 30 in parallel with each other. Specifically, the step gauge 10 and the reference gauge block 20 are placed so that all of the drawing direction Lt of the step gauge 10, the drawing direction Lr of the reference gauge block 20 and the Y-axis direction of the temperature-controlled chamber 30 are aligned in the same direction.

The lower face of the step gauge 10 is supported by supports 32, 33 provided in the temperature-controlled chamber 30.

The support 32 restricts the displacement of the step gauge 10 in the drawing direction Lt and the width direction Wt. However, all of the rotations of the step gauge 10 around axes in the drawing direction Lt, the vertical direction Ht and the width direction Wt are permitted.

The moving support 33 restricts the displacement of the step gauge 10 in the width direction Wt but permits the displacement of the step gauge 10 in the drawing direction Lt. Further, all of the rotations of the step gauge 10 around axes in the drawing direction Lt, the vertical direction Ht and the width direction Wt are permitted.

The supports 32, 33 can be exemplarily provided by a so-called kinematic mount (restriction of translational three-degree-of-freedom (X, Y, Z) by a contact of a sphere and a conical hole, restriction of rotational two-degree-of-freedom (pitch, yaw) by a contact of a sphere and a V-shaped groove, restriction of single-degree-of-freedom (roll) by a contact between a sphere and a plane).

Since the step gauge 10 is supported by the above-described supports 32, 33, the drawing direction Lt of the step gauge 10 is always kept constant and the extension/contraction due to thermal deformation mainly appears on the side of the first to third measurement end points 11E to 13E.

The lower face of the reference gauge block 20 is supported by supports 34, 35 provided in the temperature-controlled chamber 30 and the upper face of the reference gauge block 20 is pressed by pressing devices 36, 37.

The fixed support 34 restricts the displacement of the reference gauge block 20 in the drawing direction Lt and the width direction Wt. However, all of the rotations of the reference gauge block 10 around axes in the drawing direction Lt, the vertical direction Ht and the width direction Wt are permitted.

The moving support 35 restricts the displacement of the reference gauge block 20 in the width direction Wt but permits the displacement of the reference gauge block 20 in the drawing direction Lt. Further, all of the rotations of the reference gauge block 20 around axes in the drawing direction Lt, the vertical direction Ht and the width direction Wt are permitted.

The supports 34, 35 can also be exemplarily provided by a so-called kinematic mount (restriction of translational three-degree-of-freedom (X, Y, Z) by a contact of a sphere and a conical hole, restriction of rotational two-degree-of-freedom (pitch, yaw) by a contact of a sphere and a V-shaped groove, restriction of single-degree-of-freedom (roll) by a contact between a sphere and a plane).

Since the reference gauge block 20 is supported by the above-described supports 34, 35, the drawing direction Lr of the reference gauge block 20 is always kept constant and the extension/contraction due to thermal deformation mainly appears on the side of the first to third measurement end points 21E to 23E.

The pressing devices 36, 37 include resilient coil spring and the like and face the supports 34, 35 to press the reference gauge block 20 against the supports 34, 35.

Among the above, the pressing device 37 includes a so-called free ball bearing or a ball caster so as to permit the displacement of the reference gauge block 20 in the drawing direction Lt in a manner corresponding to the moving support 35.

With the use of the pressing devices 36, 37, even when the reference gauge block 20 of a light weight is used, the reference gauge block 20 can be pressed toward the supports 34, 35 to stably support the reference gauge block 20 by the supports 34, 35.

When being placed in the temperature-controlled chamber 30, the reference gauge block 20 is disposed at a position shifted with respect to the step gauge 10 toward the first reference end point 21E by the length Dp of one of the protrusions 19 of the step gauge 10.

In this state, the first to third measurement end points 11E to 13E are respectively aligned with the corresponding first to third reference end points 21E to 23E (see FIG. 21).

The reference gauge block 20 is placed in the temperature-controlled chamber 30 between the measurement apertures 31 and the step gauge 10.

Accordingly, the positions of the first to third reference start points 21S to 23S and the first to third reference end points 21E to 23E of the reference gauge block 20 can be detected by a contact of the probe 46 introduced through the nearest one of the measurement apertures 31.

On the other hand, most part of the side of the step gauge 10 near the measurement apertures 31 is shielded with the reference gauge block 20 and only the upper face of the protrusion 19 on which the first to third measurement start points 11S to 13S are defined is unshielded.

However, since the reference gauge block 20 is provided with the insert holes 26, 27, the probe 46 can be introduced through the insert holes 26, 27, so that the probe 46 can be brought into contact with the second and third measurement start points 12S, 13S.

Thus, all of the first to third measurement start points 11S to 13S and the first to third measurement end points 11E to 13E of the step gauge 10 can be touched and the positions thereof can be detected by the probe 46.

Measurement Process of CTE

Figure 24:
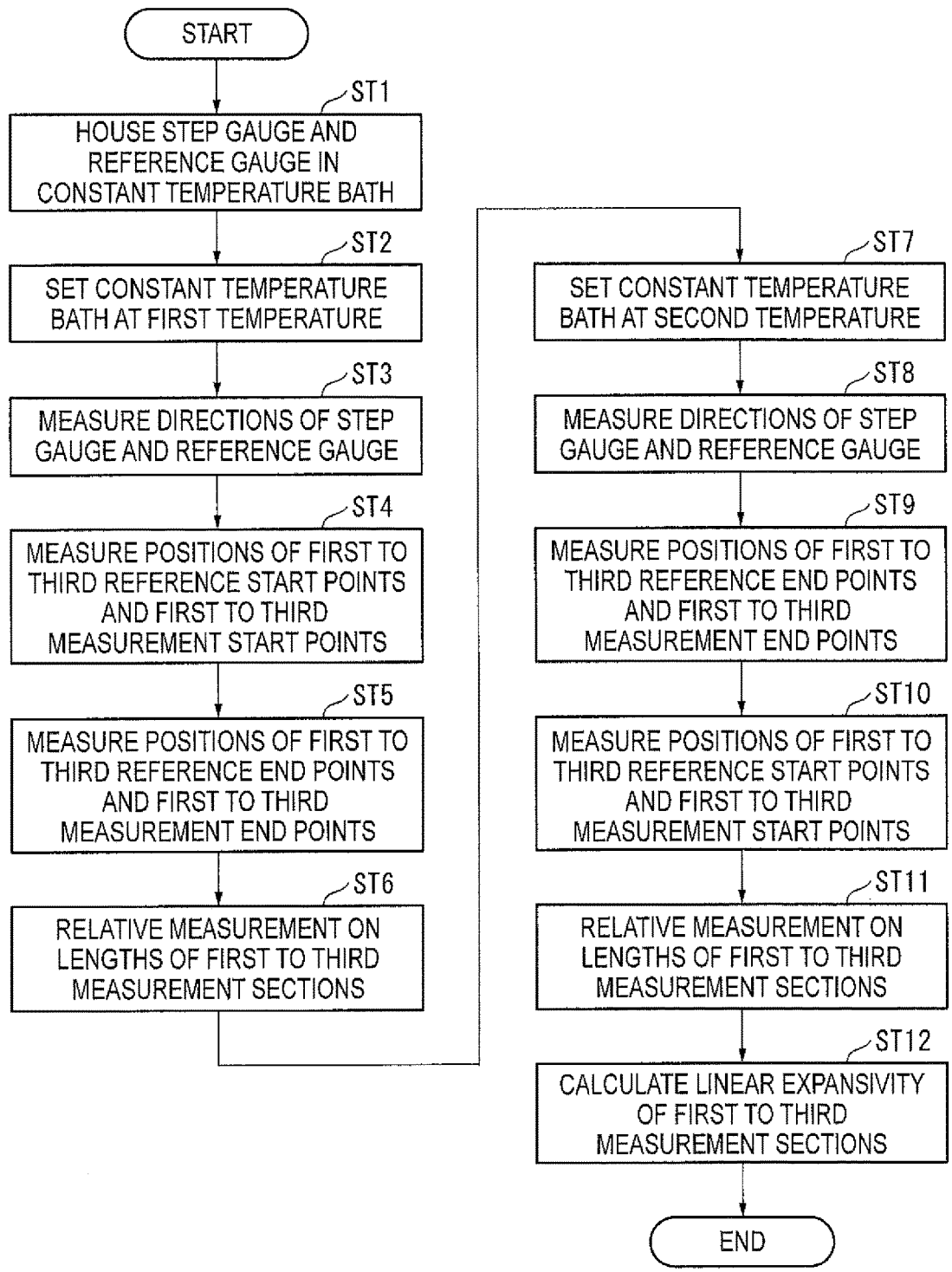
FIG. 24 is a flow chart showing a measurement process in the sixth exemplary embodiment.

FIG. 24 shows a measurement process of the CTE of the step gauge 10 using the CTE measuring device 1.

At the start of the measurement, the temperature-controlled chamber 30 is fixed on the coordinate measuring machine 40 to provide the CTE measuring device 1, and the step gauge 10 and the reference gauge block 20 are housed inside the temperature-controlled chamber 30 (Step ST1).

When the step gauge 10 and the reference gauge block 20 are set (Step ST1), all of the measurement apertures 31 are closed to set the temperature inside the temperature-controlled chamber 30 at the first temperature t1 and the temperature-controlled chamber 30 is left for a predetermined time to stabilize the temperature (Step ST2).

When the temperature is stabilized, one of the measurement apertures 31 nearest to the first to third measurement start points 11S to 13S is opened and the coordinate measuring machine 40 is driven to move and bring the probe 46 into contact with the upper face and lateral face of one of the protrusions 19 (not shielded by the reference gauge block 20) at the end on which the first to third measurement start points 11S to 13S are defined, so that positions of a plurality of points on the upper face and lateral face are detected to measure the direction of the step gauge 10 (an error between the drawing direction Lt and the Y-axis direction) (Step ST3).

Subsequently, the probe 46 is brought into contact with the first to third measurement start points 11S to 13S of the step gauge 10 to measure the positions of the first to third measurement start points 11S to 13S. Further, the probe 46 is brought into contact with the first to third reference start points 21S to 23S of the reference gauge block 20 to measure the positions of the first to third reference start points 21S to 23S (Step ST4).

Subsequently, the probe 46 is introduced through another one of the measurement apertures 31 and is sequentially brought into contact with the third measurement end point 13E of the step gauge 10, the third reference end point 23E of the reference gauge block 20, the second measurement end point 12E of the step gauge 10, the second reference end point 22E of the reference gauge block 20, the first measurement end point 11E of the step gauge 10 and the first reference end point 21E of the reference gauge block 20 to measure the positions of each of the end points (Step ST5).

Through the above measurement processes, the section lengths D11 to D13 of the first to third measurement sections S11 to S13 are calculated based on the positions of the first to third measurement start points 11S to 13S and the first to third measurement end points 11E to 13E. Further, the section lengths D21 to D23 of the first to third reference sections S21 to S23 are calculated based on the positions of the first to third reference start points 21S to 23S and the first to third reference end points 21E to 23E.

The first to third section lengths D21 to D23 of the reference gauge block 20 are highly accurately measured in advance. Accordingly, the relative measurement of the lengths of the measurement sections S11 to S13 of the step gauge 10 with reference to the reference sections S21 to S23 of the reference gauge block 20 can be performed by correcting the measured first to third section lengths D11 to D13 with the difference between the known values and the measured values of the section lengths D21 to D23 (Step ST6).

Subsequently, the temperature inside the temperature-controlled chamber 30 is set at the second temperature t2 and the temperature-controlled chamber 30 is left for a predetermined time to stabilize the temperature (Step ST7).

Then, in a manner similar to the Steps ST2 to ST6 in the measurement at the first temperature t1, Steps ST8, ST9, ST10 and ST11 are performed. The details of the Steps ST8 to ST11 are the same as those in the above-described Step ST2 to ST6 and thus duplicated description will be omitted.

CTEs α11 to α13 of the first to third measurement sections S11 to S13 can be obtained based on the first to third measurement section lengths D11 to D13 at the first temperature t1 and the first to third measurement section lengths D11 to D13 at the second temperature t2 obtained through the above processes.

Specifically, the CTE α11 can be represented by the formula below, where D11(t1) represents the first measurement length D11 at the first temperature t1, D11(t2) represents the first measurement length D11 at the second temperature t2 and D11 (nominal dimension) represents the nominal dimension of the first measurement section S11.

$$\alpha 11=(D11(t1)-D11(t2))/(D11\cdot(t1-t2))$$

In addition to the CTE α11 of the first measurement section S11, CTE α12 of the second measurement section S12 and CTE α13 of the third measurement section S13 can be obtained by similar calculations on the other sections S12 and S13 (Step ST12).

Advantages of Sixth Exemplary Embodiment

The above-described sixth exemplary embodiment offers the following advantages.

In the sixth exemplary embodiment, the CTEs α11 to α13 for the first to third measurement sections S11 to S13 (middle portions of the step gauge 10) can be calculated based on the first to third measurement lengths D11 to D13 at the first temperature t1 and the first to third measurement lengths D11 to D13 at the second temperature t2, thus efficiently measuring the CTE for each of the middle portions of the step gauge 10.

In the sixth exemplary embodiment, since the length of the step gauge 10 (measurement target) is measured using the coordinate measuring machine 40, the CTE of the step gauge 10 having various lengths can be highly accurately measured without using an expensive optical interferometer.

Further, the reference gauge block 20 is used as a length master and the relative measurement of the length with respect to the reference gauge block 20 is performed in measuring the length of the step gauge 10 using the coordinate measuring machine 40. Accordingly, the results of the length measurement are not dependent on the accuracy of the scale of the coordinate measuring machine 40 but are solely dependent on the accuracy of the reference gauge block 20. Thus, high accuracy of the measurement results can be ensured even when the length of the step gauge 10 is increased.

Further, since both of the reference gauge block 20 and the step gauge 10 are housed in the temperature-controlled chamber 30 in the sixth exemplary embodiment, it is only necessary to open/close the measurement apertures 31 of the temperature-controlled chamber 30 to introduce/take out the probe 46 in performing the relative measurement of the length of the measurement sections using the coordinate measuring machine 40. In other words, it is not necessary to open the temperature-controlled chamber 30 in order to exchange or take in/out the reference gauge block 20 during the time period from the relative measurement of each of the measurement sections at the first temperature t1 to the relative measurement of each of the measurement sections at the second temperature t2, so that the change in the temperature inside the temperature-controlled chamber 30 as well as the measurement time can be minimized.

In the sixth exemplary embodiment, since the insert holes 26, 27 are formed in the reference gauge block 20, even when the reference gauge block 20 is interposed between the step gauge 10 and the measurement apertures 31, the probe 46 can be introduced through the insert holes 26, 27, so that the positions of all of the measurement start points and the measurement end points can be reliably detected.

In the sixth exemplary embodiment, the reference gauge block 20 can be constructed by combining the plurality of existing gauge blocks 21 to 23. The reference sections S21 to S23 are respectively defined between end faces (i.e. the between the reference start points 21S to 23S and the reference end points 21E to 23E) of the plurality of gauge blocks 21 to 23. Accordingly, when the plurality of gauge blocks 21 to 23 are combined, the reference gauge block 20 can provide the reference sections S21 to S23 of the plurality of lengths. Thus, the reference gauge block 20 having the reference sections S21 to S23 with the plurality of lengths can be easily and inexpensively produced.

Further, since the plurality of the gauge blocks 21 to 23 are placed in a descending order of length thereof when being combined, the probe 46 introduced through one of the measurement apertures 31 can be brought into contact with all of the reference start points 21S to 23S and the reference end points 21E to 23E.

Seventh Exemplary Embodiment

Figure 25:
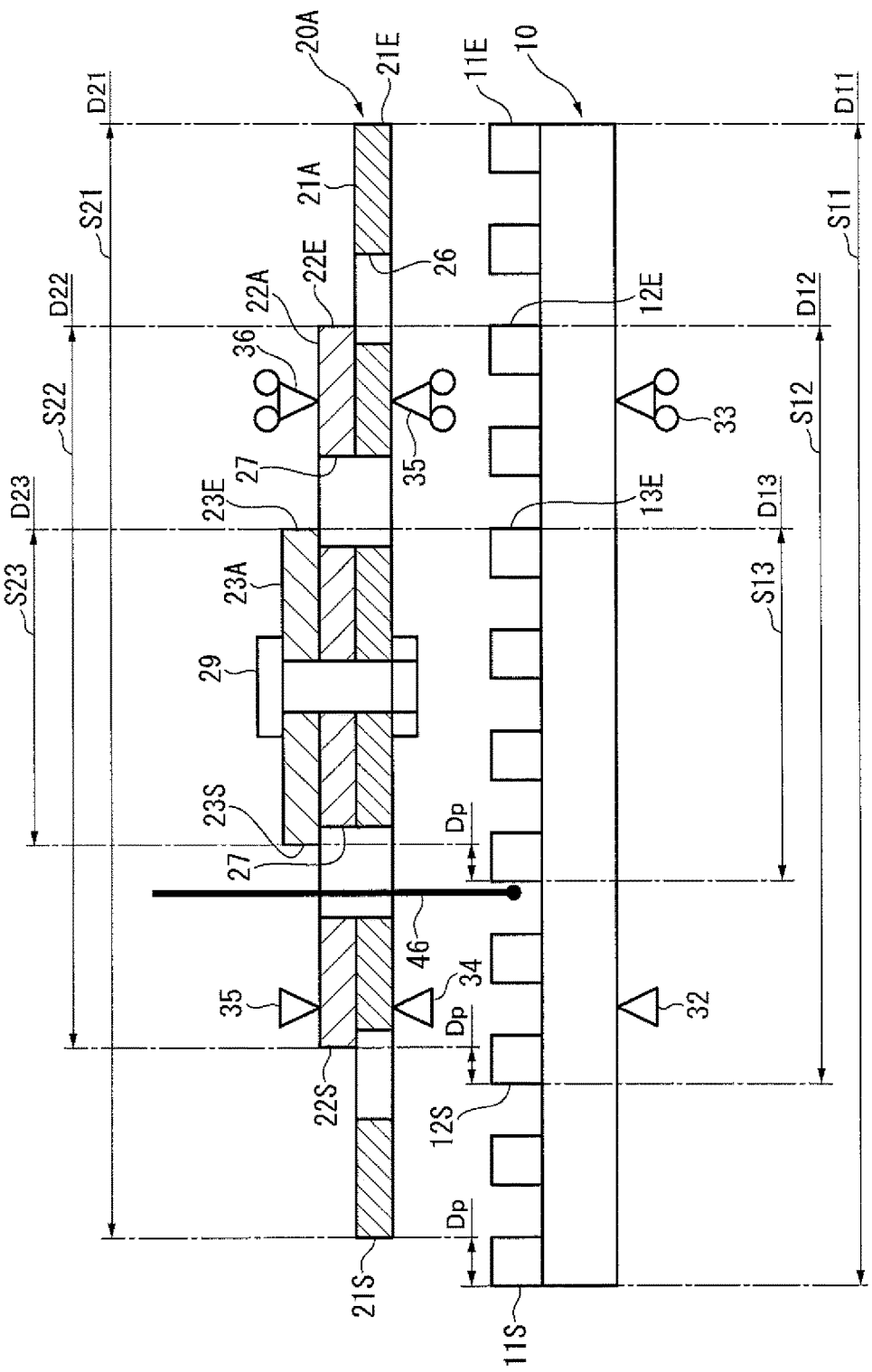
FIG. 25 is a side elevational view showing a reference gauge in a seventh exemplary embodiment of the invention.
Figure 26:
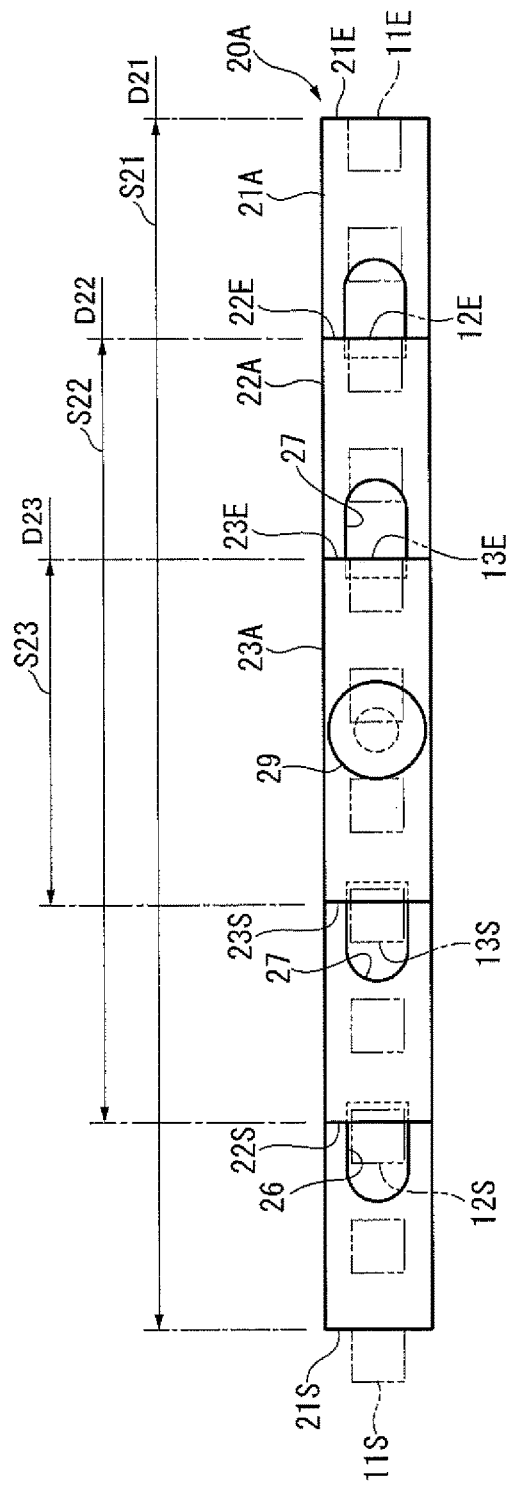
FIG. 26 is a plan view showing the reference gauge in the seventh exemplary embodiment.

FIGS. 25 and 26 show a reference gauge block 20A and the step gauge 10 of the seventh exemplary embodiment of the invention.

The components of the seventh exemplary embodiment including the CTE measuring device 1 are the same as those in the above-described sixth exemplary embodiment except for the reference gauge block 20A. Accordingly, only the different component(s) will be described below.

As shown in FIG. 21, the first to third reference sections S21 to S23 corresponding to the first to third measurement sections S11 to S13 are defined in order to measure the CTEs of the first measurement section S11 (between right and left ends of the step gauge 10 in the figure) and the second and the third measurement sections S12 and S13 (from the left end to the middle points in the figure) in the above-described sixth exemplary embodiment. Further, the reference gauge block 20 is constructed by combining the three gauge blocks 21 to 23 in a manner that the first to third reference start points 21S to 23S are aligned.

In contrast, though the reference gauge block 20A according to the seventh exemplary embodiment includes the three similar gauge blocks 21A to 23A, the gauge blocks 21A to 23A are constructed without aligning the first to third reference start point 21S to 23S when being combined.

As shown in FIG. 25, central parts of the measurement sections S11 to S13 of the step gauge 10 in the seventh exemplary embodiment are aligned (i.e. "nested").

In order to arrange the reference sections S21 to S23 of the reference gauge block 20A in accordance with the measurement sections S11 to S13, central parts of the gauge blocks 21A to 23A are mutually layered.

The three gauge blocks 21A, 22A, 23A are fastened by the fixture 29 provided at the center. The gauge blocks 21A to 23A are not necessarily fastened by the fixture 29 but may be rigidly attached while being layered by other mechanism (s) such as mutual bonding and bundling with a use of a belt-shaped member.

The gauge blocks 21A, 22A are provided with two insert holes 27 in communication with each other. The gauge block 21A is provided with the insert holes 26 at two positions.

The seventh exemplary embodiment offers the same advantages as those mentioned in the above-described sixth exemplary embodiment through the measurement processes similar to those in the sixth exemplary embodiment.

As described above, according to the above aspect of the invention, desired section of the step gauge 10 and the CTE thereof can be measured by selective use of the reference gauge blocks 20, 20A.

Eighth Exemplary Embodiment

Figure 27:
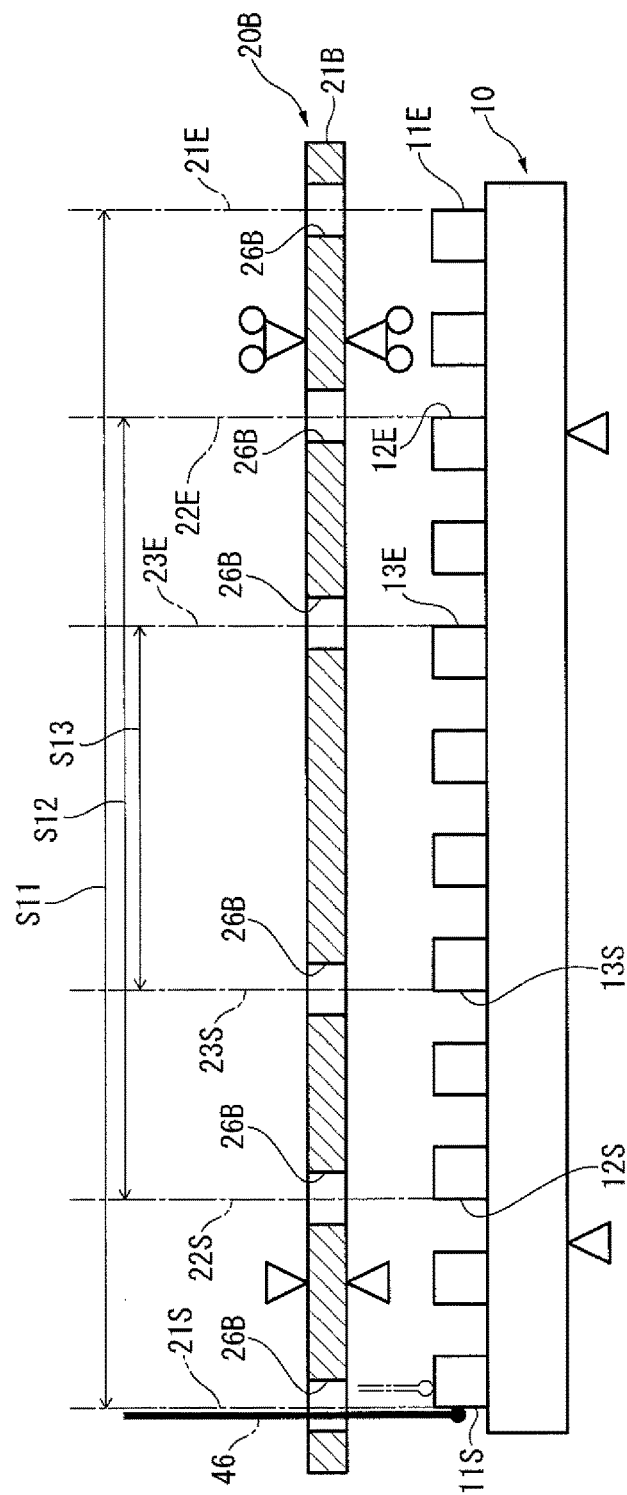
FIG. 27 is a side elevational view showing a reference gauge in an eighth exemplary embodiment of the invention.
Figure 28:
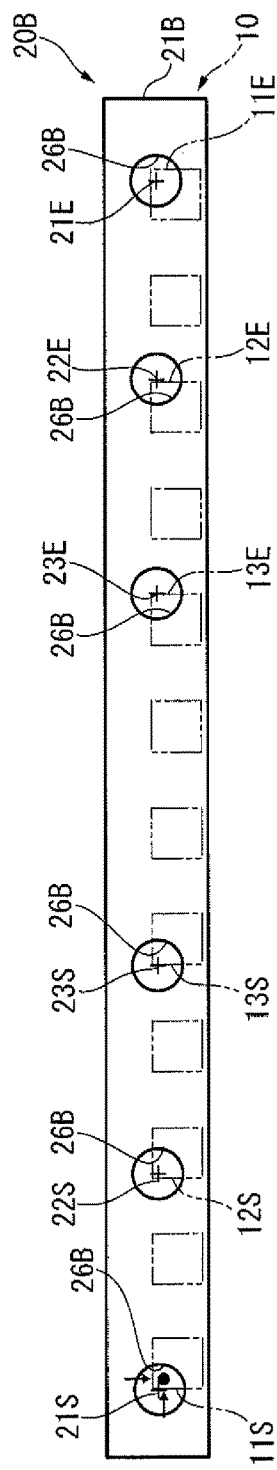
FIG. 28 is a plan view showing the reference gauge in the eighth exemplary embodiment.

FIGS. 27 and 28 show a reference gauge block 20B and the step gauge 10 of the eighth exemplary embodiment of the invention.

The components of the eighth exemplary embodiment including the CTE measuring device 1 are the same as those in the above-described sixth exemplary embodiment except for the reference gauge block 20B. Accordingly, only the different component(s) will be described below.

In the above-described sixth exemplary embodiment, the three gauge blocks 21 to 23 are combined to provide the reference gauge block 20 and the first to third reference start points 21S to 23S and the first to third reference end points 21E to 23E are defined on the end faces of each of the gauge blocks 21 to 23.

In contrast, the reference gauge block 20B in the eighth exemplary embodiment includes a single gauge block 21B provided with a plurality of insert holes 26B. In the eighth exemplary embodiment, the insert holes 26B also serves as the hole to be detected and central axis positions of the insert holes 26B define the first to third reference start points 21S to 23S and the reference end points 21E to 23E.

The gauge block 21B is a component similar to the gauge block 21 in the above-described sixth exemplary embodiment.

The insert hole 26B also serving as hole to be detected is provided at six points in the gauge block 21B.

Three left (in FIG. 27) insert holes 26B are set at positions to be defined as the first to third reference start points 21S to 23S, in other words, at positions corresponding to the first to third measurement start points 11S to 13S of the step gauge 10 (the measurement target).

In contrast, three right (in FIG. 27) insert holes 26B are set at positions to be defined as the first to third reference end points 21E to 23E, in other words, at positions corresponding to the first to third measurement end points 11E to 13E of the step gauge 10 (the measurement target).

In the eighth exemplary embodiment, the probe 46 is brought into contact with three or more points on the inner circumference of each of the six insert holes 26B also serving as the hole to be detected to measure the position of the central axis of each of the insert holes 26B, i.e. the first to third reference start points 21S to 23S and the first to third reference end points 21E to 23E.

Further, the probe 46 can be brought into contact with the first to third measurement start points 11S to 13S and the first to third measurement end points 11E to 13E of the step gauge 10 to measure the positions thereof through the six insert holes 26B also serving as the hole to be detected.

Accordingly, the reference section lengths of the reference gauge block 20B can be measured and the relative measurement of the measurement section lengths of the step gauge 10 can be performed based on the measurements of the above points, thereby achieving the same advantages as those in the above-described sixth exemplary embodiment through the same measurement processes as those in the above-described sixth exemplary embodiment.

It should be noted that, in the eighth exemplary embodiment, one of the protrusions 19 of the step gauge 10 defined with the first measurement start point 11S is disposed so that the end face defined with the first measurement start point 11S, one of the lateral faces and the upper face appear in an opening area of one of the insert holes 26B of the reference gauge block 20B.

With the above arrangement, the probe 46 can be inserted from above into the one of the insert holes 26B to bring the probe 46 into contact with the end face, the lateral face and the upper face of the one of the protrusions 19 to detect the positions of the end face, the lateral face and the upper face and measure the orientation of the step gauge 10 (an error between the drawing direction Lt and the Y-axis direction) (Step ST3 in the sixth exemplary embodiment in FIG. 24).

The same applies to the below-described ninth and tenth exemplary embodiment.

Ninth Exemplary Embodiment

Figure 29:
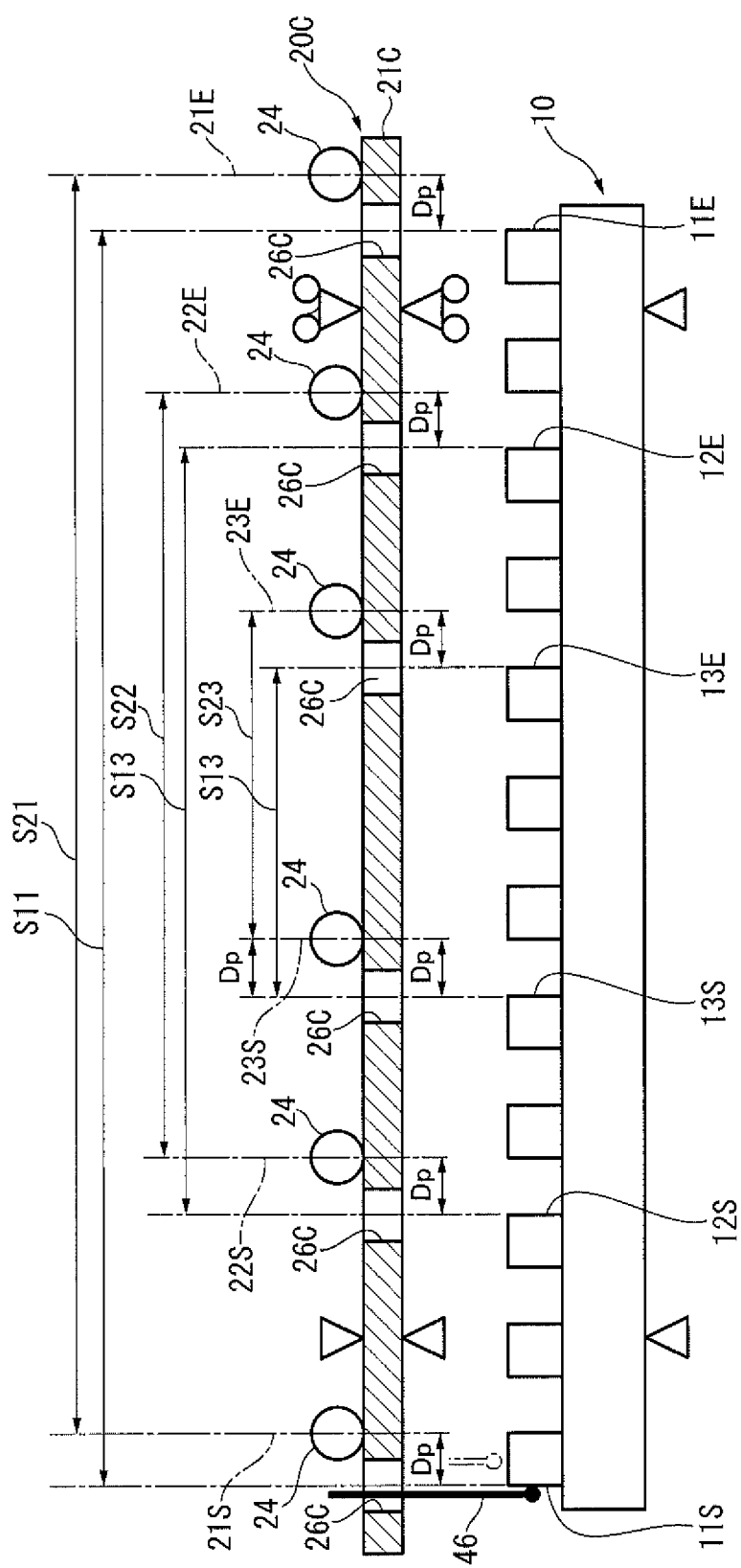
FIG. 29 is a side elevational view showing a reference gauge in a ninth exemplary embodiment of the invention.
Figure 30:
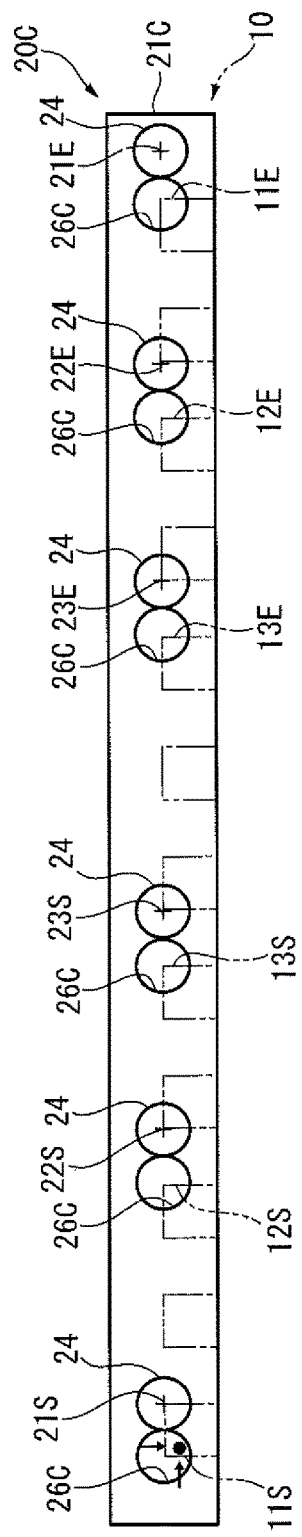
FIG. 30 is a plan view showing the reference gauge in the ninth exemplary embodiment.

FIGS. 29 and 30 show a reference gauge block 20C and the step gauge 10 of the ninth exemplary embodiment of the invention.

The components of the ninth exemplary embodiment including the CTE measuring device 1 are the same as those in the above-described sixth exemplary embodiment except for the reference gauge block 20C. Accordingly, only the different component(s) will be described below.

In the above-described sixth exemplary embodiment, the three gauge blocks 21 to 23 are combined to provide the reference gauge block 20 and the first to third reference start points 21S to 23S and the first to third reference end points 21E to 23E are defined on the end faces of each of the gauge blocks 21 to 23.

In contrast, the reference gauge block 20C of the ninth exemplary embodiment includes a single gauge block 21C provided with a plurality of insert holes 26C, and six balls 24 to be measured fixed on the surface of the gauge block 21C near the insert holes 26C. Axis lines each passing through the center of each of the balls 24 and orthogonal to the gauge block 21C define the first to third reference start points 21S to 23S and the reference end points 21E to 23E.

The balls 24 are exemplarily made of the same material as that of the gauge block 21C and each have a highly accurately finished spherical surface. The balls 24 are fixed on the gauge block 21C by an adhesive or the like with the position thereof being determined by a conical hole provided on the surface of the gauge block 21C.

In the ninth exemplary embodiment, the probe 46 is brought into contact with four or more points on the spherical surface of each of the balls 24 to measure the positions of the axis lines showing the center of each of the balls 24 and the first to third reference start points 21S to 23S and the first to third reference end points 21E to 23E.

Further, the probe 46 can be brought into contact with the first to third measurement start points 11S to 13S and the first to third measurement end points 11E to 13E of the step gauge 10 to measure the positions thereof through the insert holes 26C.

Accordingly, the reference section lengths of the reference gauge block 20C can be measured and the relative measurement of the measurement section lengths of the step gauge 10 can be performed based on the measurements of the above points, thereby achieving the same advantages as those in the above-described sixth exemplary embodiment through the same measurement processes as those in the above-described sixth exemplary embodiment.

Tenth Exemplary Embodiment

Figure 31:
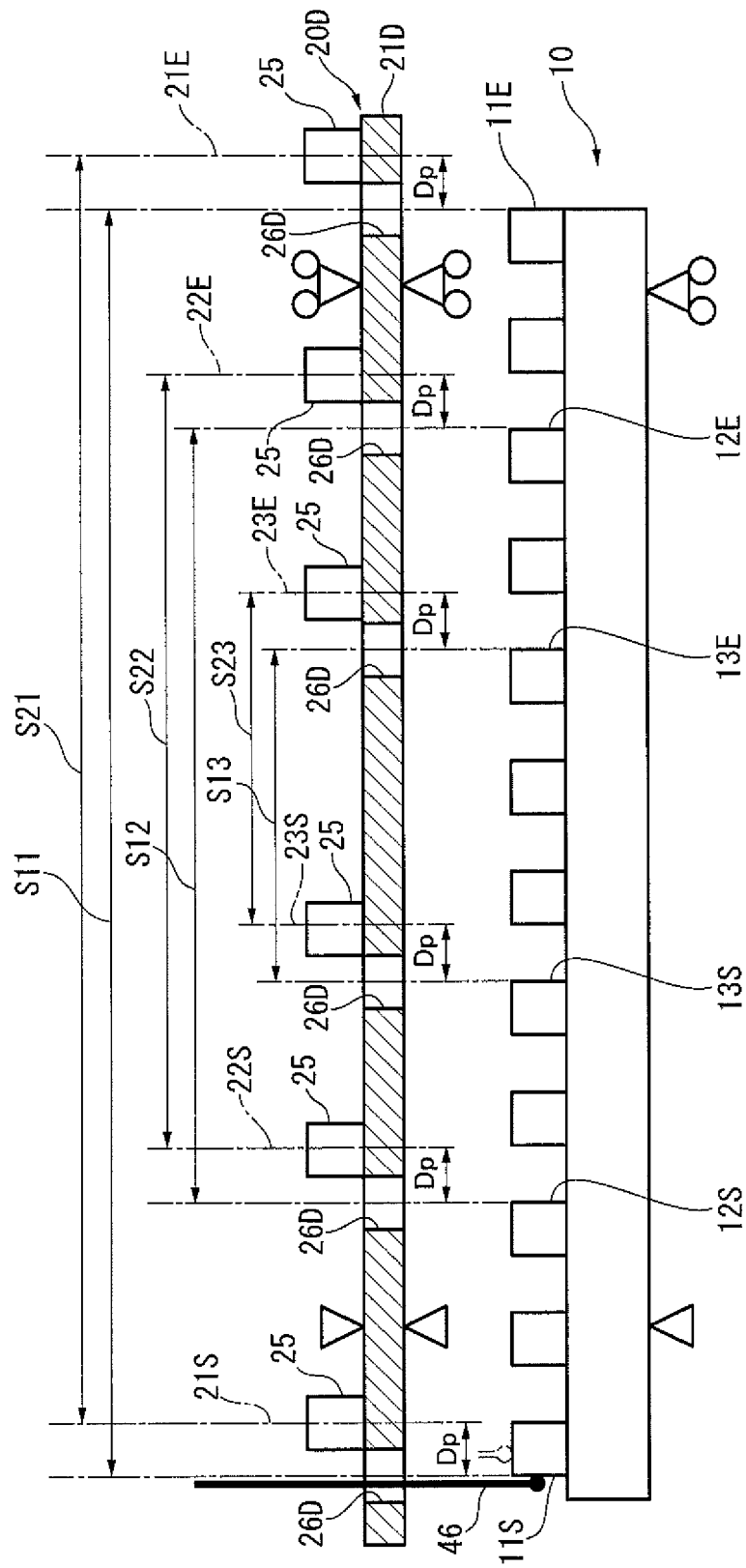
FIG. 31 is a side elevational view showing a reference gauge in a tenth exemplary embodiment of the invention.
Figure 32:
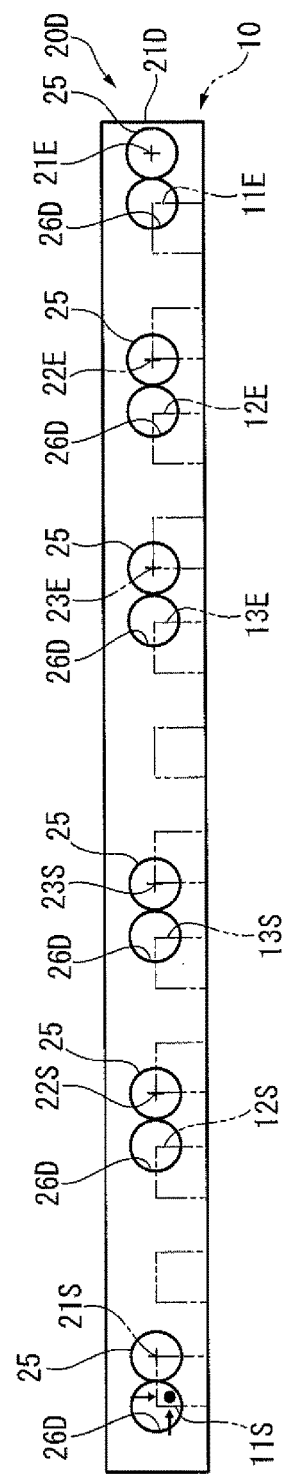
FIG. 32 is a plan view showing the reference gauge in the tenth exemplary embodiment.

FIGS. 31 and 32 show a reference gauge block 20D and the step gauge 10 of the tenth exemplary embodiment of the invention.

The components of the tenth exemplary embodiment including the CTE measuring device 1 are the same as those in the above-described sixth exemplary embodiment except for the reference gauge block 20D. Accordingly, only the different component(s) will be described below.

In the above-described sixth exemplary embodiment, the three gauge blocks 21 to 23 are combined to provide the reference gauge block 20 and the first to third reference start points 21S to 23S and the first to third reference end points 21E to 23E are defined on the end faces of each of the gauge blocks 21 to 23.

In contrast, the reference gauge block 20D of the tenth exemplary embodiment includes a single gauge block 21D provided with a plurality of insert holes 26D, and six cylinders 25 to be measured fixed on the surface of the gauge block 21D near the insert holes 26D. Central axis of the cylinders 25 define the first to third reference start points 21S to 23S and the reference end points 21E to 23E.

The cylinders 25 are exemplarily made of the same material as that of the gauge block 21D and each have highly accurately finished outer circumferential cylindrical surface. The cylinders 25 are fixed on predetermined positions on the surface of the gauge block 21D using an adhesive or the like.

In the tenth exemplary embodiment, the probe 46 is brought into contact with three or more points on the cylindrical surface of each of the cylinders 25 to measure the positions of the axis lines showing the center of each of the cylinders 25 (i.e. the first to third reference start points 21S to 23S and the first to third reference end points 21E to 23E).

Further, the probe 46 can be brought into contact with the first to third measurement start points 11S to 13S and the first to third measurement end points 11E to 13E of the step gauge 10 to measure the positions thereof through the insert holes 26D.

Accordingly, the reference section lengths of the reference gauge block 20D can be measured and the relative measurement of the measurement section lengths of the step gauge 10 can be performed based on the measurements of the above points, thereby achieving the same advantages as those in the above-described sixth exemplary embodiment through the same measurement processes as those in the above-described sixth exemplary embodiment.

Eleventh Exemplary Embodiment

Measurement Target and Reference Gauge

Figure 33:
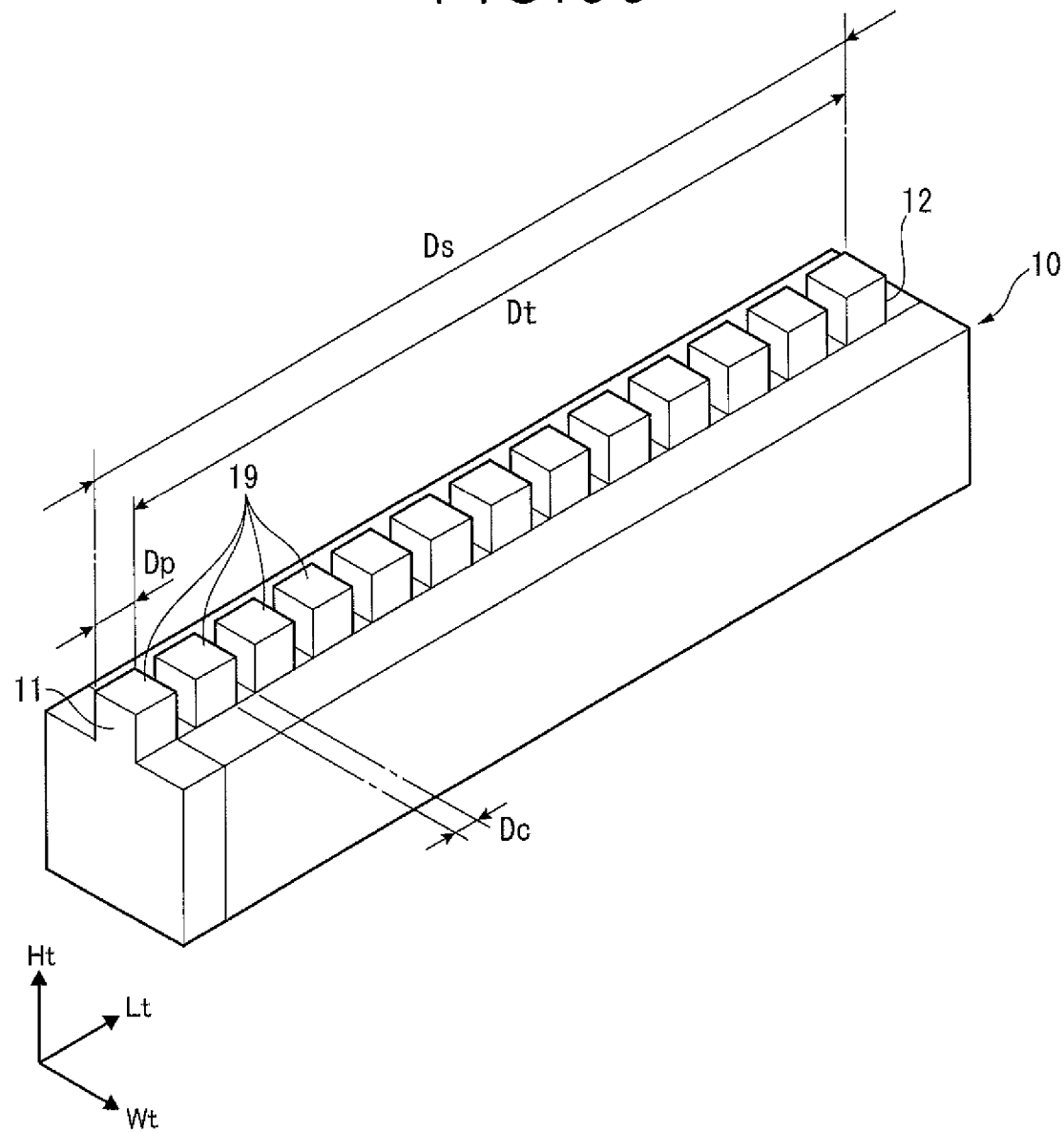
FIG. 33 is a perspective view showing a step gauge (a measurement target in an eleventh exemplary embodiment of the invention).

FIG. 33 shows a step gauge 10 (measurement target) in an eleventh exemplary embodiment.

A length Ds of the step gauge 10 is defined by a distance between the first surface 11 of one of the protrusions 19 on the first end and the second surface 12 of the other one of the protrusions 19 on the second end of the step gauge 10.

In the eleventh exemplary embodiment, a measurement target section is defined at a section whose length Dt is shorter than the length Ds by the dimension of one of the protrusions 19 (i.e. the length Dt=Ds−Dp).

Figure 34:
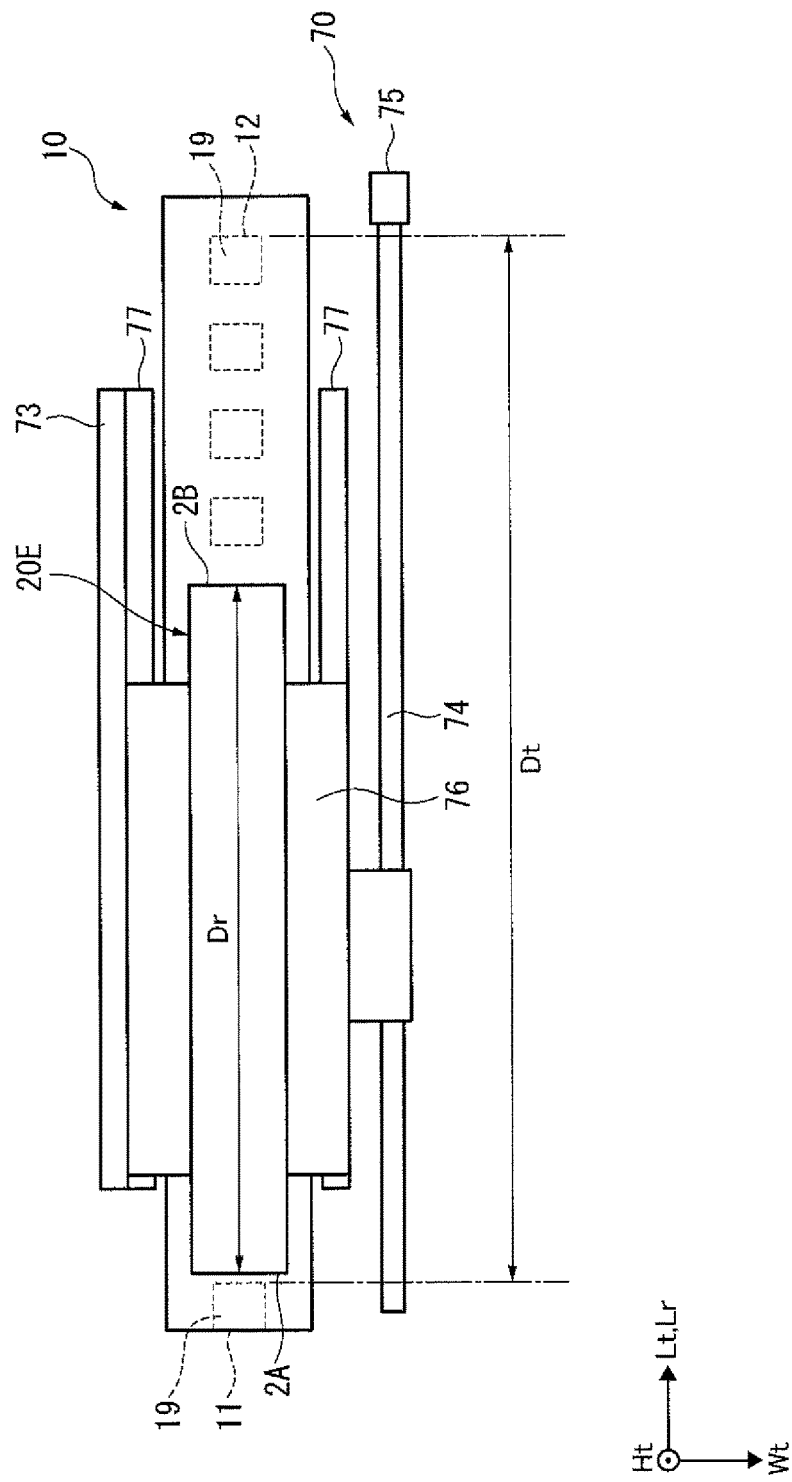
FIG. 34 is a plan view showing the reference gauge in the eleventh exemplary embodiment.
Figure 35:
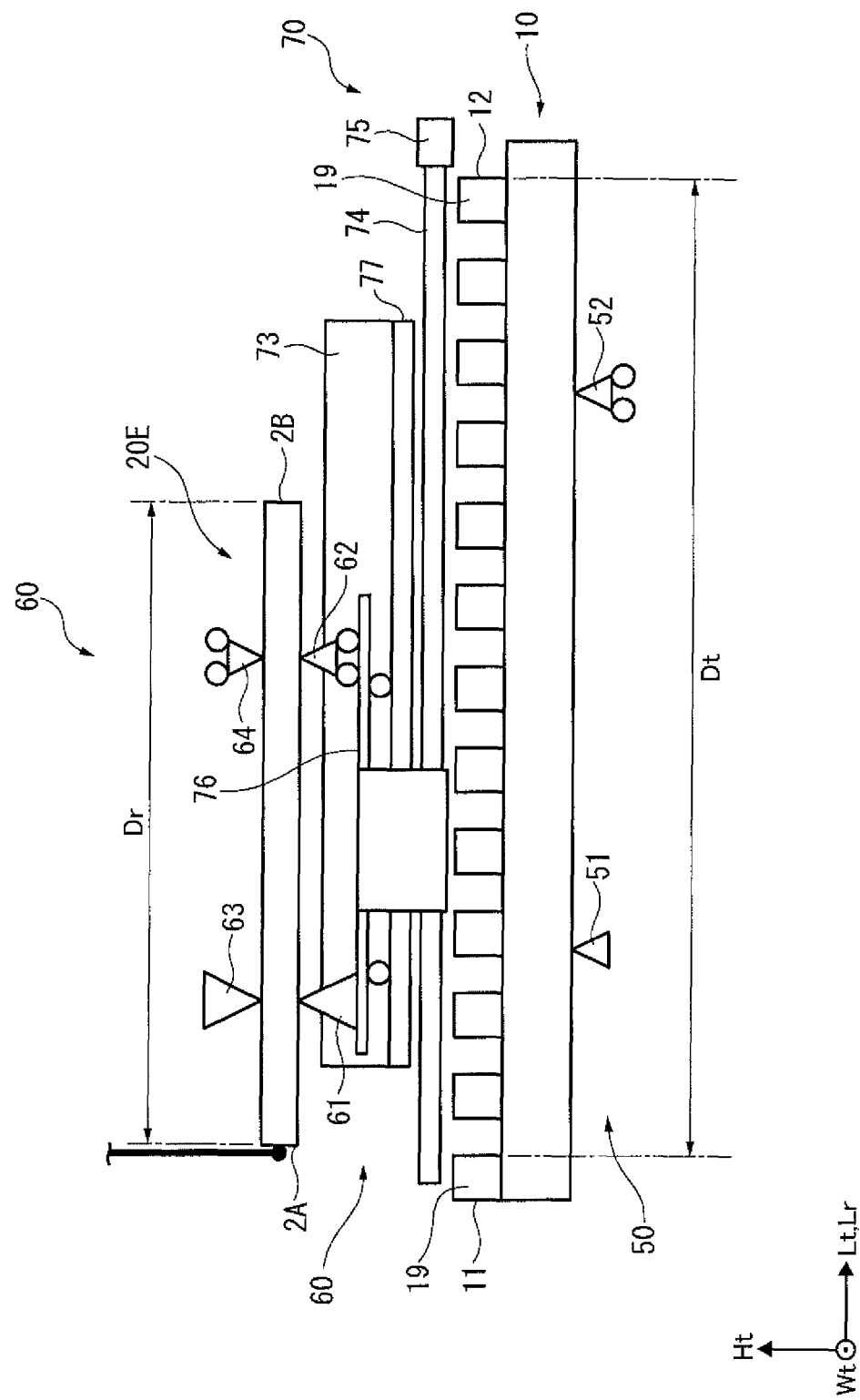
FIG. 35 is a side elevational view showing the reference gauge in the eleventh exemplary embodiment.

As shown in FIGS. 34 and 35, the reference gauge block 20E (the reference gauge) is an elongated gauge block extending in the drawing direction Lr. A top face, bottom face and lateral faces of the reference gauge block 20E are each parallel to one of the vertical direction Ht and the width direction Wt of the step gauge 10.

The first reference surface 2A and the second reference surface 2B of the reference gauge block 20E are defined by a pair of end faces at both ends in the drawing direction Lr. A reference gauge length Dr is defined by the distance between the first reference surface 2A and the second reference surface 2B.

The reference gauge block 20E is made of a material of extremely low expansion coefficient or a material of zero expansion coefficient whose expansion due to the temperature change between the first temperature t1 and the second temperature t2 (described later) is below a detectable limit. It should be noted that the reference gauge block 20E may be made of a material whose expansion coefficient is known.

The step gauge 10 and the reference gauge block 20E are placed in the temperature-controlled chamber 30 in parallel with each other.

In order to support the step gauge 10 and the reference gauge block 20E, the measurement target support base 50 and the reference gauge support base 60 as shown in FIG. 35 are placed in the temperature-controlled chamber 30.

The measurement target support base 50 includes the first measurement target support base 51 configured to support the lower face of the step gauge 10 near the first surface 11 and the second measurement target support base 52 configured to support the lower face of the step gauge 10 near the second surface 12.

The first measurement target support base 51 is configured to restrict the displacement of the step gauge 10 in the drawing direction Lt, whereas the second measurement target support base 52 is configured to permit the displacement of the step gauge 10 in the drawing direction Lt.

The reference gauge support base 60 includes the first reference gauge support base 61 configured to support the lower face of the step gauge 10 near the first reference surface 2A and the second reference gauge support base 62 configured to support the lower face of the step gauge 10 near the second reference surface 2B.

Further, the reference gauge support base 60 includes a first pressing portion 63 configured to push the upper face of the step gauge 10 to press the step gauge 10 against the first reference gauge support base 61, and a second pressing portion 64 configured to push the upper face of the step gauge 10 to press the step gauge 10 against the second reference gauge support base 62.

The first reference gauge support base 61 and the first pressing portion 63 are configured to restrict the displacement of the step gauge 10 in the drawing direction Lt, whereas the second reference gauge support base 62 and the second pressing portion 64 are configured to permit the displacement of the step gauge 10 in the drawing direction Lt.

All of the first reference gauge support base 61, the second reference gauge support base 62, the first pressing portion 63 and the second pressing portion 64 are supported by a movable base 76.

The movable base 76 is horizontally movable on a pair of rails 77 via rollers with a movement direction thereof being restricted by a guide rail 73 provided along a lateral face of the movable base 76, so that the movable base 76 is configured to move along the drawing directions Lt, Lr.

Further, a ball screw mechanism 74 is connected to the movable base 76. The ball screw mechanism 74 is driven by a motor 75 to move the movable base 76 and the reference gauge block 20E to a desired position along the drawing directions Lt, Lr.

The movable base 76, the rail 77, the guide rail 73, the ball screw mechanism 74 and the motor 75 define a reference gauge drive mechanism 70.

Allocation of Relative Measurement Section

In the eleventh exemplary embodiment, a plurality of relative measurement sections corresponding to the reference gauge block 20E (length Dr) are allocated to the measurement target section (length Dt) of the step gauge 10.

The relative measurement section is allocated to the measurement target section as follows. Initially, the reference gauge block 20E whose length (reference gauge length Dr) is in an integer ratio to the measurement target section length Dt is used. A fraction dividing the difference between the measurement target section length Dt and the reference gauge length Dr by an integer is defined as a shift amount Dd. Then, an allocated number n, which is larger by one than a division of the difference between the measurement target section length Dt and the reference gauge length Dr by the shift amount Dd, of the relative measurement sections are allocated to the measurement target section.

Specifically, for the reference gauge length Dr and the allocated number n of the relative measurement section, the shift amount Dd=(Dt−Dr)/(n−1) and the measurement target section length Dt=Dr+(n−1)·Dd.

As mentioned above, the measurement target section each having the length Dt is allocated with the n relative measurement sections having the length Dr, where start points of each of the relative measurement sections are sequentially shifted by the shift amount Dd.

The start point of an nth relative measurement section Mn is defined at the point displaced from the start point of the measurement target section (position P0) by the length of (n−1) shift amounts Dd. The end point of the nth relative measurement section is defined at a point displaced from the start point of the measurement target section by the length Dr+(n−1)·Dd.

As a specific example, when the measurement target section length Dt of the step gauge 10=1500 mm in the eleventh exemplary embodiment, the reference gauge block 20E may have the reference gauge length Dr=1000 mm (ratio 3:2).

The fraction of the difference 500 mm by an integer (the shift amount Ds) may be 250 mm (½), and the allocated number n may be defined as (500/250)+1=3.

Figure 36:
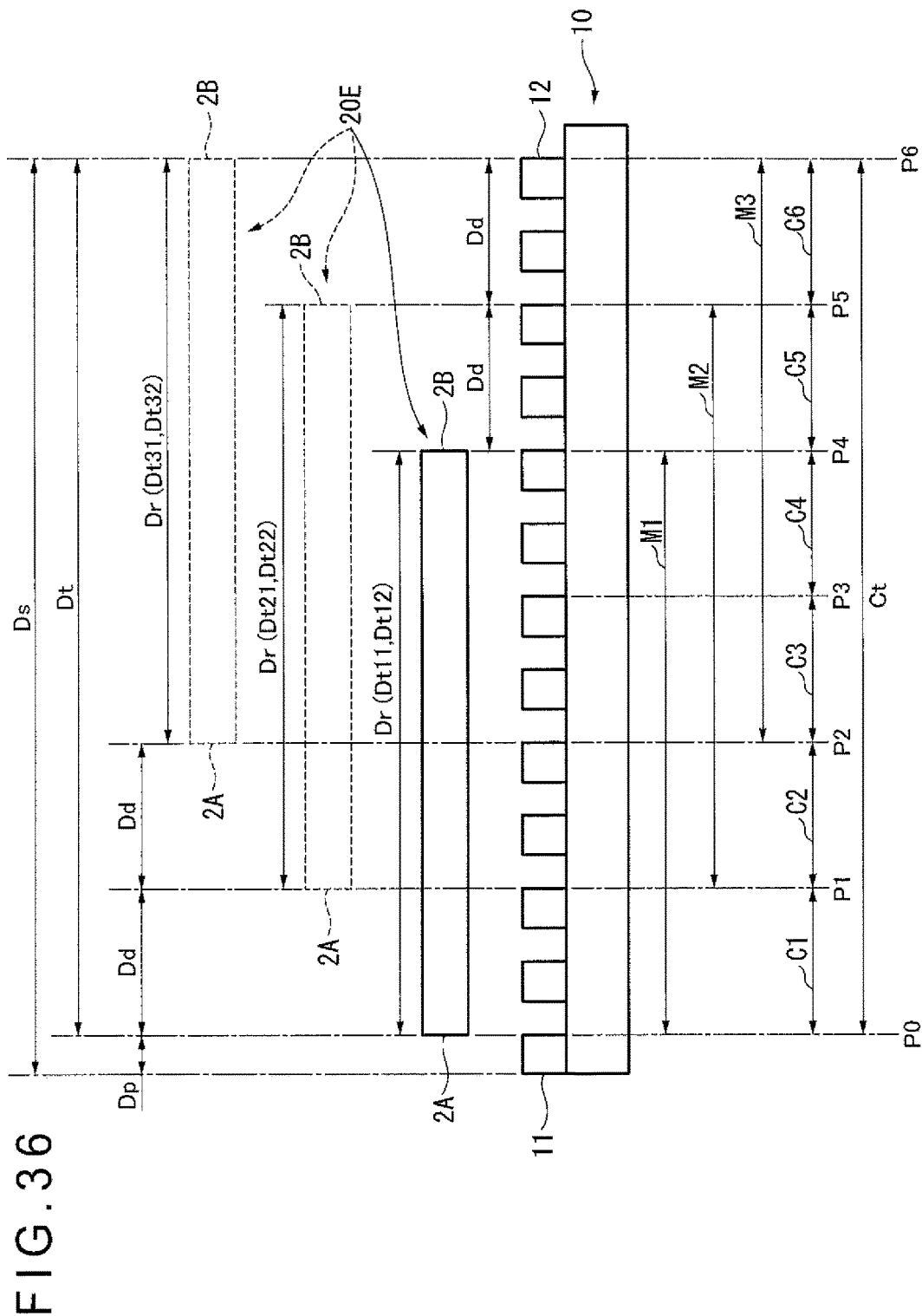
FIG. 36 is a schematic illustration of a measurement condition in the eleventh exemplary embodiment.

FIG. 36 shows an arrangement of the relative measurement sections in the eleventh exemplary embodiment.

The start point of a first relative measurement section M1 coincides with the start point (position P0) of the measurement target section. The end point of the first relative measurement section M1 is defined at a position P4 remote from the start point of the measurement target section by the length Dr.

The start point of a second relative measurement section M2 is defined at a position P1 shifted from the start point of the measurement target section (position P0) by the shift amount Dd. The end point of the second relative measurement section M2 is defined at a position P5 remote from the start point of the measurement target section by the length Dr+1·Dd.

The start point of a third relative measurement section M3 is defined at a position P2 shifted from the start point of the measurement target section (position P0) by the length of two shift amounts Dd. The end point of the third relative measurement section M3 is defined at a position P6 remote from the start point of the measurement target section by the length Dr+2·Dd.

As described above, in the eleventh exemplary embodiment, the relative measurement sections M1 to M3 are arranged at sections each shifted by the shift amount Dd, where the relative measurement sections M1 to M3 are overlapped with each other defining sections for the shift amount Dd.

Accordingly, section CTE for each of the relative measurement sections can be calculated for each of the sections of the shift amount Dd, so that the efficiency of the calculation process can be enhanced.

Specifically, in the eleventh exemplary embodiment, after calculating the section CTEs $\alpha 1$ to $\alpha 3$ for respective relative measurement sections, the average of the section CTEs $\alpha 1$ to $\alpha 3$ of the relative measurement sections partially overlapped for each of the sections with the length Dd can be obtained, thereby highly accurately and reliably obtaining the CTE $\alpha$ of the entire measurement target section with the use of the section CTEs $\alpha 1$ to $\alpha 3$ for respective measurement sections.

For the above purpose, in the eleventh exemplary embodiment, a plurality of count sections are allocated in the series of the measurement target sections.

Allocation of Count Section

In order to calculate the CTE $\alpha$ of the entire measurement target section (length Dt) in the eleventh exemplary embodiment, a plurality of count sections Cn delimited for every shift amount Dd are allocated in the measurement target section. Further, each of the count sections Cn is assigned with a weight coefficient c based on a ratio of the length of each of the count sections Cn with respect to the length Dt of the measurement target section. It should be noted that, when the lengths of the count sections Cn are the same, the weight coefficient c is the same for all of the count sections Cn.

Thus defined count sections Cn allow a calculation of an average CTEs $\alpha$n ($\alpha$1 to $\alpha$3 in the eleventh exemplary embodiment) of the relative measurement sections (M1 to M3 in the eleventh exemplary embodiment) allocated to each of the count sections Cn (i.e. overlapped in the same count section Cn).

Further, by calculating a product c·$\alpha$n of the average $\alpha$n of the section CTE and the weight coefficient c for each of the count sections Cn and totalizing the products c·$\alpha$n of all the count sections Cn, the CTE $\alpha$ of the entire measurement target section can be calculated.

As shown in FIG. 36, six count sections C1 to C6 are allocated in the eleventh exemplary embodiment.

Three relative measurement sections M1 to M3 are defined in the measurement target section Dt in the eleventh exemplary embodiment, each of the relative measurement sections M1 to M3 being shifted by the shift amount Dd and having the length Dr four times larger than the shift amount Dd. Accordingly, the measurement target section Dt can be divided into the six count sections C1 to C6 each having the length corresponding to the shift amount Dd.

The first count section C1 is defined at a section having the length Dd between the start point of the first relative measurement section M1 (position P0) and the start point of the second relative measurement section M2 (position P1). Only the first relative measurement section M1 is allocated to the count section C1.

The second count section C2 is defined at a section having the length Dd between the start point of the second relative measurement section M2 (position P1) and the start point of the third relative measurement section M3 (position P2). The first relative measurement section M1 and the second relative measurement section M2 are both allocated to the count section C2 in an overlapping manner.

The third count section C3 is defined at a section having the length Dd between the start point of the third relative measurement section M3 (position P2) and the middle point of the measurement target section (position P3). All of the first relative measurement section M1, the second relative measurement section M2 and the third relative measurement section M3 are allocated to the count section C3 in an overlapping manner.

The fourth count section C4 is defined at a section having the length Dd between the middle point of the measurement target section (position P3) and the end point of the first relative measurement section (position P4). All of the first relative measurement section M1, the second relative measurement section M2 and the third relative measurement section M3 are allocated to the count section C4 in an overlapping manner.

The fifth count section C5 is defined at a section having the length Dd between the end point of the first relative measurement section M1 (position P4) and the end point of the second relative measurement section M2 (position P5). The second relative measurement section M2 and the third relative measurement section M3 are both allocated to the count section C5 in an overlapping manner.

The sixth count section C6 is defined at a section having the length Dd between the end point of the second relative measurement section M2 (position P5) and the end point of the third relative measurement section M3 (position P6). Only the third relative measurement section M3 is allocated to the count section C6.

The length Dd of each of the first to sixth count sections C1 to C6 is one sixth of the length Dr (length Dd=Dr/6). Accordingly, the weight coefficient c of each of the count sections C1 to C6 is defined as one sixth (weight coefficient c=⅙).

With the count sections C1 to C6 as defined above, the CTE $\alpha$ of the entire measurement target section can be highly accurately and reliably calculated by: calculating the section CTEs $\alpha$1 to $\alpha$3 for the relative measurement sections M1 to M3; subsequently calculating the average $\alpha$n of the section CTEs $\alpha$1 to $\alpha$3 of the relative measurement sections M1 to M3 overlapping at each of the count sections C1 to C6 for every length Dd; multiplying the average $\alpha$n of the section CTEs of the relative measurement sections by the weight coefficient c of the respective count section (i.e. c=⅙ corresponding to the six sections in the above instances); and totalizing the products c·$\alpha$n of all of the count sections.

Specifically, the CTE $\alpha$ can be calculated as follows:

$$\alpha = (1/6)(\alpha 1) \ldots \text{ for count section } C1 +$$
$$(1/6)(\alpha 1 + \alpha 2)/2 \ldots \text{ for count section } C2 +$$
$$(1/6)(\alpha 1 + \alpha 2 + \alpha 3)/3 \ldots \text{ for count section } C3 +$$
$$(1/6)(\alpha 1 + \alpha 2 + \alpha 3)/3 \ldots \text{ for count section } C4 +$$
$$(1/6)(\alpha 2 + \alpha 3)/2 \ldots \text{ for count section } C5 +$$
$$(1/6)(\alpha 3) \ldots \text{ for count section } C6$$

Measurement Process of CTE

Figure 37:
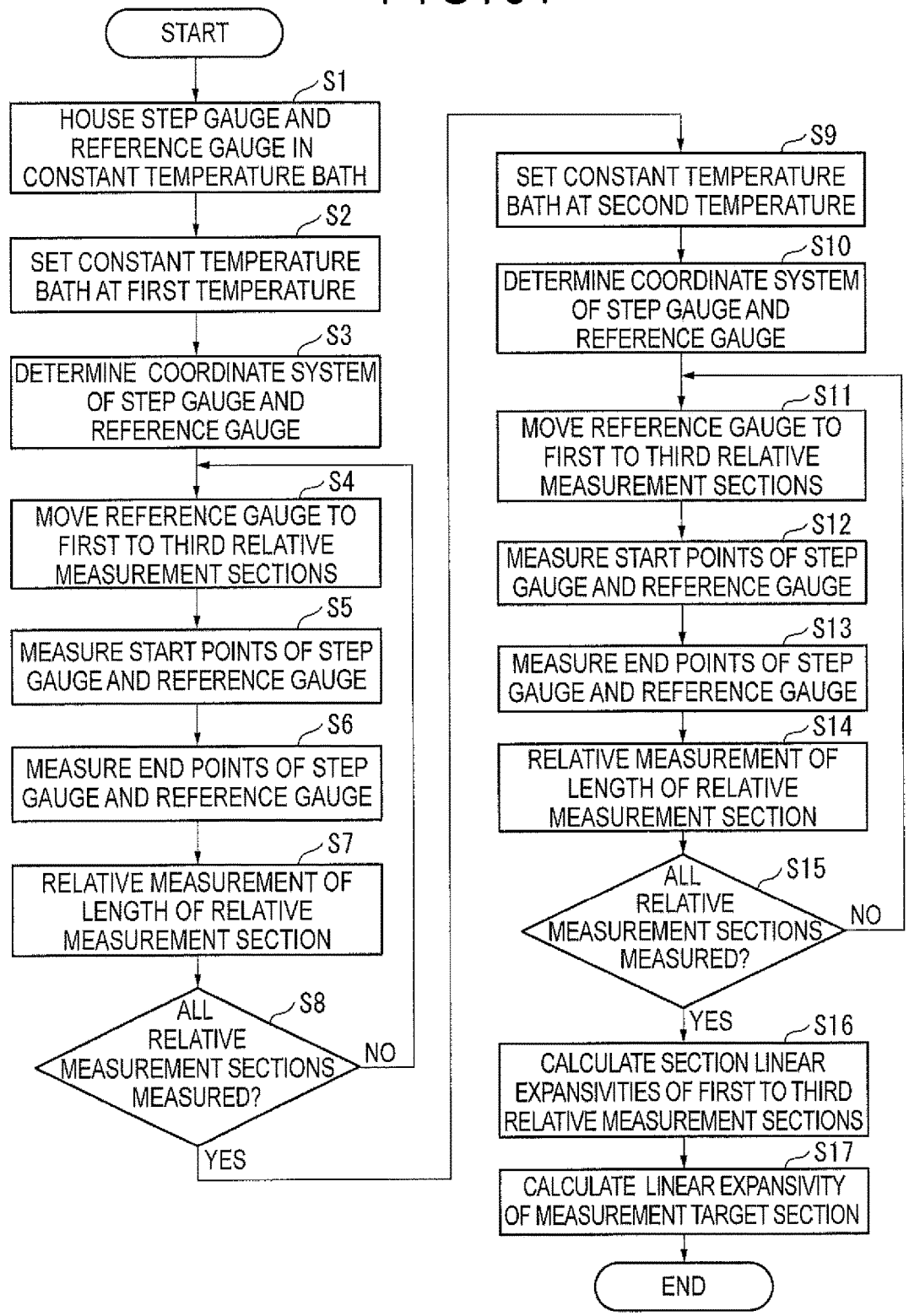
FIG. 37 is a flow chart showing a measurement process in the eleventh exemplary embodiment.

FIG. 37 shows a measurement process of the CTE of the step gauge 10 using the CTE measuring device 1.

At the start of the measurement, the temperature-controlled chamber 30 is fixed on the coordinate measuring machine 40 to provide the CTE measuring device 1 and the step gauge 10 and the reference gauge block 20E are placed inside the temperature-controlled chamber 30 (Step S1).

Then, all of the measurement apertures 31 are closed to set the temperature inside the temperature-controlled chamber 30 at the first temperature t1 and the temperature-controlled chamber 30 is left for a predetermined time to stabilize the temperature (Step S2).

When the internal temperature of the temperature-controlled chamber 30 is stabilized at the first temperature t1, the coordinate systems of the step gauge 10 and the reference gauge block 20E are determined (Step S3).

Specifically, one of the measurement apertures 31 of the temperature-controlled chamber 30 is opened to introduce the measurement probe 46 of the coordinate measuring machine 40 and coordinates of a plurality of points on the end faces, upper faces and lateral faces of the step gauge 10 and the reference gauge block 20E are detected, thereby acquiring the orientations of the drawing directions Lt, Lr and the coordinate systems (i.e. a standard of the position measurement) of the step gauge 10 and the reference gauge block 20E.

When the coordinate systems of the step gauge 10 and the reference gauge block 20 are determined (Step S3), relative measurement of the dimensions of the step gauge 10 and the reference gauge block 20E is performed for each of the relative measurement sections M1 to M3 (Steps S4 to S8).

Initially, the movable base 76 of the reference gauge drive mechanism 70 is moved to place the reference gauge block 20E at the first relative measurement section M1 (Step S4).

Then, a first one of the measurement apertures 31 nearest to the start point (position P0) of the first relative measurement section M1 is opened, and the measurement probe 46 of the coordinate measuring machine 40 is introduced through the first one of the measurement apertures 31 to measure the positions of portions (the first surface 11 and the first reference surface 2A in this instance) of each of the step gauge 10 and the reference gauge block 20E corresponding to the start point of the first relative measurement section M1 (Step S5).

Subsequently, a second one of the measurement apertures 31 nearest to the end point (position P4) of the first relative measurement section M1 is opened, and the measurement probe 46 of the coordinate measuring machine 40 is introduced through the second one of the measurement apertures 31 to measure the positions of portions (the first reference surface 2A of the reference gauge block 20E and corresponding one of the protrusions 19 of the step gauge 10) of each of the step gauge 10 and the reference gauge block 20E corresponding to the end point of the first relative measurement section M1 (Step S6).

Through the above steps, the start point and the end point of the step gauge 10 and the reference gauge block 20E in the first relative measurement section M1 are measured. Then, a length Dt11 of the first relative measurement section M1 of the step gauge 10 at the first temperature t1 is measured through the relative measurement with reference to the reference gauge block 20E (Step S7).

When the relative measurement of the first relative measurement section M1 is finished, whether or not a predetermined number of measurement(s) is done checked (Step S8) and the same Steps S4 to S8 are repeated for the second relative measurement section M2 and the third relative measurement section M3.

Then, when the lengths Dt11 to Dt31 of all of the relative measurement sections M1 to M3 of the step gauge 10 at the first temperature t1 are measured, the measurement at the first temperature t1 is finished and the measurement at the second temperature is started.

Specifically, all of the measurement apertures 31 are closed to set the temperature inside the temperature-controlled chamber 30 at the second temperature t2 and the temperature-controlled chamber 30 is left for a predetermined time to stabilize the temperature (Step S9).

When the internal temperature of the temperature-controlled chamber 30 is stabilized at the second temperature t2, the coordinate systems of the step gauge 10 and the reference gauge block 20E are determined (Step S10). It should be noted that Step S10 is the same as the above-described Step S3.

Subsequently, the relative measurement of the dimensions of the step gauge 10 and the reference gauge block 20E are performed for the first to third relative measurement sections M1 to M3 (Steps S11 to S15). It should be noted that Steps S11 to 15 are the same as the above-described Steps S4 to S8.

When the lengths Dt12 to Dt32 of all of the relative measurement sections M1 to M3 of the step gauge 10 at the second temperature t2 are measured through the above steps, the measurement at the second temperature t2 is finished.

When the lengths Dt11 to Dt31 of the first to third relative measurement sections M1 to M3 of the step gauge 10 at the first temperature t1 and the lengths Dt12 to Dt32 of the relative measurement sections M1 to M3 of the step gauge 10 at the second temperature t2 are measured through the above process, the section CTEs $\alpha_1$ to $\alpha_3$ of the relative measurement sections are calculated (Step S16).

$$\alpha_1 = [(Dt11 - Dt12)/Dt11]/(t1 - t2)$$

$$\alpha_2 = [(Dt21 - Dt22)/Dt21]/(t1 - t2)$$

$$\alpha_2 = [(Dt31 - Dt32)/Dt31]/(t1 - t2)$$

When the section CTEs $\alpha_1$ to $\alpha_3$ of the relative measurement sections M1 to M3 are calculated, the CTE $\alpha$ of the measurement target section is calculated (Step S17).

The above-described first to sixth count sections C1 to C6 are used for the calculation of the CTE $\alpha$ of the measurement target section. Specifically, the CTE $\alpha$ of the entire measurement target section is calculated by: calculating the average $\alpha_n$ of the section CTEs $\alpha_1$ to $\alpha_3$ of the relative measurement sections M1 to M3 overlapping at each of the count sections C1 to C6 for every length Dd; multiplying the average $\alpha_n$ of the section CTEs of the relative measurement sections by the weight coefficient c=⅙ of the respective count section; and totalizing the products c·$\alpha_n$ of all of the count sections.

Advantages of Eleventh Exemplary Embodiment

In the eleventh exemplary embodiment, the CTE $\alpha$ of the entire step gauge 10 can be calculated by: defining the plurality of relative measurement section M1 to M3 configured to cover the entirety of the measurement target section of the step gauge 10; performing the relative measurement of the lengths Dt11 to Dt31 and Dt12 to Dt32 of the step gauge 10 in the relative measurement sections; and calculating the section CTEs $\alpha_1$ to $\alpha_3$ of the relative measurement sections based on the difference in lengths of the relative measurement sections at the first temperature t1 and the second temperature t2.

Accordingly, even when the length of the measurement target section Dt of the step gauge 10 is longer than the length Dr of the reference gauge block 20E, the relative measurement using the reference gauge block 20E is possible in each of the relative measurement sections M1 to M3 in the eleventh exemplary embodiment.

During the relative measurement of the length of the step gauge 10 in each of the relative measurement sections M1 to M3, the relative measurement with respect to the length Dr of the reference gauge block 20E is performed using the coordinate measuring machine 40, so that a highly accurate measurement can be inexpensively performed without using an expensive optical interferometer.

In the eleventh exemplary embodiment, the relative measurement of the length of the step gauge 10 is performed with respect to the reference gauge block 20E using the coordinate measuring machine 40. Accordingly, the results of the length measurement are not dependent on the accuracy of the scale of the coordinate measuring machine 40 but solely dependent on the accuracy of the reference gauge block 20E. Even when the length of the measurement target section of the step gauge 10 is increased, the length of each of the relative measurement sections M1 to M3 can be set shorter than the length of the measurement target section of the step gauge 10, so that an existing reference gauge block 20E can be used as the reference gauge and the production cost can be reduced.

Further, since both of the reference gauge block 20E (reference gauge) and the step gauge 10 (measurement target) are housed in the temperature-controlled chamber 30 in the eleventh exemplary embodiment, it is only necessary to open/close the measurement apertures 31 of the temperature-controlled chamber 30 to introduce/take out the measurement probe 46 in performing the relative measurement of the length of the relative measurement sections using the coordinate measuring machine 40.

In addition, since the reference gauge block 20E corresponding to the relative measurement sections M1 to M3 is prepared in advance, it is not necessary to introduce/take out the reference gauge block 20E into/out of the temperature-controlled chamber 30 during the measurement process, so that the temperature change in the temperature-controlled chamber 30 and the measurement process time can be minimized during the measurement process.

As described above, the CTE of an entirety of a dimension reference gauge (step gauge 10) having a length exceeding the length of the reference gauge (reference gauge block 20E) can be highly accurately and inexpensively measured in the eleventh exemplary embodiment.

In the eleventh exemplary embodiment, since the allocated number n (=3) of the relative measurement sections M1 to M3 of the length Dr are defined and are arranged with the shift amount Dd, the entirety of the measurement target section having the length Dt can be covered.

The average of the CTEs $\alpha 1$ to $\alpha 3$ of the sections at which the relative measurement sections M1 to M3 are mutually overlapped can be calculated, so that the CTE $\alpha$ of the entirety of the measurement target section can be highly accurately and reliably calculated.

Especially, the highly accurate CTE $\alpha$ can be efficiently measured in the eleventh exemplary embodiment by: allocating the plurality of count sections C1 to C6 to the measurement target section; averaging the section CTEs $\alpha 1$ to $\alpha 3$ in each of the count sections; and totalizing the averages after applying the weight coefficient c of the count sections C1 to C6.

In the eleventh exemplary embodiment, the reference gauge drive mechanism 70 is placed in the temperature-controlled chamber 30 and the reference gauge block 20E is movably arranged to the plurality of relative measurement sections M1 to M3 by the movable base 76, so that the reference gauge block 20E can be sequentially moved to the plurality of relative measurement sections M1 to M3.

Accordingly, the single reference gauge block 20E can be used in common to the plurality of relative measurement sections M1 to M3, so that fluctuation in the measurement accuracy can be prevented.

In the eleventh exemplary embodiment, since the reference gauge block 20E is made of a material of extremely low expansion coefficient or a material of zero expansion coefficient, it is not necessary to perform temperature correction for the length of the reference gauge block 20E between the first temperature t1 and the second temperature t2.

It should be noted that, when the reference gauge block 20E is made of a material having a known expansion coefficient, a highly accurate relative measurement can be performed by calculating highly accurate length of the reference gauge at the first temperature t1 and the second temperature t2 through a temperature correction.

Different Setting Examples for Relative Measurement Section

The three relative measurement sections M1 to M3 are defined in the above-described eleventh exemplary embodiment.

Figure 38:
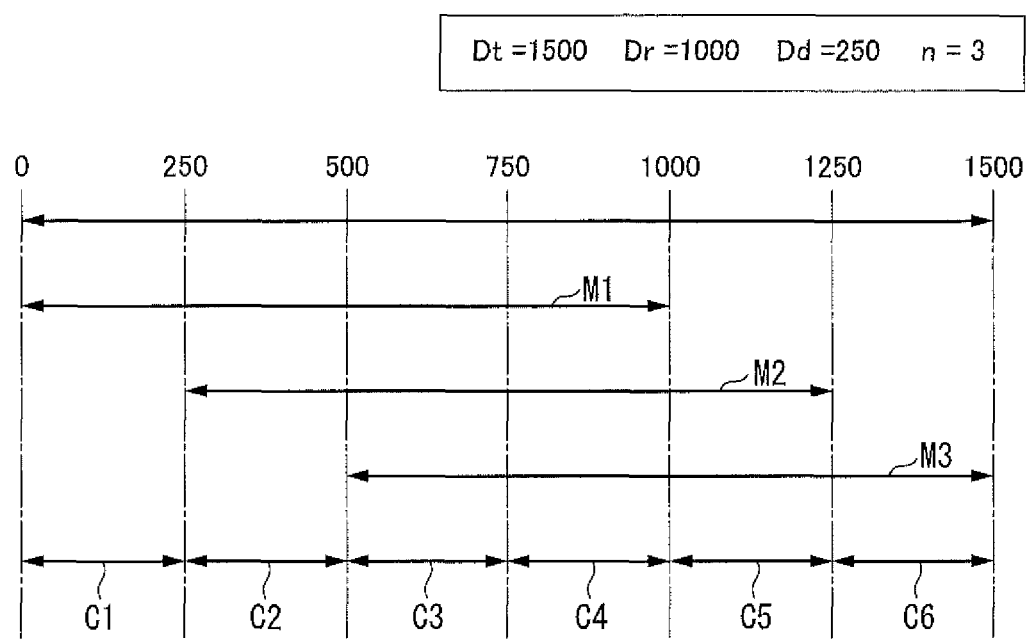
FIG. 38 is a schematic illustration of a section setting in the eleventh exemplary embodiment.

As shown in FIG. 38, the reference gauge block 20E with the reference gauge length Dr=1000 mm is used for the measurement target section (length Dt=1500 mm) of the step gauge 10 and the shift amount Dd is defined to be 250 mm (Dd=250 mm) in the eleventh exemplary embodiment.

The reference gauge length Dr (=1000 mm) is in an integer ratio ("2:3") to the length Dt (=1500 mm) of the measurement target section.

The shift amount Dd (=250 mm) is a half (i.e. one divided by an integer) of the difference (=500 mm) between the reference gauge length Dr and the length Dt of the measurement target section.

The allocated number n for the relative measurement section to be allocated to the measurement target section is defined to be 3 (allocated number n=3), which is larger by one than the number (2) obtained by dividing the difference between the length Dt of the measurement target section and the reference gauge length Dr (500 mm) by the shift amount Dd (=250 mm).

The count section includes six count sections C1 to C6 based on the length Dt (=1500 mm) of the measurement target section and the shift amount Dd (=250 mm) (i.e. Dt/Dd=6).

In contrast, the following different settings are possible.

Figure 39:
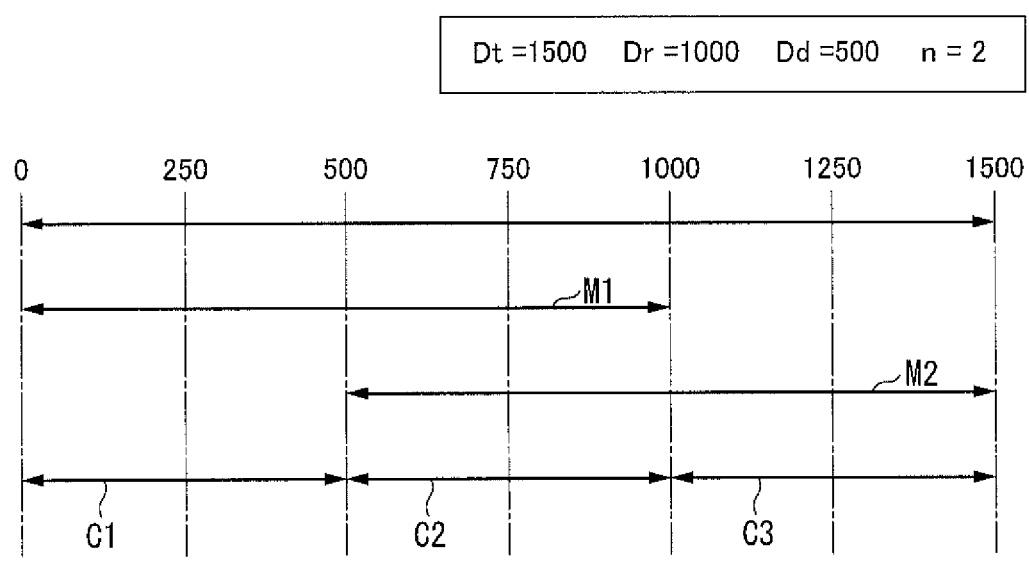
FIG. 39 is a schematic illustration of another section setting in the eleventh exemplary embodiment.

As shown in FIG. 39, while the reference gauge block 20E with the reference gauge length Dr=1000 mm is used for the measurement target section (length Dt=1500 mm) of the step gauge 10, the shift amount Dd may alternatively be defined to be 500 mm (Dd=500 mm).

The reference gauge length Dr (=1000 mm) is in an integer ratio ("2:3") to the length Dt (=1500 mm) of the measurement target section.

The shift amount Dd (=500 mm) is 1/1 (i.e. one divided by an integer) of the difference (=500 mm) between the reference gauge length Dr and the length Dt of the measurement target section.

The allocated number n may be defined to be 2 (allocated number n=2), which is larger by one than the number (1) obtained by dividing the difference between the length Dt of the measurement target section and the reference gauge length Dr (500 mm) by the shift amount Dd (=500 mm).

The count section may include three (Dt/Dd=3) count sections C1 to C3.

Figure 40:
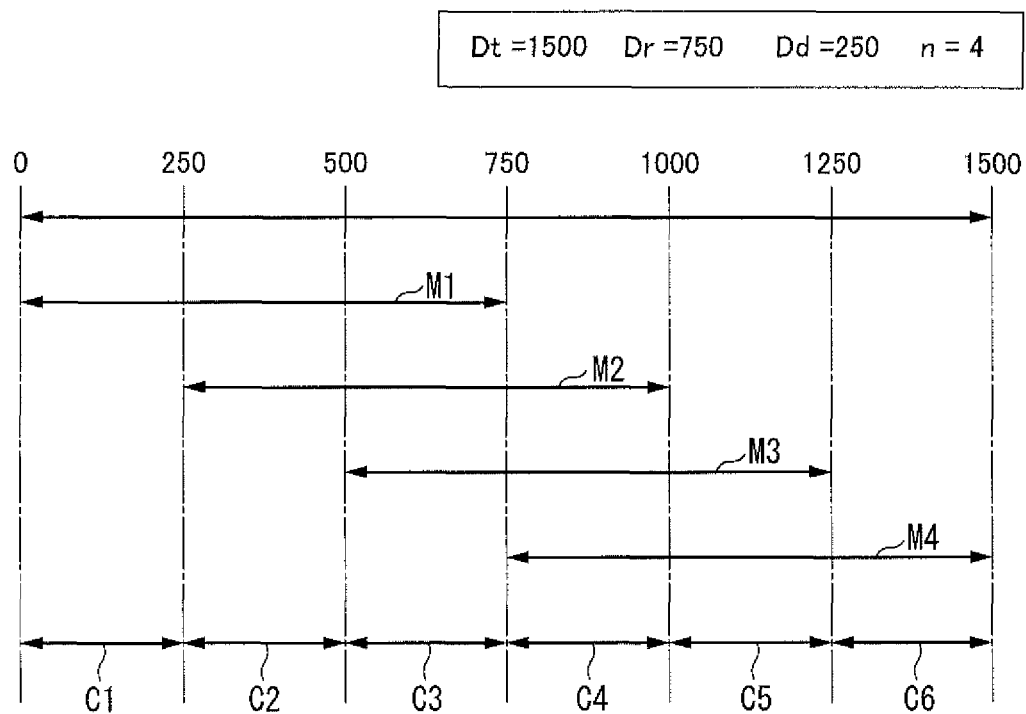
FIG. 40 is a schematic illustration of still another section setting in the eleventh exemplary embodiment.

As shown in FIG. 40, the reference gauge block 20E with the reference gauge length Dr=750 mm may alternatively be used for the measurement target section (length Dt=1500 mm) of the step gauge 10, while the shift amount Dd is defined to be 250 mm (Dd=250 mm).

The reference gauge length Dr (=750 mm) is in an integer ratio ("1:2") to the length Dt (=1500 mm) of the measurement target section.

The shift amount Dd (=250 mm) is one third (i.e. one divided by an integer) of the difference (=750 mm) between the reference gauge length Dr and the length Dt of the measurement target section.

The allocated number n may be defined to be 4 (allocated number n=4), which is larger by one than the number (3) obtained by dividing the difference between the length Dt of the measurement target section and the reference gauge length Dr (750 mm) by the shift amount Dd (=250 mm).

The count section may include six (Dt/Dd=6) count sections C1 to C6.

Figure 41:
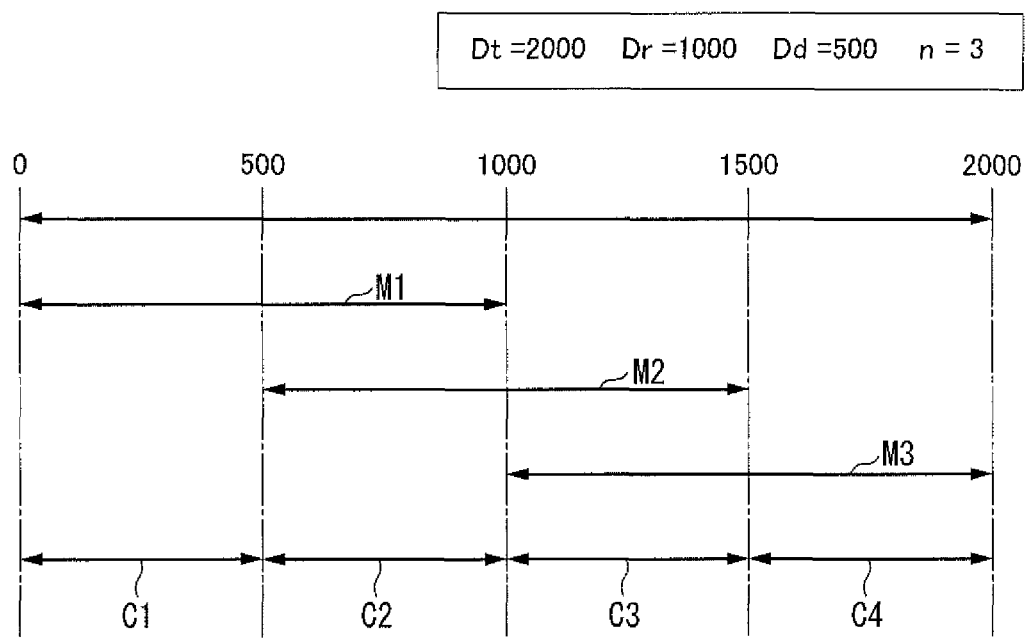
FIG. 41 is a schematic illustration of a further section setting in the eleventh exemplary embodiment.

As shown in FIG. 41, the reference gauge block 20E with the reference gauge length Dr=1000 mm may alternatively be used for the measurement target section (length Dt=2000 mm) of the step gauge 10 and the shift amount Dd may alternatively be defined to be 500 mm (Dd=500 mm).

The reference gauge length Dr (=1000 mm) is in an integer ratio ("1:2") to the length Dt (=2000 mm) of the measurement target section.

The shift amount Dd (=500 mm) is ½ (i.e. one divided by an integer) of the difference (=1000 mm) between the reference gauge length Dr and the length Dt of the measurement target section.

The allocated number n may be defined to be 3 (allocated number n=3), which is larger by one than the number (2) obtained by dividing the difference (1000 mm) between the length Dt of the measurement target section and the reference gauge length Dr by the shift amount Dd (=500 mm).

The count section may include four (Dt/Dd=4) count sections C1 to C4.

Figure 42:
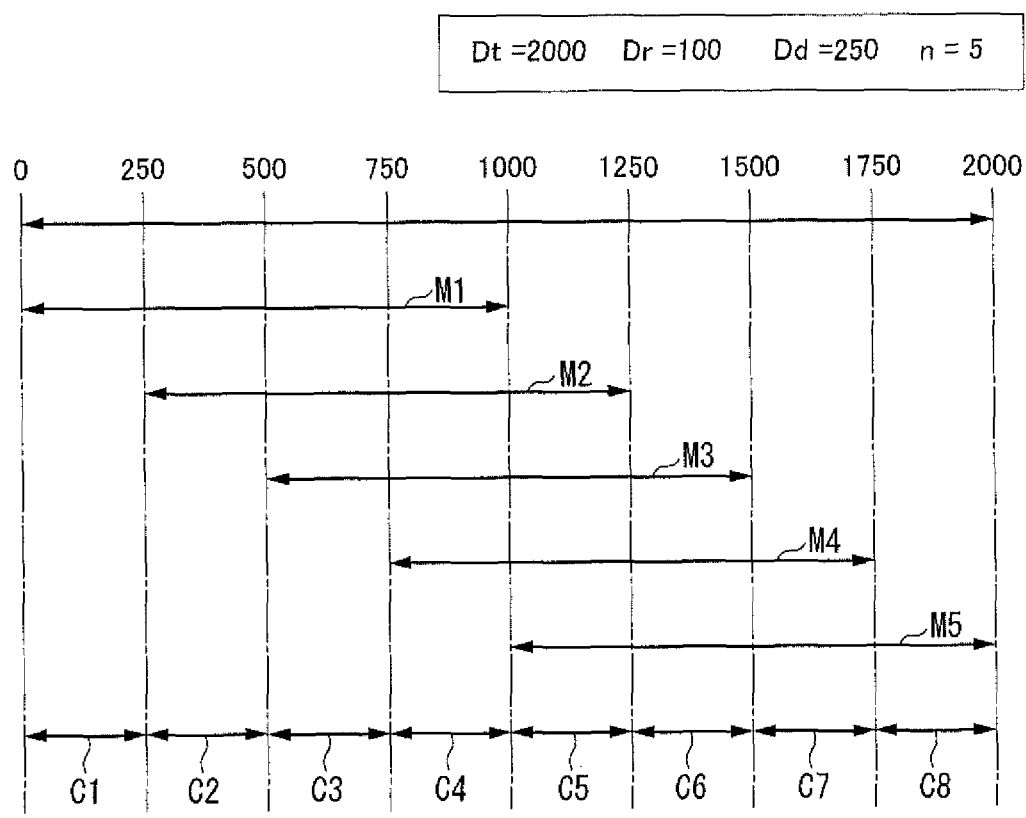
FIG. 42 is a schematic illustration of a still further section setting in the eleventh exemplary embodiment.

As shown in FIG. 42, the reference gauge block 20E with the reference gauge length Dr=1000 mm may alternatively be used for the measurement target section (length Dt=2000 mm) of the step gauge 10 and the shift amount Dd may alternatively be defined to be 250 mm (Dd=250 mm).

The reference gauge length Dr (=1000 mm) is in an integer ratio ("1:2") to the length Dt (=2000 mm) of the measurement target section.

The shift amount Dd (=250 mm) is one fourth (i.e. one divided by an integer) of the difference (=1000 mm) between the reference gauge length Dr and the length Dt of the measurement target section.

The allocated number n may be defined to be 5 (allocated number n=5), which is larger by one than the number (4) obtained by dividing the difference (1000 mm) between the length Dt of the measurement target section and the reference gauge length Dr by the shift amount Dd (=250 mm).

The count section may include eight (Dt/Dd=8) count sections C1 to C8.

Figure 43:
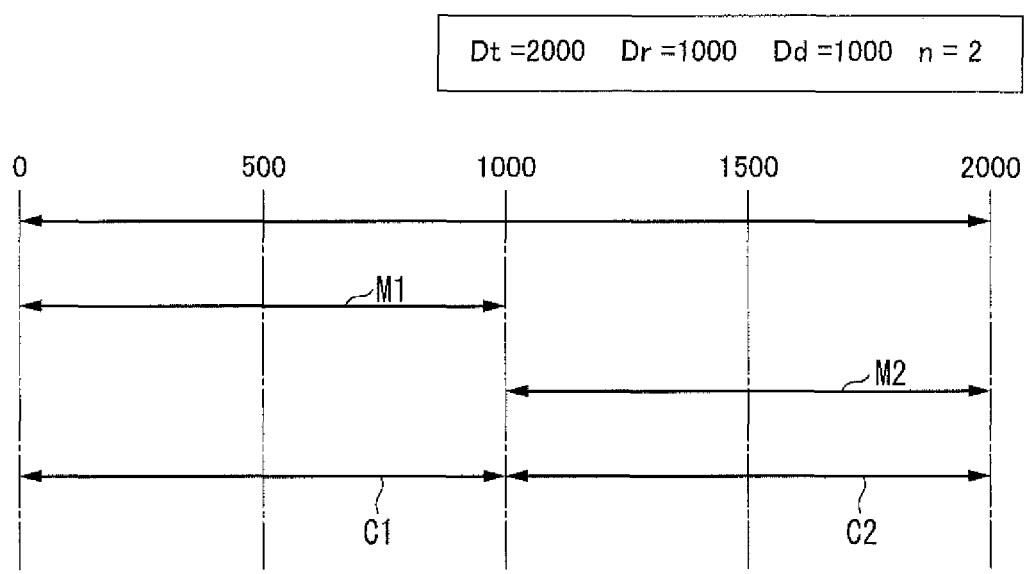
FIG. 43 is a schematic illustration of a still further section setting in the eleventh exemplary embodiment.

As shown in FIG. 43, the reference gauge block 20E with the reference gauge length Dr=1000 mm may alternatively be used for the measurement target section (length Dt=1000 mm) of the step gauge 10 and the shift amount Dd may alternatively be defined to be 1000 mm (Dd=1000 mm).

The reference gauge length Dr (=1000 mm) is in an integer ratio ("1:2") to the length Dt (=2000 mm) of the measurement target section.

The shift amount Dd (=1000 mm) is 1/1 (i.e. one divided by an integer) of the difference (=500 mm) between the reference gauge length Dr and the length Dt of the measurement target section.

The allocated number n may be defined to be 2 (allocated number n=2), which is larger by one than the number (1) obtained by dividing the difference (1000 mm) between the length Dt of the measurement target section and the reference gauge length Dr by the shift amount Dd (=1000 mm).

The count section may include two (Dt/Dd=2) count sections C1 to C2.

It should be noted that the relative measurement sections M1, M2 in the setting example shown in FIG. 43 are simply arranged with no overlapping therebetween. The count sections C1, C2 are the same as the relative measurement sections M1, M2. Since the relative measurement sections M1, M2 are not overlapped in the count sections C1, C2, calculation of average of the count sections and the weight-accompanying totalizing calculation can be omitted.

Figure 44:
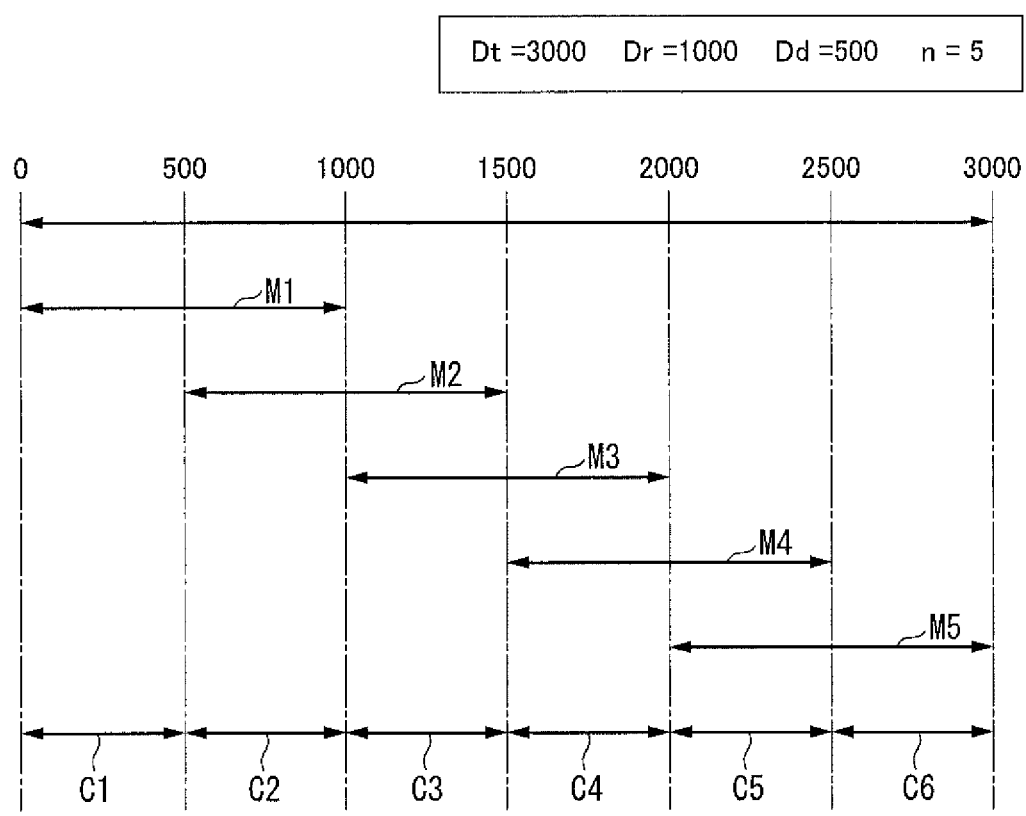
FIG. 44 is a schematic illustration of a still further section setting in the eleventh exemplary embodiment.

As shown in FIG. 44, the reference gauge block 20E with the reference gauge length Dr=1000 mm may be used for the measurement target section (length Dt=3000 mm) of the step gauge 10 and the shift amount Dd may alternatively be defined to be 500 mm (Dd=500 mm).

The reference gauge length Dr (=1000 mm) is in an integer ratio ("1:3") to the length Dt (=3000 mm) of the measurement target section.

The shift amount Dd (=500 mm) is ¼ (i.e. one divided by an integer) of the difference (=2000 mm) between the reference gauge length Dr and the length Dt of the measurement target section.

The allocated number n may be defined to be 5 (allocated number n=5), which is larger by one than the number (4) obtained by dividing the difference (2000 mm) between the length Dt of the measurement target section and the reference gauge length Dr by the shift amount Dd (=500 mm).

The count section may include six (Dt/Dd=6) count sections C1 to C6.

Figure 45:
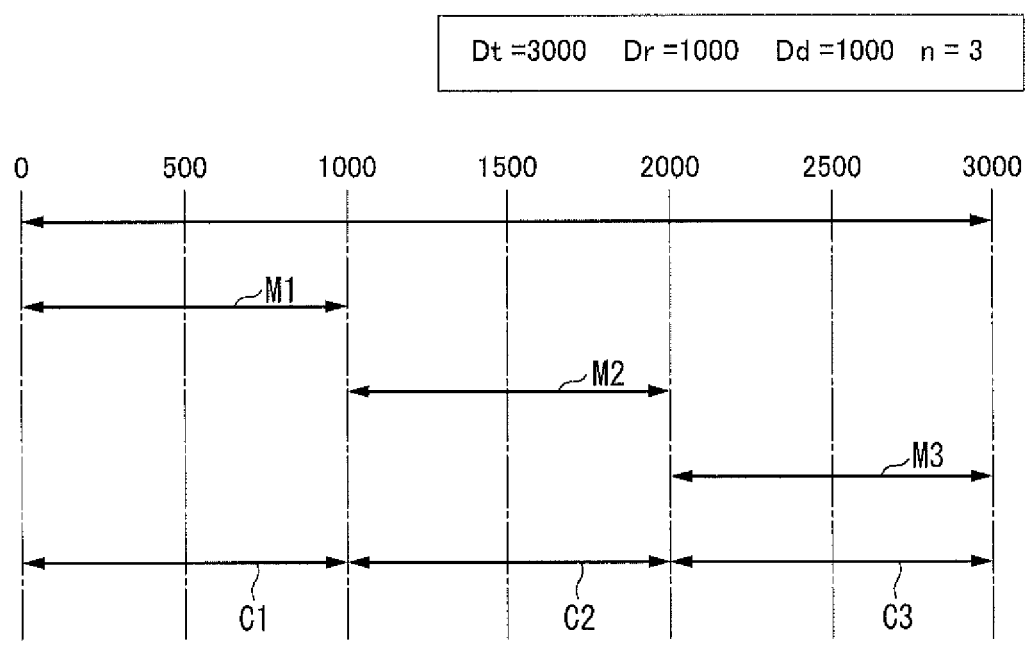
FIG. 45 is a schematic illustration of a still further section setting in the eleventh exemplary embodiment.

As shown in FIG. 45, the reference gauge block 20E with the reference gauge length Dr=1000 mm may be used for the measurement target section (length Dt=3000 mm) of the step gauge 10 and the shift amount Dd may alternatively be defined to be 1000 mm (Dd=1000 mm).

The reference gauge length Dr (=1000 mm) is in an integer ratio ("1:3") to the length Dt (=3000 mm) of the measurement target section.

The shift amount Dd (=1000 mm) is ½ (i.e. one divided by an integer) of the difference (=2000 mm) between the reference gauge length Dr and the length Dt of the measurement target section.

The allocated number n may be defined to be 3 (allocated number n=3), which is larger by one than the number (2) obtained by dividing the difference (2000 mm) between the length Dt of the measurement target section and the reference gauge length Dr by the shift amount Dd (=1000 mm).

The count section may include three (Dt/Dd=3) count sections C1 to C3.

It should be noted that the relative measurement sections M1 to M3 in the setting example shown in FIG. 45 are simply arranged with no overlapping therebetween. The count sections C1 to C3 are the same as the relative measurement sections M1 to M3. Since the relative measurement sections M1 to M3 are not overlapped in the count sections C1 to C3, calculation of average of the count sections and the weight-accompanying totalizing calculation can be omitted.

Twelfth Exemplary Embodiment

Figure 46:
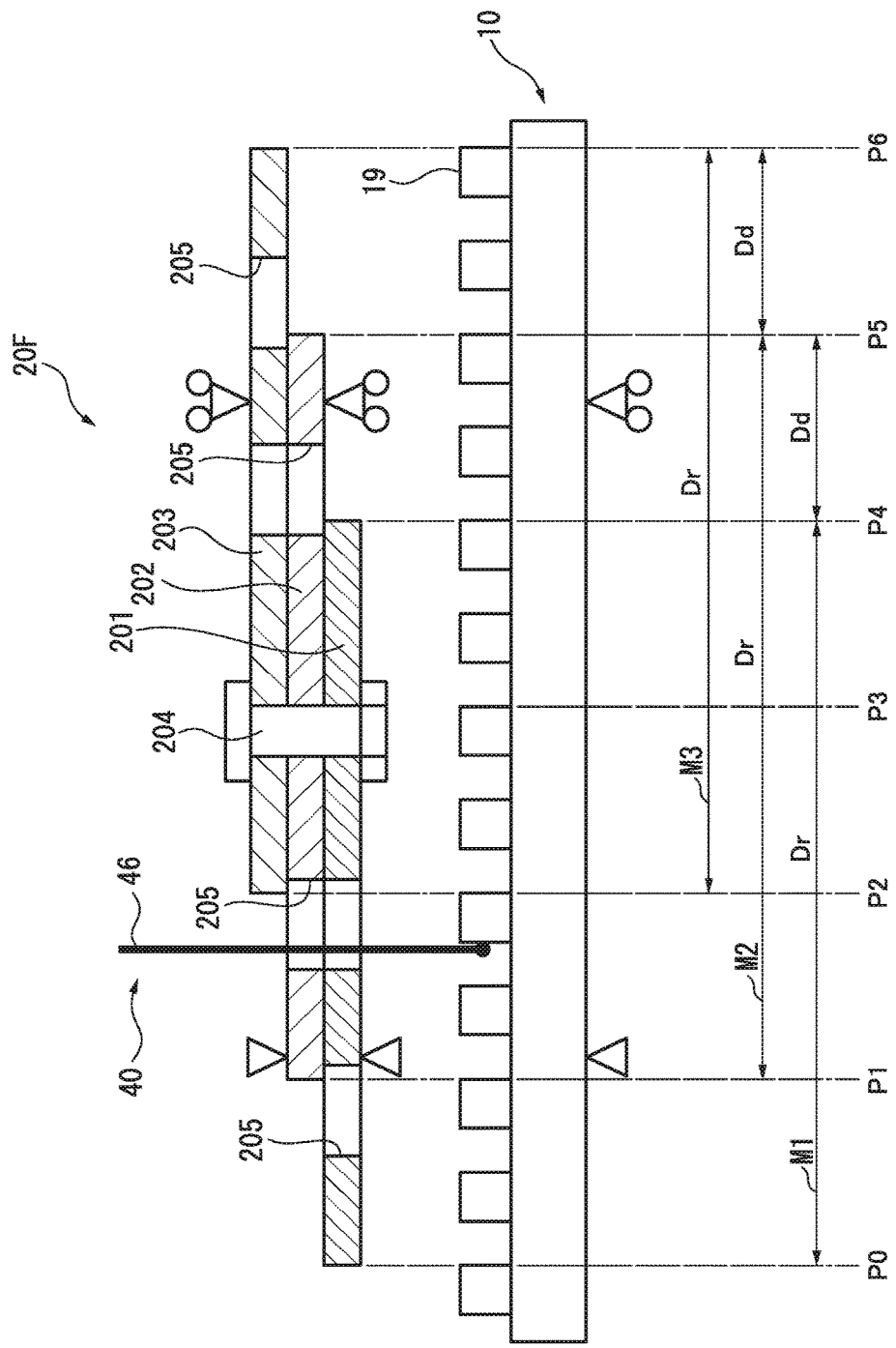
FIG. 46 is a side elevational view showing a reference gauge in a twelfth exemplary embodiment of the invention.
Figure 47:
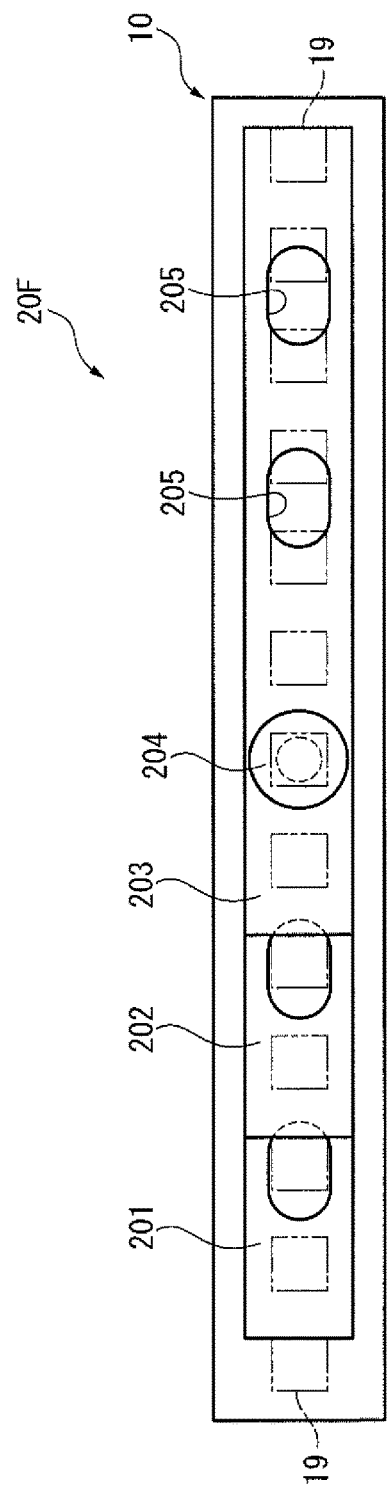
FIG. 47 is a plan view showing the reference gauge in the twelfth exemplary embodiment.
Figure 48:
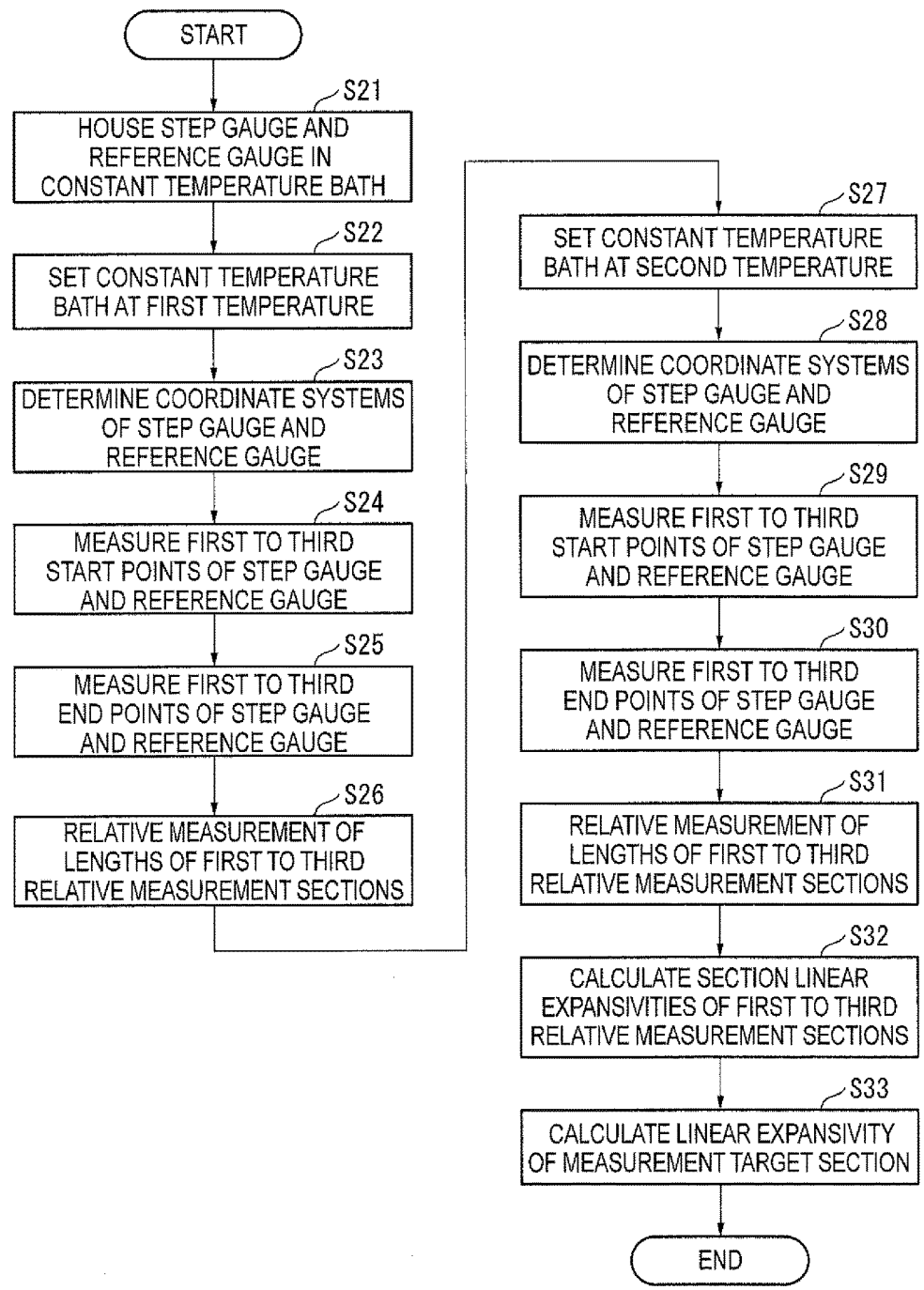
FIG. 48 is a flow chart showing a measurement process in the twelfth exemplary embodiment.

FIGS. 46 to 48 show a twelfth exemplary embodiment of the invention.

Basic components of the twelfth exemplary embodiment are the same as those of the above-described eleventh exemplary embodiment. For the convenience of explanation, duplicated description of the common components will be omitted and only differences will be described below.

In the above-described eleventh exemplary embodiment, the reference gauge in a form of the reference gauge block 20E is used, which is moved by the reference gauge drive mechanism 70 to be placed at the first to third relative measurement sections M1 to M3.

In contrast, the reference gauge used in the twelfth exemplary embodiment is a reference gauge block 20F including three pairs of end faces corresponding to the first to third relative measurement sections M1 to M3 as shown in FIGS. 46 and 47.

The reference gauge block 20F includes three gauge blocks 201, 202, 203, which are combined and fixed by a fixture 204.

The gauge blocks 201, 202, 203 are each an existing gauge block having the length Dr and are overlapped with each other with the shift amount Dd.

The gauge block 201 is the standard of the relative measurement for the first relative measurement section M1.

Similarly, the gauge blocks 202, 203 respectively are standards for the relative measurement for the second and third relative measurement sections M2, M3.

Each of the gauge blocks 201, 202, 203 includes through holes 205 at positions corresponding to end faces of the other gauge blocks.

When the measurement probe 46 of the coordinate measuring machine 40 is brought into contact with the end faces of the gauge blocks for the relative measurement of the relative measurement sections M1 to M3, the measurement probe 46 can reach through the through holes 205 the end faces of the lower gauge blocks 201, 202 covered by the upper gauge blocks 202, 203 and further to a target portion on the step gauge 10 located further below.

Measurement Process of CTE

FIG. 48 shows a measurement process of the CTE of the step gauge 10 according to the twelfth exemplary embodiment.

At the start of the measurement, the temperature-controlled chamber 30 is fixed on the coordinate measuring machine 40 to provide the CTE measuring device 1 and the step gauge 10 and the reference gauge block 20F are placed inside the temperature-controlled chamber 30 (Step S21).

Then, all of the measurement apertures 31 are closed to set the temperature inside the temperature-controlled chamber 30 at the first temperature t1 and the temperature-controlled chamber 30 is left for a predetermined time to stabilize the temperature (Step S22).

When the internal temperature of the temperature-controlled chamber 30 is stabilized at the first temperature t1, the coordinate systems of the step gauge 10 and the reference gauge block 20F are determined (Step S23).

The steps so far are the same as Steps S to S3 in the above-described eleventh exemplary embodiment.

When the coordinate systems of the step gauge 10 and the reference gauge block 20F are determined (Step S23), relative measurement of the dimensions of the step gauge 10 and the reference gauge block 20F is performed for each of the relative measurement sections M1 to M3 (Steps S24 to S26).

Initially, in Step S24, a first one of the measurement apertures 31 nearest to the start point (position P0) of the first relative measurement section M1 is opened, and the measurement probe 46 of the coordinate measuring machine 40 is introduced through the first one of the measurement apertures 31 to measure the positions of portions of each of the step gauge 10 and the reference gauge block 20F corresponding to the start point of the first relative measurement section M1. An end face of the gauge block 201 corresponds to the start point of the first relative measurement section M1 in the reference gauge block 20F.

Subsequently, a second one of the measurement apertures 31 nearest to the start point (position P1) of the second relative measurement section M2 is opened, and the measurement probe 46 of the coordinate measuring machine 40 is introduced through the second one of the measurement apertures 31 to measure the positions of portions of each of the step gauge 10 and the reference gauge block 20F corresponding to the start point of the second relative measurement section M2. An end face of the gauge block 202 corresponds to the start point of the second relative measurement section M2 in the reference gauge block 20F.

Further, a third one of the measurement apertures 31 nearest to the start point (position P2) of the third relative measurement section M3 is opened, and the measurement probe 46 of the coordinate measuring machine 40 is introduced through the third one of the measurement apertures 31 to measure the positions of portions of each of the step gauge 10 and the reference gauge block 20F corresponding to the start point of the third relative measurement section M3. An end face of the gauge block 203 corresponds to the start point of the third relative measurement section M3 in the reference gauge block 20F.

Then, in Step S25, a fourth one of the measurement apertures 31 nearest to the end point (position P4) of the first relative measurement section M1 is opened, and the measurement probe 46 of the coordinate measuring machine 40 is introduced through the fourth one of the measurement apertures 31 to measure the positions of portions of each of the step gauge 10 and the reference gauge block 20F corresponding to the end point of the first relative measurement section M1. An end face of the gauge block 201 corresponds to the end point of the first relative measurement section M3 in the reference gauge block 20F.

Subsequently, a fifth one of the measurement apertures 31 nearest to the end point (position P5) of the second relative measurement section M2 is opened, and the measurement probe 46 of the coordinate measuring machine 40 is introduced through the fifth one of the measurement apertures 31 to measure the positions of portions of each of the step gauge 10 and the reference gauge block 20F corresponding to the end point of the second relative measurement section M2. An end face of the gauge block 202 corresponds to the end point of the second relative measurement section M2 in the reference gauge block 20F.

Further, a sixth one of the measurement apertures 31 nearest to the end point (position P6) of the third relative measurement section M3 is opened, and the measurement probe 46 of the coordinate measuring machine 40 is introduced through the third one of the measurement apertures 31 to measure the positions of portions of each of the step gauge 10 and the reference gauge block 20F corresponding to the end point of the third relative measurement section M3. An end face of the gauge block 203 corresponds to the end point of the third relative measurement section M3 in the reference gauge block 20F.

Through the above steps, the start points and the end points of the step gauge 10 and the reference gauge block 20F in the first to third relative measurement sections M1 to M3 are measured. Then, the lengths Dt11 to Dt31 of the first to third relative measurement sections M1 to M3 of the step gauge 10 at the first temperature t1 are measured through the relative measurement with reference to the reference gauge block 20F (Step S26).

When the lengths Dt11 to Dt31 of the step gauge 10 at the first temperature t1 are measured, the measurement at the first temperature t1 is finished and the measurement at the second temperature is started.

Specifically, all of the measurement apertures 31 are closed to set the temperature inside the temperature-controlled chamber 30 at the second temperature t2 and the temperature-controlled chamber 30 is left for a predetermined time to stabilize the temperature (Step S27).

When the internal temperature of the temperature-controlled chamber 30 is stabilized at the second temperature t2, the coordinate systems of the step gauge 10 and the reference gauge block 20F are determined (Step S28).

When the coordinate systems of the step gauge 10 and the reference gauge block 20F are determined (Step S28), relative measurement of the dimensions of the step gauge 10 and the reference gauge block 20F is performed for each of the relative measurement sections M1 to M3 (Steps S29 to S31).

It should be noted that Steps S27 to 31 are the same as the above-described Steps S22 to S26.

When the lengths Dt12 to Dt32 of all of the relative measurement sections M1 to M3 of the step gauge 10 at the second temperature t2 are measured through the above steps, the measurement at the second temperature t2 is finished.

When the lengths Dt11 to Dt31 of the first to third relative measurement sections M1 to M3 of the step gauge 10 at the first temperature t1 and the lengths Dt12 to Dt32 of the first to third relative measurement sections M1 to M3 of the step gauge 10 at the second temperature t2 are measured through the above process, the section CTEs $\alpha 1$ to $\alpha 3$ of the relative measurement sections are calculated (Step S32).

When the section CTEs $\alpha 1$ to $\alpha 3$ of the relative measurement sections M1 to M3 are calculated, the CTE $\alpha$ of the measurement target section is calculated (Step S33).

The Steps S32 and S33 are the same as Steps S16 and S17 in the above-described eleventh exemplary embodiment.

The twelfth exemplary embodiment provides the same advantages as those mentioned in the above-described eleventh exemplary embodiment.

Further, in the twelfth exemplary embodiment, a plurality of the relative measurement sections M1 to M3 can be measured using the single reference gauge block 20F, so that a movement operation of the reference gauge block 20F and the like can be omitted.

The reference gauge block 20F of the twelfth exemplary embodiment is provided by combining the gauge blocks 201 to 203 each having the reference gauge lengths Dr corresponding to the lengths of the relative measurement sections M1 to M3 and fixing the gauge blocks 201 to 203 with the position thereof being shifted with each other by the shift amount Dd. Accordingly, the reference gauge block 20F can be easily produced and, high accuracy can be ensured equally in all of the relative measurement sections M1 to M3 using an existing gauge block as the gauge blocks 201 to 203.

Further, the through holes 205 penetrating through the top and bottom sides at middle portions of the gauge blocks 201 to 203 are provided so that an end of the other gauge block(s) is visible through the through holes 205 in the reference gauge block 20F of the twelfth exemplary embodiment. Accordingly, even when the relative measurement section of the measurement target lies at a position hidden behind the reference gauge block 20F, the measurement probe 46 of the coordinate measuring machine 40 can be introduced through one of the through holes 205.

MODIFICATION(S)

It should be understood that the scope of the invention is not limited to the above-described exemplary embodiments but includes modifications and the like as long as the modifications and the like are compatible with an object of the invention.

For instance, the first reference gauge support bases 61, 61A and the second reference gauge support bases 62, 62A in the first to fifth exemplary embodiments include the preloading unit 609 that is configured to reliably keep the contact between the lower sides of the reference gauges and the contact portions 601, 602, 603.

The preloading unit 609 is not restricted to a mechanical device using the compression coil springs 617, 627 but may alternatively be a non-contact biasing device using fluid pressure, flow of fluid, electromagnetic force and the like.

Further, when the reference gauge block 2 has a sufficient weight, the preloading unit 609 may be omitted.

The length Dx from the first surface 11 to the second surface 12 is measured as the length of the step gauge 10 in the above-described first exemplary embodiment. The length of the step gauge 10 and the CTE between the first surface 11 and the second surface 12 can be measured when the end faces of the step gauge 10 are defined as the first surface 11 and the second surface 12. Alternatively, as illustrated in FIG. 10, the first surface 11 and the second surface 12 may be defined at an end face of one of the protrusions 19 at a middle portion of the step gauge 10, so that the length and the CTE of the middle portion can be measured.

Though the measurement target in the above-described first to fifth exemplary embodiments is the step gauge 10, the measurement target may alternatively be a gauge block or other dimension reference gauge.

Further, the reference gauge is not necessarily the reference gauge block 2 but may alternatively be a dedicated reference gauge or a step gauge 10 similar to the measurement target but in a form of a highly accurately calibrated master gauge.

The above reference gauge is preferably made of a material of extremely low expansion coefficient or a material of zero expansion coefficient whose expansion due to the temperature change between the first temperature t1 and the second temperature t2 is below a detectable limit, or made of a material whose expansion coefficient is known.

Though the second reference surface 2B of the reference gauge block 2 (reference gauge) and the second surface 12 of the step gauge 10 (measurement target) are coplanarly arranged in the above-described first to fifth exemplary embodiments, the first reference surface 2A and the first surface 11 may alternatively be coplanarly arranged or the ends of the reference gauge and the measurement target may be shifted with each other in a plan view.

However, the coplanar arrangement of one of the ends of the reference gauge and the measurement target maximizes the difference in the lengths of the reference gauge and the measurement target at the end opposite the coplanarly arranged end, thereby maximizing the margin for the surface detection using the probe of the coordinate measuring machine.

Three pairs of the measurement sections and the reference sections are defined and the CTEs $\alpha 11$ to $\alpha 13$ of the sections are measured in the above-described sixth to tenth exemplary embodiments. Specifically, the first to third measurement sections S11 to S13, the measurement start points 11S to 13S and the measurement end points 11E to 13E are defined on the step gauge 10 (measurement target) and the first to third reference sections S21 to S23, the reference start points 21S to 23S and the reference end points 21E to 23E are defined on the reference gauge block 20.

However, it is not necessary that three sets of the measurement and reference sections are defined, but two sets or four or more sets of the measurement and reference sections may be defined. In addition, it is not necessary that these sections are entirely or partially overlapped but these sections may be a plurality of sections arranged along the drawing direction Lt without being overlapped.

Further, though the measurement target in the above-described sixth to tenth exemplary embodiments is the step gauge 10, the measurement target is not necessarily the step gauge 10 but may be provided by other dimension reference gauge that defines a plurality of length standards along the drawing direction Lt.

Though the measurement target in the above-described eleventh and twelfth exemplary embodiments is the step gauge 10, the measurement target is not necessarily the step gauge 10 but may be provided by other dimension reference gauge that defines a plurality of length standards along the drawing direction Lt.

Further, the reference gauge is not necessarily the reference gauge block 20E or 20F but may alternatively be a dedicated reference gauge or a step gauge 10 similar to the measurement target in a form of a highly accurately calibrated master gauge.

What is claimed is:

1. A coefficient-of-thermal-expansion measuring device of a measurement target in a form of a dimension reference gauge, the coefficient-of-thermal-expansion being measured for a section from a first surface to a second surface of the measurement target that are distanced in a drawing direction of the measurement target, the coefficient-of-thermal-expansion measuring device comprising:
    a reference gauge comprising a first reference surface and a second reference surface each corresponding to the first surface and the second surface, a length from the first reference surface to the second reference surface being known;
    a temperature-controlled chamber configured to adjust an interior temperature thereof and to house the measurement target and the reference gauge, the temperature-controlled chamber comprising a measurement surface provided with a measurement aperture;
    a measurement target support base placed in an inside of the temperature-controlled chamber and configured to support the measurement target;
    a reference gauge support base placed in the inside of the temperature-controlled chamber and configured to support the reference gauge; and
    a coordinate measuring machine comprising a measurement probe that is introducible into the inside of the temperature-controlled chamber through the measurement aperture.

2. A coefficient-of-thermal-expansion measuring device of a measurement target in a form of a dimension reference gauge, the coefficient-of-thermal-expansion of the measurement target being measured for a plurality of measurement sections defined by a plurality of pairs of a measurement start point and a measurement end point of the measurement target that are distanced in a drawing direction of the measurement target, the coefficient-of-thermal-expansion measuring device comprising:
    a reference gauge comprising a plurality of pairs of reference start points and reference end points that define a plurality of reference sections corresponding to the plurality of measurement sections, a length of each of the reference sections being known;
    a temperature-controlled chamber configured to adjust an interior temperature thereof and to house the measurement target and the reference gauge, the temperature-controlled chamber comprising a measurement surface provided with a measurement aperture; and
    a coordinate measuring machine comprising a measurement probe that is introducible into an inside of the temperature-controlled chamber through the measurement aperture.

3. The coefficient-of-thermal-expansion measuring device according to claim 1, wherein
    the reference gauge support base is configured to support the reference gauge between the measurement target and the measurement aperture.

4. The coefficient-of-thermal-expansion measuring device according to claim 3, wherein a length of the reference gauge in the drawing direction is shorter than a length of the measurement target in the drawing direction by a predetermined dimension.

5. The coefficient-of-thermal-expansion measuring device according to claim 4, wherein
    when the first and second relative measurements are performed, the first reference surface and the first surface are coplanarly arranged or the second reference surface and the second surface are coplanarly arranged.

6. The coefficient-of-thermal-expansion measuring device according to claim 1, wherein
    the measurement target support base comprises a first measurement target support base and a second measurement target support base,
    the first measurement target support base and the second measurement target support base are configured to restrict a displacement of the measurement target in two directions intersecting the drawing direction and to permit a rotation of the measurement target around axes in the two directions intersecting the drawing direction,
    one of the first measurement target support base and the second measurement target support base is configured to restrict a displacement of the measurement target in the drawing direction and the other of the first measurement target support base and the second measurement target support base is configured to permit the displacement of the measurement target in the drawing direction,
    one of the first measurement target support base and the second measurement target support base is configured to restrict a rotation of the measurement target around an axis in the drawing direction and the other one of the first measurement target support base and the second measurement target support base is configured to permit the rotation of the measurement target around the axis in the drawing direction,
    the reference gauge support base comprises a first reference gauge support base and a second reference gauge support base,
    the first reference gauge support base and the second reference gauge support base are configured to restrict a displacement of the reference gauge in the two directions intersecting the drawing direction and to permit a rotation of the reference gauge around axes in the two directions intersecting the drawing direction,
    one of the first reference gauge support base and the second reference gauge support base is configured to restrict a displacement of the reference gauge in the drawing direction and the other of the first reference gauge support base and the second reference gauge support base is configured to permit the displacement of the reference gauge in the drawing direction, and
    one of the first reference gauge support base and the second reference gauge support base is configured to restrict a rotation of the reference gauge around an axis in the drawing direction and the other of the first reference gauge support base and the second reference gauge support base is configured to permit a rotation of the reference gauge around an axis in the drawing direction.

7. The coefficient-of-thermal-expansion measuring device according to claim 6, wherein
    the first measurement target support base comprises one or two of a conical-hole-sphere contact portion, a plane-sphere contact portion and a V-shaped-groove-sphere contact portion in contact with a bottom face of the measurement target, and the second measurement target support base comprises at least one of the conical-hole-sphere contact portion, the plane-sphere contact portion and the V-shaped-groove-sphere contact portion in contact with the bottom face of the measurement target that is not provided to the first measurement target support base.

8. The coefficient-of-thermal-expansion measuring device according to claim 6, wherein
the first measurement target support base comprises one of a conical-hole-sphere contact portion and a plane-sphere contact portion in contact with a bottom face of the measurement target, and
the second measurement target support base comprises the other one of the conical-hole-sphere contact portion and the plane-sphere contact portion in contact with the bottom face of the measurement target, and
one of the first measurement target support base and the second measurement target support base comprises a sphere contact portion in contact with one of lateral faces of the measurement target and a pressing unit that is configured to press the one of lateral faces of the measurement target against the sphere contact portion.

9. The coefficient-of-thermal-expansion measuring device according to claim 6, wherein
the first reference gauge support base comprises one or two of a conical-hole-sphere contact portion, a plane-sphere contact portion and a V-shaped-groove-sphere contact portion in contact with a bottom face of the reference gauge, and
the second reference gauge support base comprises at least one of the conical-hole-sphere contact portion, the plane-sphere contact portion and the V-shaped-groove-sphere contact portion in contact with the bottom face of the reference gauge that is not provided to the first reference gauge support base.

10. The coefficient-of-thermal-expansion measuring device according to claim 6, wherein
the first reference gauge support base comprises one of a conical-hole-sphere contact portion and a plane-sphere contact portion in contact with a bottom face of the reference gauge,
the second reference gauge support base comprises the other one of the conical-hole-sphere contact portion and the plane-sphere contact portion in contact with the bottom face of the reference gauge, and
one of the first reference gauge support base and the second reference gauge support base comprises a sphere contact portion in contact with one of lateral faces of the reference gauge and a pressing unit that is configured to press the one of lateral faces of the reference gauge against the sphere contact portion.

11. The coefficient-of-thermal-expansion measuring device according to claim 1, further comprising:
a support adapter attached to the reference gauge and configured to be supported by the reference gauge support base, or a support adapter attached to the measurement target and configured to be supported by the measurement target support base.

12. The coefficient-of-thermal-expansion measuring device according to claim 1, further comprising
a preloading unit configured to downwardly preload the reference gauge.

13. The coefficient-of-thermal-expansion measuring device according to claim 2, wherein
each of the reference start points and the reference end points of the reference gauge are defined by one of:

a point on a surface of a protrusion provided on the reference gauge intersecting the drawing direction;
a virtual point on a central axis of a cylindrical hole to be detected provided to the reference gauge, the virtual point being obtained by detecting an inner circumferential surface of the hole to be detected using the coordinate measuring machine;
a virtual point on a central axis of a cylindrical cylinder to be measured provided to the reference gauge, the virtual point being obtained by detecting an outer circumferential surface of the cylinder to be measured using the coordinate measuring machine; and
a virtual point indicating a center of a ball to be measured provided to the reference gauge, the virtual point being obtained by detecting an outer circumferential surface of the ball to be measured using the coordinate measuring machine.

14. The coefficient-of-thermal-expansion measuring device according to claim 2, wherein
the reference gauge is in a form of a combination of a plurality of gauge blocks corresponding to the reference sections, end faces of the gauge blocks defining the reference start points and the reference end points.

15. The coefficient-of-thermal-expansion measuring device according to claim 2, wherein
the reference gauge comprises an insert hole at a position corresponding to at least one of the measurement start points and the measurement end points of the measurement target, the measurement probe of the coordinate measuring machine being insertable through the insert hole.

16. A coefficient-of-thermal-expansion measuring device of a measurement target in a form of a dimension reference gauge, the coefficient-of-thermal-expansion being measured for a section from a first surface to a second surface of the measurement target that are distanced in a drawing direction of the measurement target, the coefficient-of-thermal-expansion measuring device comprising:
a reference gauge having a known reference gauge length that is shorter than a length of the measurement target section;
a temperature-controlled chamber configured to adjust an interior temperature thereof and to house the measurement target and the reference gauge, the temperature-controlled chamber comprising a measurement surface provided with a measurement aperture; and
a coordinate measuring machine comprising a measurement probe that is introducible into an inside of the temperature-controlled chamber through the measurement aperture,
wherein
a plurality of relative measurement sections each having a length corresponding to the reference gauge length are allocated to the measurement target section, each of the plurality of relative measurement sections being shifted by a predetermined shift amount.

17. The coefficient-of-thermal-expansion measuring device according to claim 16, wherein
when the relative measurement sections are allocated to the measurement target section, the reference gauge is used, where the length of the measurement target section and the reference gauge length are in an integer ratio,
the shift amount is defined by a difference between the length of the measurement target section and the reference gauge length divided by an integer, and an allocated number of the relative measurement sections are assigned to the measurement target section, the allocated number being defined by a number, which is larger by one than a division of the difference between the length of the measurement target section and the reference gauge length by the shift amount.

18. The coefficient-of-thermal-expansion measuring device according to claim 16, wherein
a reference gauge movement mechanism configured to hold the reference gauge and to move the reference gauge to each of the plurality of relative measurement sections is provided in the temperature-controlled chamber.

19. The coefficient-of-thermal-expansion measuring device according to claim 16, wherein
the reference gauge comprises a plurality of gauge units corresponding to the plurality of relative measurement sections.

20. The coefficient-of-thermal-expansion measuring device according to claim 19, wherein
the reference gauge comprises a plurality of gauge blocks each having the reference gauge length corresponding to the length of the relative measurement section, the plurality of gauge blocks being combined and fixed while the plurality of gauge blocks are shifted with each other by a shift amount, and
a through hole penetrating through a top face and a bottom face is provided to a middle portion of each of the gauge blocks, an end of another one of the gauge blocks being visible through the through hole.

21. The coefficient-of-thermal-expansion measuring device according to claim 1, wherein
the reference gauge is made of a material of extremely low expansion coefficient or a material of zero expansion coefficient whose expansion due to a temperature change between the first temperature and the second temperature is below a detectable limit, or made of a material whose expansion coefficient is known.

22. The coefficient-of-thermal-expansion measuring device according to claim 2, wherein
the reference gauge is made of a material of extremely low expansion coefficient or a material of zero expansion coefficient whose expansion due to a temperature change between the first temperature and the second temperature is below a detectable limit, or made of a material whose expansion coefficient is known.

23. The coefficient-of-thermal-expansion measuring device according to claim 16, wherein
the reference gauge is made of a material of extremely low expansion coefficient or a material of zero expansion coefficient whose expansion due to a temperature change between the first temperature and the second temperature is below a detectable limit, or made of a material whose expansion coefficient is known.

24. A reference gauge for measuring a coefficient-of-thermal-expansion of a measurement target in a form of a dimension reference gauge, the coefficient-of-thermal-expansion of the measurement target being measured for a plurality of measurement sections defined by a plurality of pairs of a measurement start point and a measurement end point of the measurement target that are distanced in a drawing direction of the measurement target, the reference gauge comprising:
a plurality of pairs of reference start points and reference end points that define a plurality of reference sections corresponding to the plurality of measurement sections, a length of each of the reference sections being known.

* * * * *